US012376853B2

(12) United States Patent
Shelton, IV et al.

(10) Patent No.: US 12,376,853 B2
(45) Date of Patent: Aug. 5, 2025

(54) STAPLE CARTRIDGE COMPRISING A TISSUE THICKNESS COMPENSATOR

(71) Applicant: Cilag GmbH International, Zug (CH)

(72) Inventors: Frederick E. Shelton, IV, Hillsboro, OH (US); Lauren S. Weaner, West Chester, OH (US); Jerome R. Morgan, Cincinnati, OH (US); Michael J. Vendely, Lebanon, OH (US); Taylor W. Aronhalt, Loveland, OH (US); Chester O Baxter, III, Loveland, OH (US); Mark S. Zeiner, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/654,812

(22) Filed: May 3, 2024

(65) Prior Publication Data

US 2024/0358368 A1 Oct. 31, 2024

Related U.S. Application Data

(63) Continuation of application No. 17/532,360, filed on Nov. 22, 2021, now Pat. No. 12,004,741, which is a
(Continued)

(51) Int. Cl.
*A61B 17/072* (2006.01)
*A61B 17/068* (2006.01)
(Continued)

(52) U.S. Cl.
CPC ........ *A61B 17/072* (2013.01); *A61B 17/0684* (2013.01); *A61B 17/07207* (2013.01);
(Continued)

(58) Field of Classification Search
CPC .............. A61B 17/068; A61B 17/072; A61B 17/07207; A61B 17/0684;
(Continued)

(56) References Cited

U.S. PATENT DOCUMENTS 5,403,312 A 4/1995 Yates et al.
5,452,837 A * 9/1995 Williamson, IV .......................... A61B 17/07207
227/176.1
(Continued)

FOREIGN PATENT DOCUMENTS

JP 2013541982 A 11/2013

OTHER PUBLICATIONS

ASTM procedure D2240-00, "Standard Test Method for Rubber Property-Durometer Hardness," (Published Aug. 2000).

*Primary Examiner* — Scott A Smith

(57) ABSTRACT

A staple cartridge is disclosed. The staple cartridge can comprise a cartridge body comprising a deck and a bottom surface opposite the deck. The staple cartridge can comprise a plurality of staple cavities, wherein each staple cavity extends into the cartridge body from the deck to the bottom surface. Additionally, a plurality of wells can be defined into the staple cartridge from the deck to a lowermost surface of the well. A plurality of staples can be removably positioned in the staple cavities. The staple cartridge can comprise a tissue thickness compensator releasably secured to the cartridge body, wherein the tissue thickness compensator comprises a compensator body and a plurality of extensions extending from the compensator body into the wells, wherein at least one extension is compressed within one of the wells. Each well can surround at least one staple cavity and/or can extend between at least two staple cavities.

20 Claims, 30 Drawing Sheets

Related U.S. Application Data continuation of application No. 17/361,806, filed on Jun. 29, 2021, now Pat. No. 11,701,114, which is a continuation of application No. 16/441,564, filed on Jun. 14, 2019, now Pat. No. 11,185,325, which is a continuation of application No. 16/105,387, filed on Aug. 20, 2018, now Pat. No. 10,905,418, which is a continuation of application No. 14/587,192, filed on Dec. 31, 2014, now Pat. No. 10,052,104, which is a continuation of application No. 14/516,277, filed on Oct. 16, 2014, now Pat. No. 9,924,944.

(51) Int. Cl.
   *A61B 17/00* (2006.01)
   *A61B 17/29* (2006.01)

(52) U.S. Cl.
   CPC ............. *A61B 17/07292* (2013.01); *A61B 2017/00477* (2013.01); *A61B 17/068* (2013.01); *A61B 2017/07214* (2013.01); *A61B 2017/07228* (2013.01); *A61B 2017/07271* (2013.01); *A61B 2017/07285* (2013.01); *A61B 2017/2927* (2013.01)

(58) Field of Classification Search
   CPC ............ A61B 17/07292; A61B 17/115; A61B 17/1155; A61B 2017/00477; A61B 2017/07214; A61B 2017/07228; A61B 2017/07271; A61B 2017/2923; A61B 2017/2927
   USPC ..... 227/19, 175.1, 176.1, 180.1; 606/1, 139, 606/153, 219
   See application file for complete search history.

(56) References Cited

U.S. PATENT DOCUMENTS

| | | |
|---|---|---|
| 5,468,253 A | 11/1995 | Bezwada et al. |
| 5,833,695 A | 11/1998 | Yoon |
| 6,325,810 B1 | 12/2001 | Hamilton et al. |
| 6,656,193 B2 * | 12/2003 | Grant ............... A61B 17/072 606/220 |
| 7,000,818 B2 | 2/2006 | Shelton, IV et al. |
| 7,070,083 B2 | 7/2006 | Jankowski |
| 7,140,528 B2 | 11/2006 | Shelton, IV |
| 7,143,925 B2 | 12/2006 | Shelton, IV et al. |
| 7,147,138 B2 | 12/2006 | Shelton, IV |
| 7,401,721 B2 | 7/2008 | Holsten et al. |
| 7,422,139 B2 | 9/2008 | Shelton, IV et al. |
| 7,438,209 B1 | 10/2008 | Hess et al. |
| 7,464,849 B2 | 12/2008 | Shelton, IV et al. |
| 7,500,979 B2 | 3/2009 | Hueil et al. |
| 7,547,312 B2 | 6/2009 | Bauman et al. |
| 7,559,937 B2 | 7/2009 | de la Torre et al. |
| 7,635,074 B2 | 12/2009 | Olson et al. |
| 7,641,091 B2 | 1/2010 | Olson et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,726,537 B2 | 6/2010 | Olson et al. |
| 7,753,245 B2 | 7/2010 | Boudreaux et al. |
| 7,794,475 B2 | 9/2010 | Hess et al. |
| 7,845,533 B2 | 12/2010 | Marczyk et al. |
| 7,845,537 B2 | 12/2010 | Shelton, IV et al. |
| 7,866,528 B2 | 1/2011 | Olson et al. |
| 7,934,630 B2 | 5/2011 | Shelton, IV et al. |
| 7,950,561 B2 | 5/2011 | Aranyi |
| 7,966,799 B2 | 6/2011 | Morgan et al. |
| 7,980,443 B2 | 7/2011 | Scheib et al. |
| 7,997,469 B2 | 8/2011 | Olson et al. |
| 8,011,550 B2 | 9/2011 | Aranyi et al. |
| 8,011,555 B2 | 9/2011 | Tarinelli et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,317,070 B2 | 11/2012 | Hueil et al. |
| 8,371,491 B2 | 2/2013 | Huitema et al. |
| 8,393,514 B2 | 3/2013 | Shelton, IV et al. |
| 8,464,923 B2 | 6/2013 | Shelton, IV |
| 8,474,677 B2 | 7/2013 | Woodard, Jr. et al. |
| 8,496,683 B2 | 7/2013 | Prommersberger et al. |
| 8,529,600 B2 | 9/2013 | Woodard, Jr. et al. |
| 8,561,870 B2 | 10/2013 | Baxter, III et al. |
| 8,567,656 B2 | 10/2013 | Shelton, IV et al. |
| 8,584,920 B2 | 11/2013 | Hodgkinson |
| 8,608,045 B2 | 12/2013 | Smith et al. |
| 8,636,187 B2 | 1/2014 | Hueil et al. |
| 8,657,176 B2 | 2/2014 | Shelton, IV et al. |
| 8,678,263 B2 | 3/2014 | Viola |
| 8,733,613 B2 | 5/2014 | Huitema et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,535 B2 | 6/2014 | Shelton, IV et al. |
| 8,752,699 B2 | 6/2014 | Morgan et al. |
| 8,757,465 B2 | 6/2014 | Woodard, Jr. et al. |
| 8,763,877 B2 | 7/2014 | Schall et al. |
| 8,777,004 B2 | 7/2014 | Shelton, IV et al. |
| 8,783,542 B2 | 7/2014 | Riestenberg et al. |
| 8,789,741 B2 | 7/2014 | Baxter, III et al. |
| 8,800,838 B2 | 8/2014 | Shelton, IV |
| 8,814,024 B2 | 8/2014 | Woodard, Jr. et al. |
| 8,814,025 B2 | 8/2014 | Miller et al. |
| 8,840,003 B2 | 9/2014 | Morgan et al. |
| 8,857,694 B2 | 10/2014 | Shelton, IV et al. |
| 8,864,007 B2 | 10/2014 | Widenhouse et al. |
| 8,864,009 B2 | 10/2014 | Shelton, IV et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,925,782 B2 | 1/2015 | Shelton, IV |
| 8,978,954 B2 | 3/2015 | Shelton, IV et al. |
| 8,978,956 B2 | 3/2015 | Schall et al. |
| 9,016,542 B2 | 4/2015 | Shelton, IV et al. |
| 9,033,203 B2 | 5/2015 | Woodard, Jr. et al. |
| 9,044,227 B2 | 6/2015 | Shelton, IV et al. |
| 9,044,228 B2 | 6/2015 | Woodard, Jr. et al. |
| 9,050,084 B2 | 6/2015 | Schmid et al. |
| 9,055,941 B2 | 6/2015 | Schmid et al. |
| 9,072,535 B2 | 7/2015 | Shelton, IV et al. |
| 9,084,602 B2 | 7/2015 | Gleiman |
| 9,101,358 B2 | 8/2015 | Kerr et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,168,038 B2 | 10/2015 | Shelton, IV et al. |
| 9,198,644 B2 | 12/2015 | Balek et al. |
| 9,198,662 B2 | 12/2015 | Barton et al. |
| 9,204,880 B2 | 12/2015 | Baxter, III et al. |
| 9,211,120 B2 | 12/2015 | Scheib et al. |
| 9,216,019 B2 | 12/2015 | Schmid et al. |
| 9,220,500 B2 | 12/2015 | Swayze et al. |
| 9,232,941 B2 | 1/2016 | Mandakolathur Vasudevan et al. |
| 9,237,891 B2 | 1/2016 | Shelton, IV |
| 9,241,714 B2 | 1/2016 | Timm et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,307,965 B2 | 4/2016 | Ming et al. |
| 9,314,246 B2 | 4/2016 | Shelton, IV et al. |
| 9,320,518 B2 | 4/2016 | Henderson et al. |
| 9,320,523 B2 | 4/2016 | Shelton, IV et al. |
| 9,332,974 B2 | 5/2016 | Henderson et al. |
| 9,332,984 B2 | 5/2016 | Weaner et al. |
| 9,345,477 B2 | 5/2016 | Anim et al. |
| 9,345,481 B2 | 5/2016 | Hall et al. |
| 9,351,730 B2 | 5/2016 | Schmid et al. |

(56) References Cited

U.S. PATENT DOCUMENTS

| | | |
|---|---|---|
| 9,364,233 B2 | 6/2016 | Alexander, III et al. |
| 9,386,984 B2 | 7/2016 | Aronhalt et al. |
| 9,386,988 B2 | 7/2016 | Baxter, III et al. |
| 9,414,838 B2 | 8/2016 | Shelton, IV et al. |
| 9,480,476 B2 | 11/2016 | Aldridge et al. |
| 9,517,063 B2 | 12/2016 | Swayze et al. |
| 9,566,061 B2 | 2/2017 | Aronhalt et al. |
| 9,572,577 B2 | 2/2017 | Lloyd et al. |
| 9,585,657 B2 | 3/2017 | Shelton, IV et al. |
| 9,592,050 B2 | 3/2017 | Schmid et al. |
| 9,615,826 B2 | 4/2017 | Shelton, IV et al. |
| 9,693,777 B2 | 7/2017 | Schellin et al. |
| 9,700,317 B2 | 7/2017 | Aronhalt et al. |
| 9,757,124 B2 | 9/2017 | Schellin et al. |
| 9,770,245 B2 | 9/2017 | Swayze et al. |
| 9,775,608 B2 | 10/2017 | Aronhalt et al. |
| 9,788,834 B2 | 10/2017 | Schmid et al. |
| 9,795,384 B2 | 10/2017 | Weaner et al. |
| 9,839,420 B2 | 12/2017 | Shelton, IV et al. |
| 9,839,422 B2 | 12/2017 | Schellin et al. |
| 9,839,423 B2 | 12/2017 | Vendely et al. |
| 9,848,875 B2 | 12/2017 | Aronhalt et al. |
| 9,861,361 B2 | 1/2018 | Aronhalt et al. |
| 9,884,456 B2 | 2/2018 | Schellin et al. |
| 9,924,944 B2 | 3/2018 | Shelton, IV et al. |
| 10,052,104 B2 | 8/2018 | Shelton, IV et al. |
| 10,123,798 B2 | 11/2018 | Baxter, III et al. |
| 10,136,890 B2 | 11/2018 | Shelton, IV et al. |
| 10,213,198 B2 | 2/2019 | Aronhalt et al. |
| 10,390,823 B2 | 8/2019 | Shelton, IV et al. |
| 10,405,854 B2 | 9/2019 | Schmid et al. |
| 10,548,593 B2 | 2/2020 | Shelton, IV et al. |
| 10,905,418 B2 | 2/2021 | Shelton, IV et al. |
| 11,083,455 B2 | 8/2021 | Shelton, IV et al. |
| 11,185,325 B2 | 11/2021 | Shelton, IV et al. |
| 11,406,378 B2 | 8/2022 | Baxter et al. |
| 11,457,918 B2 | 10/2022 | Shelton, IV et al. |
| 11,464,512 B2 | 10/2022 | Shelton, IV et al. |
| 11,478,244 B2 | 10/2022 | DiNardo et al. |
| 11,701,114 B2 | 7/2023 | Shelton, IV et al. |
| 11,963,678 B2 * | 4/2024 | Huitema ............... A61B 17/068 |
| 12,004,741 B2 | 6/2024 | Shelton, IV et al. |
| 12,076,010 B2 * | 9/2024 | Shelton, IV ............. A61B 5/01 |
| 2007/0034669 A1 | 2/2007 | de la Torre et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2009/0206143 A1 | 8/2009 | Huitema et al. |
| 2012/0074198 A1 * | 3/2012 | Huitema .......... A61B 17/07207 227/176.1 |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0241503 A1 | 9/2012 | Baxter, III et al. |
| 2012/0248169 A1 | 10/2012 | Widenhouse et al. |
| 2013/0153641 A1 | 6/2013 | Shelton, IV et al. |
| 2013/0256373 A1 | 10/2013 | Schmid et al. |
| 2013/0256380 A1 | 10/2013 | Schmid et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0224857 A1 | 8/2014 | Schmid |
| 2014/0263552 A1 | 9/2014 | Hall et al. |
| 2014/0291379 A1 | 10/2014 | Schellin et al. |

* cited by examiner

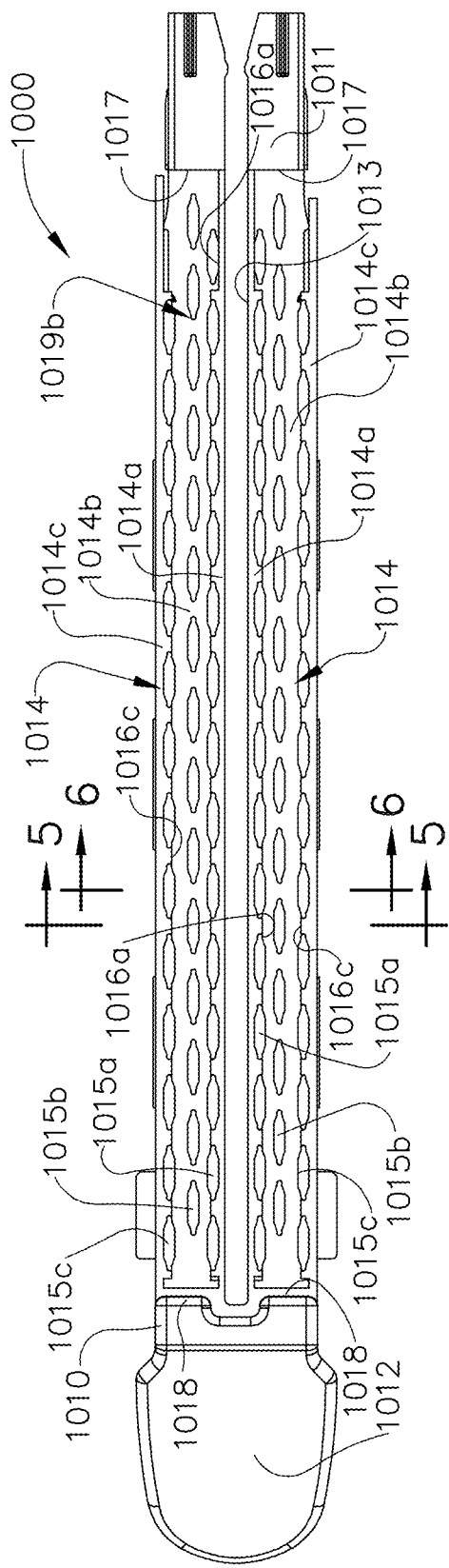
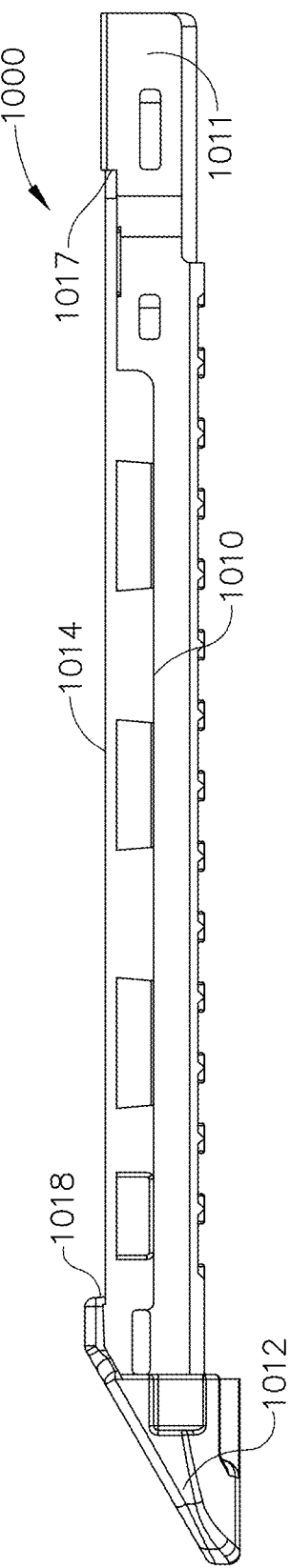
FIG. 3
FIG. 4

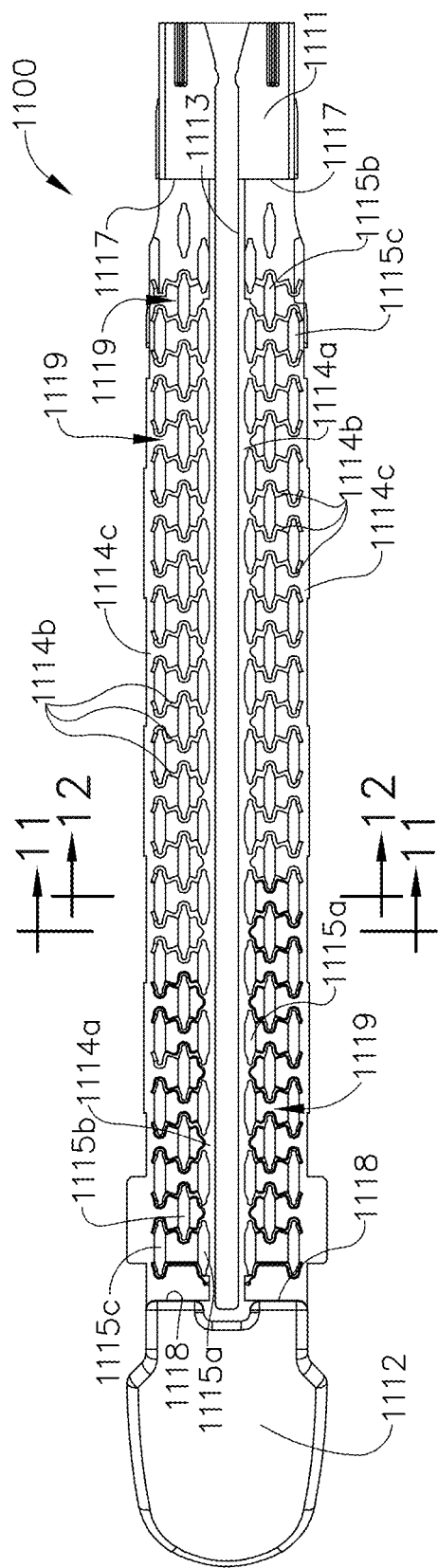
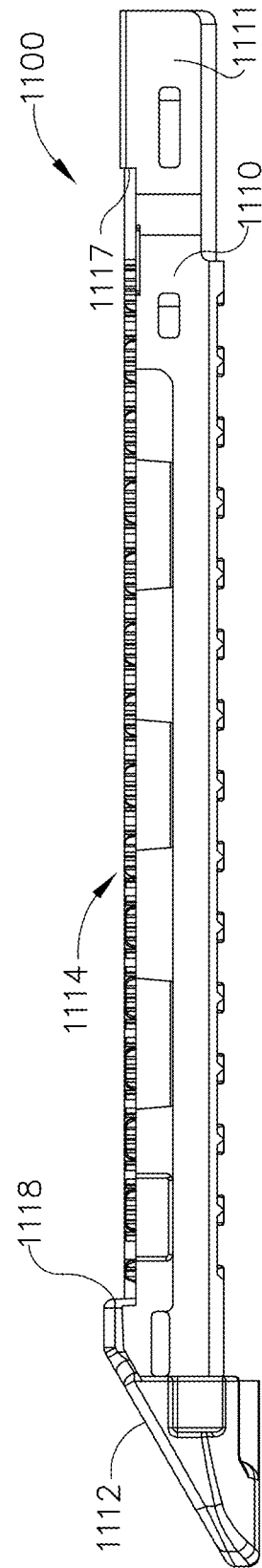
FIG. 9
FIG. 10

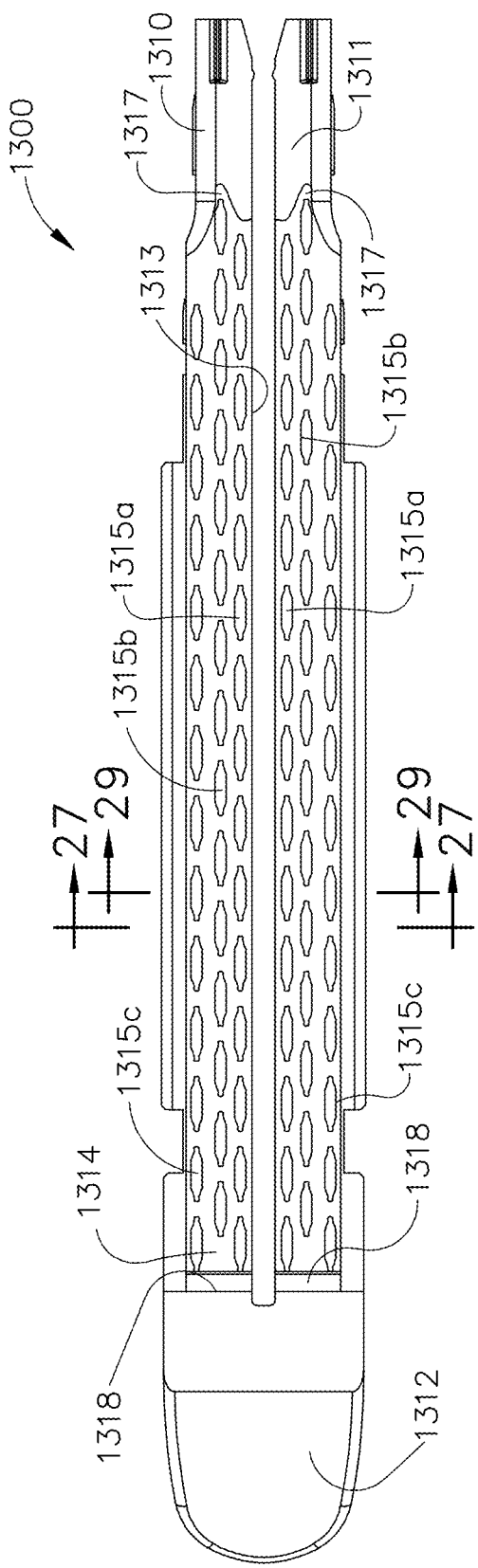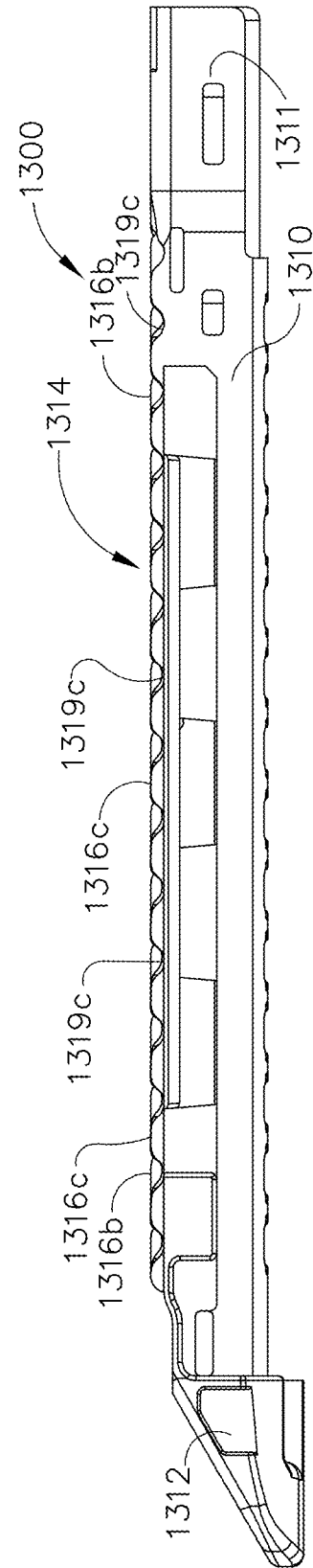
FIG. 21
FIG. 22

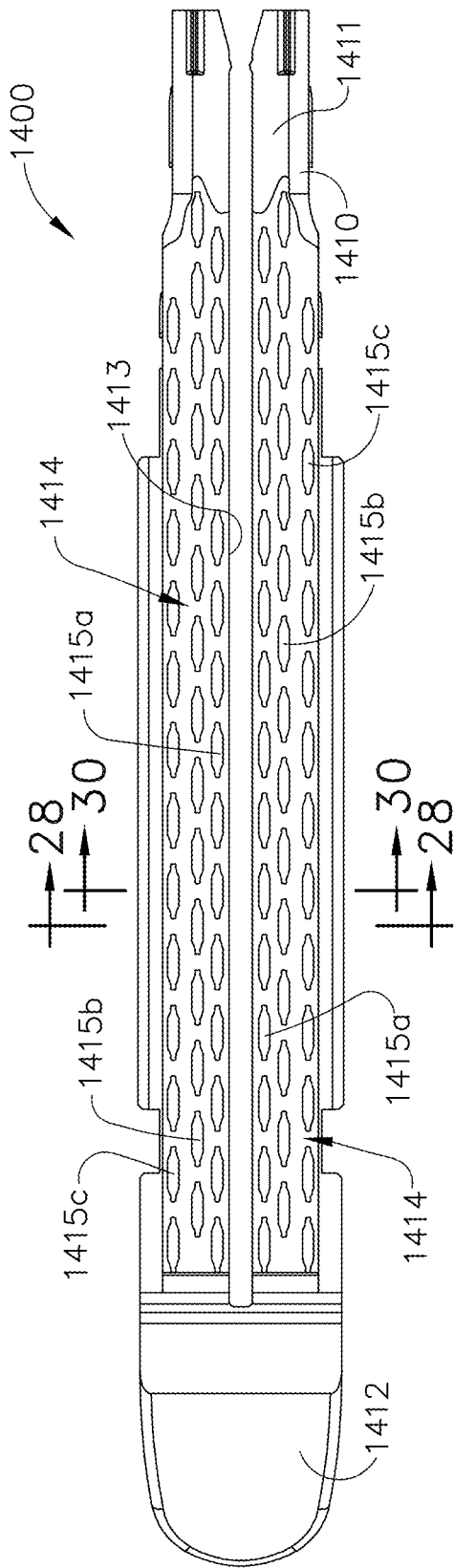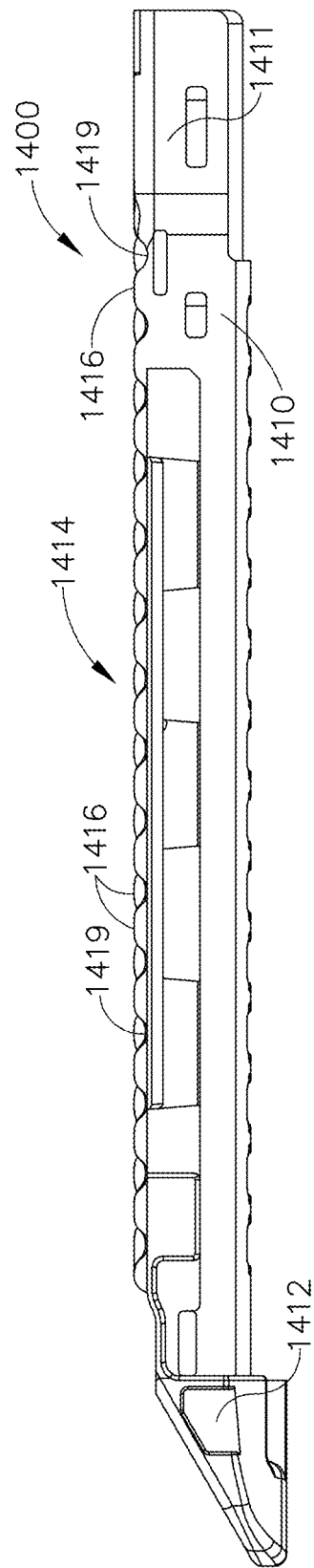
FIG. 25
FIG. 26

STAPLE CARTRIDGE COMPRISING A TISSUE THICKNESS COMPENSATOR

CROSS-REFERENCE TO RELATED APPLICATIONS

This application is a continuation application claiming priority under 35 U.S.C. § 120 to U.S. patent application Ser. No. 17/532,360, entitled STAPLE CARTRIDGE COMPRISING A TISSUE THICKNESS COMPENSATOR, filed Nov. 22, 2021, which issued on Jun. 11, 2024 as U.S. Pat. No. 12,004,741, which is a continuation application claiming priority under 35 U.S.C. § 120 to U.S. patent application Ser. No. 17/361,806, entitled STAPLE CARTRIDGE COMPRISING A TISSUE THICKNESS COMPENSATOR, filed Jun. 29, 2021, which issued on Jul. 18, 2023 as U.S. Pat. No. 11,701,114, which is a continuation application claiming priority under 35 U.S.C. § 120 to U.S. patent application Ser. No. 16/441,564, entitled END EFFECTOR INCLUDING DIFFERENT TISSUE GAPS, filed Jun. 14, 2019, which issued on Nov. 30, 2021 as U.S. Pat. No. 11,185,325, which is a continuation application claiming priority under 35 U.S.C. § 120 to U.S. patent application Ser. No. 16/105,387, entitled STAPLE CARTRIDGE COMPRISING A TISSUE THICKNESS COMPENSATOR, filed Aug. 20, 2018, which issued on Feb. 2, 2021 as U.S. Pat. No. 10,905,418, which is a continuation application claiming priority under 35 U.S.C. § 120 to U.S. patent application Ser. No. 14/587,192, entitled STAPLE CARTRIDGE COMPRISING A TISSUE THICKNESS COMPENSATOR, filed Dec. 31, 2014, which issued on Aug. 21, 2018 as U.S. Pat. No. 10,052,104, which is a continuation application claiming priority under 35 U.S.C. § 120 to U.S. patent application Ser. No. 14/516,277, entitled STAPLE CARTRIDGE COMPRISING AN ADJUNCT MATERIAL, filed Oct. 16, 2014, which issued on Mar. 27, 2018 as U.S. Pat. No. 9,924,944, the entire disclosures of which are hereby incorporated by reference herein.

BACKGROUND

The present invention relates to stapling instruments and, in various embodiments, to a surgical stapling instrument for producing one or more rows of staples.

A stapling instrument can include a pair of cooperating elongate jaw members, wherein each jaw member can be adapted to be inserted into a patient and positioned relative to tissue that is to be stapled and/or incised. In various embodiments, one of the jaw members can support a staple cartridge with at least two laterally spaced rows of staples contained therein, and the other jaw member can support an anvil with staple-forming pockets aligned with the rows of staples in the staple cartridge. Generally, the stapling instrument can further include a pusher bar and a knife blade which are slidable relative to the jaw members to sequentially eject the staples from the staple cartridge via camming surfaces on the pusher bar and/or camming surfaces on a wedge sled that is pushed by the pusher bar. In at least one embodiment, the camming surfaces can be configured to activate a plurality of staple drivers carried by the cartridge and associated with the staples in order to push the staples against the anvil and form laterally spaced rows of deformed staples in the tissue gripped between the jaw members. In at least one embodiment, the knife blade can trail the camming surfaces and cut the tissue along a line between the staple rows. Examples of such stapling instruments are disclosed in U.S. Pat. No. 7,794,475, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, the entire disclosure of which is hereby incorporated by reference herein.

The foregoing discussion is intended only to illustrate various aspects of the related art in the field of the invention at the time, and should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows:

FIG. 3 is a plan view of the staple cartridge of FIG. 1;

FIG. 4 is an elevational view of the staple cartridge of FIG. 1;

FIG. 9 is a plan view of the staple cartridge of FIG. 7;

FIG. 10 is an elevational view of the staple cartridge of FIG. 7;

FIG. 21 is a plan view of the staple cartridge of FIG. 19;

FIG. 22 is an elevational view of the staple cartridge of FIG. 19;

FIG. 25 is a plan view of the staple cartridge of FIG. 23;

FIG. 26 is an elevational view of the staple cartridge of FIG. 23;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
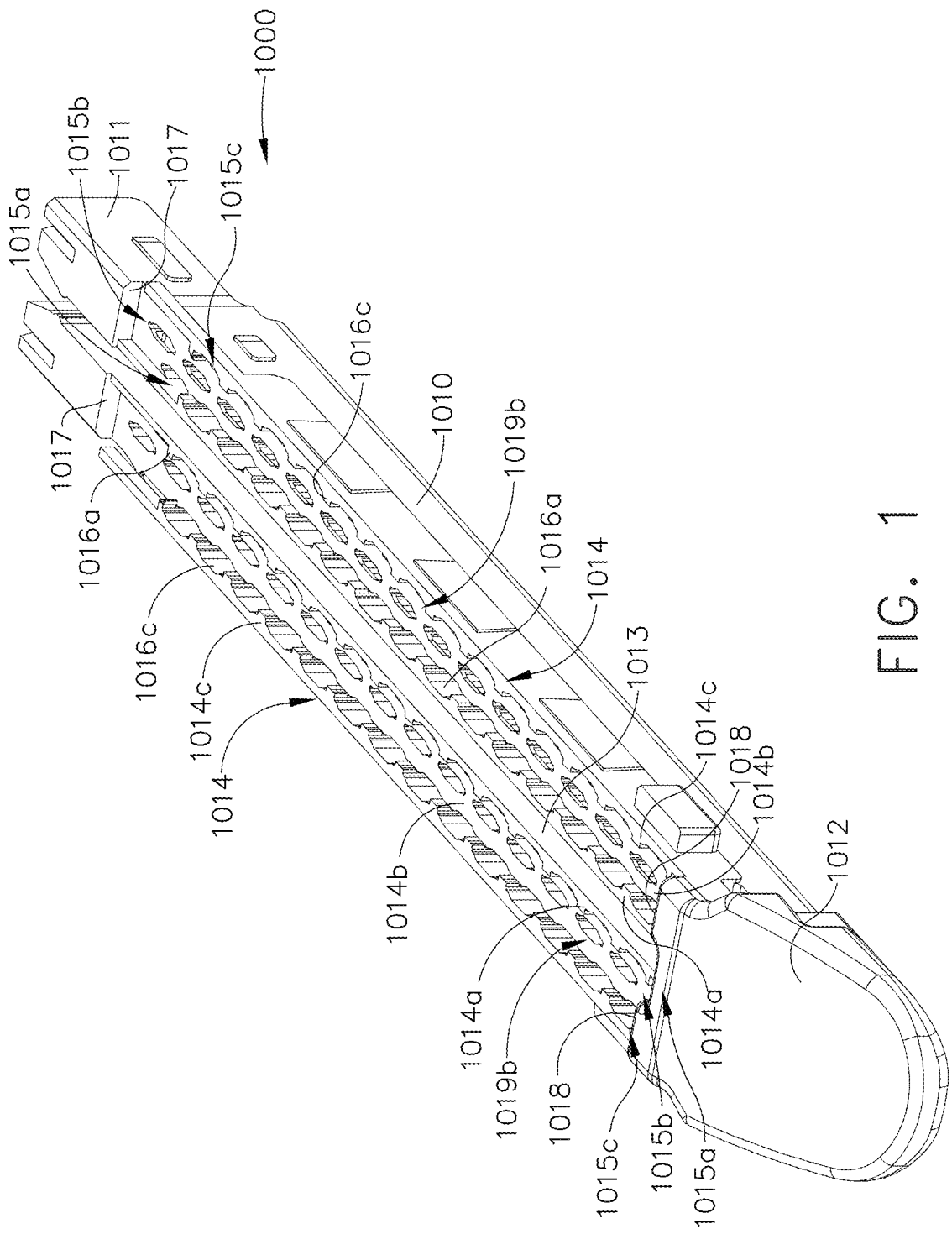
FIG. 1 is a perspective view of a staple cartridge in accordance with at least one embodiment comprising a stepped deck surface.
Figure 2:
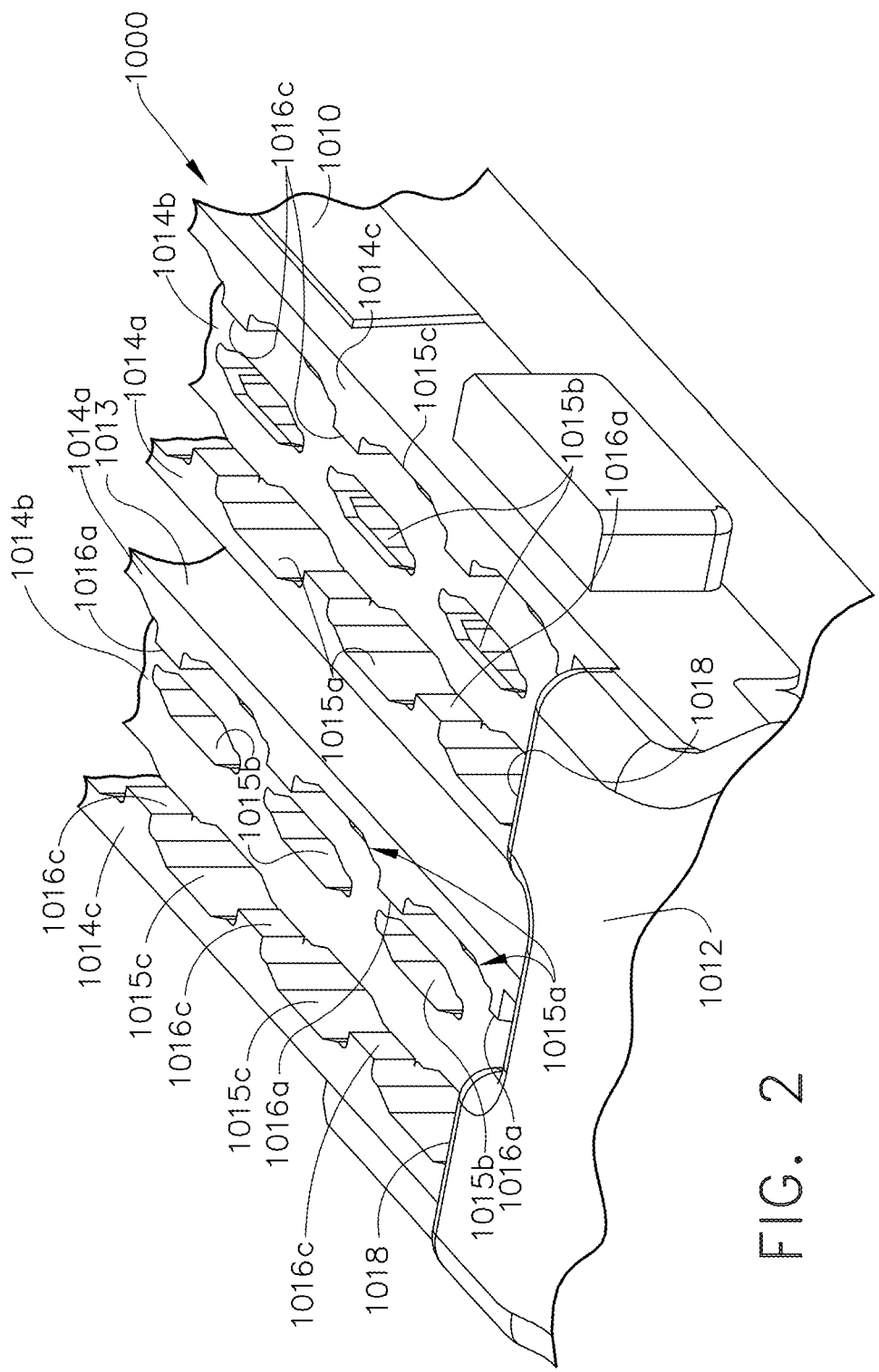
FIG. 2 is a detail view of the deck surface of the staple cartridge of FIG. 1.
Figure 5:
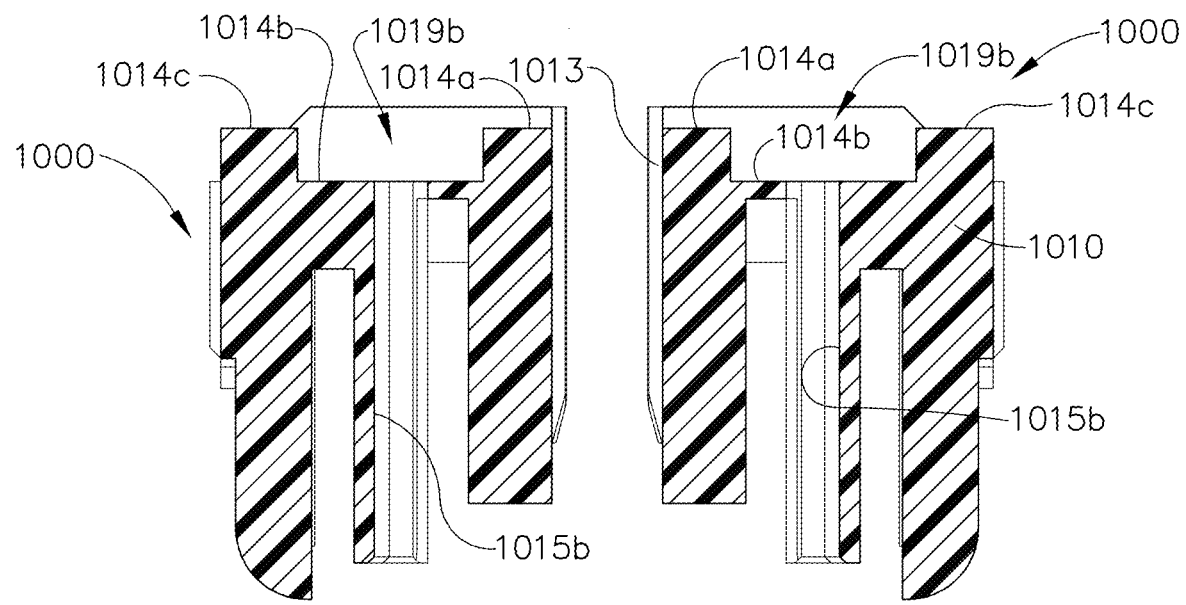
FIG. 5 is a cross-sectional view of the staple cartridge of FIG. 1 taken along line 5-5 in FIG. 3.

The Applicant of the present application also owns the U.S. patent applications identified below which are each herein incorporated by reference in their respective entirety:

U.S. patent application Ser. No. 12/894,311, entitled SURGICAL INSTRUMENTS WITH RECONFIGURABLE SHAFT SEGMENTS, now U.S. Pat. No. 8,763,877;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Pat. No. 8,899,463;

U.S. patent application Ser. No. 12/894,327, entitled JAW CLOSURE ARRANGEMENTS FOR SURGICAL INSTRUMENTS, now U.S. Pat. No. 8,978,956;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Pat. No. 9,113,864;

U.S. patent application Ser. No. 12/894,338, entitled IMPLANTABLE FASTENER CARTRIDGE HAVING A NON-UNIFORM ARRANGEMENT, now U.S. Pat. No. 8,864,007;

U.S. patent application Ser. No. 12/894,369, entitled IMPLANTABLE FASTENER CARTRIDGE COMPRISING A SUPPORT RETAINER, now U.S. Patent Application Publication No. 2012/0080344;

U.S. patent application Ser. No. 12/894,312, entitled IMPLANTABLE FASTENER CARTRIDGE COMPRISING MULTIPLE LAYERS, now U.S. Pat. No. 8,925,782;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Pat. No. 8,840,003;

U.S. patent application Ser. No. 12/894,360, entitled SURGICAL STAPLING INSTRUMENT WITH A VARIABLE STAPLE FORMING SYSTEM, now U.S. Pat. No. 9,113,862;

U.S. patent application Ser. No. 12/894,322, entitled SURGICAL STAPLING INSTRUMENT WITH INTERCHANGEABLE STAPLE CARTRIDGE ARRANGEMENTS, now U.S. Pat. No. 8,740,034;

U.S. patent application Ser. No. 12/894,350, entitled SURGICAL STAPLE CARTRIDGES WITH DETACHABLE SUPPORT STRUCTURES, now U.S. Patent Application Publication No. 2012/0080478;

U.S. patent application Ser. No. 12/894,383, entitled IMPLANTABLE FASTENER CARTRIDGE COMPRISING BIOABSORBABLE LAYERS, now U.S. Pat. No. 8,752,699;

U.S. patent application Ser. No. 12/894,389, entitled COMPRESSIBLE FASTENER CARTRIDGE, now U.S. Pat. No. 8,740,037;

U.S. patent application Ser. No. 12/894,345, entitled FASTENERS SUPPORTED BY A FASTENER CARTRIDGE SUPPORT, now U.S. Pat. No. 8,783,542;

U.S. patent application Ser. No. 12/894,306, entitled COLLAPSIBLE FASTENER CARTRIDGE, now U.S. Pat. No. 9,044,227;

U.S. patent application Ser. No. 12/894,318, entitled FASTENER SYSTEM COMPRISING A PLURALITY OF CONNECTED RETENTION MATRIX ELEMENTS, now U.S. Pat. No. 8,814,024;

U.S. patent application Ser. No. 12/894,330, entitled FASTENER SYSTEM COMPRISING A RETENTION MATRIX AND AN ALIGNMENT MATRIX, now U.S. Pat. No. 8,757,465;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Pat. No. 9,033,203;

U.S. patent application Ser. No. 12/894,388, entitled FASTENER SYSTEM COMPRISING A RETENTION MATRIX AND A COVER, now U.S. Pat. No. 8,474,677;

U.S. patent application Ser. No. 12/894,376, entitled FASTENER SYSTEM COMPRISING A PLURALITY OF FASTENER CARTRIDGES, now U.S. Pat. No. 9,044,228;

U.S. patent application Ser. No. 13/097,865, entitled SURGICAL STAPLER ANVIL COMPRISING A PLURALITY OF FORMING POCKETS, now U.S. Pat. No. 9,295,464;

U.S. patent application Ser. No. 13/097,936, entitled TISSUE THICKNESS COMPENSATOR FOR A SURGICAL STAPLER, now U.S. Pat. No. 8,657,176;

U.S. patent application Ser. No. 13/097,954, entitled STAPLE CARTRIDGE COMPRISING A VARIABLE THICKNESS COMPRESSIBLE PORTION, now U.S. Pat. No. 10,136,890;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Pat. No. 8,746,535;

U.S. patent application Ser. No. 13/097,891, entitled TISSUE THICKNESS COMPENSATOR FOR A SURGICAL STAPLER COMPRISING AN ADJUSTABLE ANVIL, now U.S. Pat. No. 8,864,009;

U.S. patent application Ser. No. 13/097,948, entitled STAPLE CARTRIDGE COMPRISING AN ADJUSTABLE DISTAL PORTION, now U.S. Pat. No. 8,978,954;

U.S. patent application Ser. No. 13/097,907, entitled COMPRESSIBLE STAPLE CARTRIDGE ASSEMBLY, now U.S. Pat. No. 9,301,755;

U.S. patent application Ser. No. 13/097,861, entitled TISSUE THICKNESS COMPENSATOR COMPRISING PORTIONS HAVING DIFFERENT PROPERTIES, now U.S. Pat. No. 9,113,865;

U.S. patent application Ser. No. 13/097,869, entitled STAPLE CARTRIDGE LOADING ASSEMBLY, now U.S. Pat. No. 8,857,694;

U.S. patent application Ser. No. 13/097,917, entitled COMPRESSIBLE STAPLE CARTRIDGE COMPRISING ALIGNMENT MEMBERS, now U.S. Pat. No. 8,777,004;

U.S. patent application Ser. No. 13/097,873, entitled STAPLE CARTRIDGE COMPRISING A RELEASABLE PORTION, now U.S. Pat. No. 8,740,038;

U.S. patent application Ser. No. 13/097,938, entitled STAPLE CARTRIDGE COMPRISING COMPRESSIBLE DISTORTION RESISTANT COMPONENTS, now U.S. Pat. No. 9,016,542;

U.S. patent application Ser. No. 13/097,924, entitled STAPLE CARTRIDGE COMPRISING A TISSUE THICKNESS COMPENSATOR, now U.S. Pat. No. 9,168,038;

U.S. patent application Ser. No. 13/242,029, entitled SURGICAL STAPLER WITH FLOATING ANVIL, now U.S. Pat. No. 8,893,949;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Pat. No. 9,055,941;

U.S. patent application Ser. No. 13/241,912, entitled STAPLE CARTRIDGE INCLUDING COLLAPSIBLE DECK ARRANGEMENT, now U.S. Pat. No. 9,050,084; U.S. patent application Ser. No. 13/241,922, entitled SURGICAL STAPLER WITH STATIONARY STAPLE DRIVERS, now U.S. Pat. No. 9,216,019;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Pat. No. 8,789,741;

U.S. patent application Ser. No. 13/241,629, entitled SURGICAL INSTRUMENT WITH SELECTIVELY ARTICULATABLE END EFFECTOR, now U.S. Patent Application Publication No. 2012/0074200;

U.S. patent application Ser. No. 13/433,096, entitled TISSUE THICKNESS COMPENSATOR COMPRISING A PLURALITY OF CAPSULES, now U.S. Pat. No. 9,301,752;

U.S. patent application Ser. No. 13/433,103, entitled TISSUE THICKNESS COMPENSATOR COMPRISING A PLURALITY OF LAYERS, now U.S. Pat. No. 9,433,419;

U.S. patent application Ser. No. 13/433,098, entitled EXPANDABLE TISSUE THICKNESS COMPENSATOR, now U.S. Pat. No. 9,301,753;

U.S. patent application Ser. No. 13/433,102, entitled TISSUE THICKNESS COMPENSATOR COMPRISING A RESERVOIR, now U.S. Pat. No. 9,232,941;

U.S. patent application Ser. No. 13/433,114, entitled RETAINER ASSEMBLY INCLUDING A TISSUE THICKNESS COMPENSATOR, now U.S. Pat. No. 9,386,988;

U.S. patent application Ser. No. 13/433,136, entitled TISSUE THICKNESS COMPENSATOR COMPRISING AT LEAST ONE MEDICAMENT, now U.S. Pat. No. 9,839,420;

U.S. patent application Ser. No. 13/433,141, entitled TISSUE THICKNESS COMPENSATOR COMPRISING CONTROLLED RELEASE AND EXPANSION, now U.S. Pat. No. 10,123,798;

U.S. patent application Ser. No. 13/433,144, entitled TISSUE THICKNESS COMPENSATOR COMPRISING FIBERS TO PRODUCE A RESILIENT LOAD, now U.S. Pat. No. 9,277,919;

U.S. patent application Ser. No. 13/433,148, entitled TISSUE THICKNESS COMPENSATOR COMPRISING STRUCTURE TO PRODUCE A RESILIENT LOAD, now U.S. Pat. No. 9,220,500;

U.S. patent application Ser. No. 13/433,155, entitled TISSUE THICKNESS COMPENSATOR COMPRISING RESILIENT MEMBERS, now U.S. Pat. No. 9,480,476;

U.S. patent application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. patent application Ser. No. 13/433,167, entitled TISSUE THICKNESS COMPENSATORS, now U.S. Pat. No. 9,220,501;

U.S. patent application Ser. No. 13/433,175, entitled LAYERED TISSUE THICKNESS COMPENSATOR, now U.S. Pat. No. 9,332,974;

U.S. patent application Ser. No. 13/433,179, entitled TISSUE THICKNESS COMPENSATORS FOR CIRCULAR SURGICAL STAPLERS, now U.S. Pat. No. 9,364,233;

U.S. patent application Ser. No. 13/763,028, entitled ADHESIVE FILM LAMINATE, now U.S. Pat. No. 9,282,962;

U.S. patent application Ser. No. 13/433,115, entitled TISSUE THICKNESS COMPENSATOR COMPRISING CAPSULES DEFINING A LOW PRESSURE ENVIRONMENT, now U.S. Pat. No. 9,204,880;

U.S. patent application Ser. No. 13/433,118, entitled TISSUE THICKNESS COMPENSATOR COMPRISED OF A PLURALITY OF MATERIALS, now U.S. Pat. No. 9,414,838;

U.S. patent application Ser. No. 13/433,135, entitled MOVABLE MEMBER FOR USE WITH A TISSUE THICKNESS COMPENSATOR, now U.S. Pat. No. 9,517,063;

U.S. patent application Ser. No. 13/433,140, entitled TISSUE THICKNESS COMPENSATOR AND METHOD FOR MAKING THE SAME, now U.S. Pat. No. 9,241,714;

U.S. patent application Ser. No. 13/433,129, entitled TISSUE THICKNESS COMPENSATOR COMPRISING A PLURALITY OF MEDICAMENTS, now U.S. Pat. No. 9,211,120;

U.S. patent application Ser. No. 11/216,562, entitled STAPLE CARTRIDGES FOR FORMING STAPLES HAVING DIFFERING FORMED STAPLE HEIGHTS, now U.S. Pat. No. 7,669,746;

U.S. patent application Ser. No. 11/714,049, entitled SURGICAL STAPLING DEVICE WITH ANVIL HAVING STAPLE FORMING POCKETS OF VARYING DEPTHS, now U.S. Patent Application Publication No. 2007/0194082;

U.S. patent application Ser. No. 11/711,979, entitled SURGICAL STAPLING DEVICES THAT PRODUCE FORMED STAPLES HAVING DIFFERENT LENGTHS, now U.S. Pat. No. 8,317,070;

U.S. patent application Ser. No. 11/711,975, entitled SURGICAL STAPLING DEVICE WITH STAPLE DRIVERS OF DIFFERENT HEIGHT, now U.S. Patent Application Publication No. 2007/0194079;

U.S. patent application Ser. No. 11/711,977, entitled SURGICAL STAPLING DEVICE WITH STAPLE DRIVER THAT SUPPORTS MULTIPLE WIRE DIAMETER STAPLES, now U.S. Pat. No. 7,673,781;

U.S. patent application Ser. No. 11/712,315, entitled SURGICAL STAPLING DEVICE WITH MULTIPLE STACKED ACTUATOR WEDGE CAMS FOR DRIVING STAPLE DRIVERS, now U.S. Pat. No. 7,500,979;

U.S. patent application Ser. No. 12/038,939, entitled STAPLE CARTRIDGES FOR FORMING STAPLES HAVING DIFFERING FORMED STAPLE HEIGHTS, now U.S. Pat. No. 7,934,630;

U.S. patent application Ser. No. 13/020,263, entitled SURGICAL STAPLING SYSTEMS THAT PRODUCE FORMED STAPLES HAVING DIFFERENT LENGTHS, now U.S. Pat. No. 8,636,187;

U.S. patent application Ser. No. 13/118,278, entitled ROBOTICALLY-CONTROLLED SURGICAL STAPLING DEVICES THAT PRODUCE FORMED STAPLES HAVING DIFFERENT LENGTHS, now U.S. Pat. No. 9,237,891;

U.S. patent application Ser. No. 13/369,629, entitled ROBOTICALLY-CONTROLLED CABLE-BASED SURGICAL END EFFECTORS, now U.S. Pat. No. 8,800,838;

U.S. patent application Ser. No. 12/695,359, entitled SURGICAL STAPLING DEVICES FOR FORMING STAPLES WITH DIFFERENT FORMED HEIGHTS, now U.S. Pat. No. 8,464,923;

U.S. patent application Ser. No. 13/072,923, entitled STAPLE CARTRIDGES FOR FORMING STAPLES HAVING DIFFERING FORMED STAPLE HEIGHTS, now U.S. Pat. No. 8,567,656;

U.S. patent application Ser. No. 13/766,325, entitled LAYER OF MATERIAL FOR A SURGICAL END EFFECTOR, now U.S. Patent Application Publication No. 2013/0256380;

U.S. patent application Ser. No. 13/763,078, entitled ANVIL LAYER ATTACHED TO A PROXIMAL END OF AN END EFFECTOR, now U.S. Pat. No. 9,848,875;

U.S. patent application Ser. No. 13/763,094, entitled LAYER COMPRISING DEPLOYABLE ATTACHMENT MEMBERS, now U.S. Pat. No. 9,788,834;

U.S. patent application Ser. No. 13/763,106, entitled END EFFECTOR COMPRISING A DISTAL TISSUE ABUTMENT MEMBER, now U.S. Pat. No. 9,592,050;

U.S. patent application Ser. No. 13/433,147, entitled TISSUE THICKNESS COMPENSATOR COMPRISING CHANNELS, now U.S. Pat. No. 9,351,730;

U.S. patent application Ser. No. 13/763,112, entitled SURGICAL STAPLING CARTRIDGE WITH LAYER RETENTION FEATURES, now U.S. Patent Application Publication No. 2013/0256379;

U.S. patent application Ser. No. 13/763,035, entitled ACTUATOR FOR RELEASING A TISSUE THICKNESS COMPENSATOR FROM A FASTENER CARTRIDGE, now U.S. Pat. No. 10,213,198;

U.S. patent application Ser. No. 13/763,042, entitled RELEASABLE TISSUE THICKNESS COMPENSATOR AND FASTENER CARTRIDGE HAVING THE SAME, now U.S. Pat. No. 9,861,361;

U.S. patent application Ser. No. 13/763,048, entitled FASTENER CARTRIDGE COMPRISING A RELEASABLE TISSUE THICKNESS COMPENSATOR, now U.S. Pat. No. 9,700,317;

U.S. patent application Ser. No. 13/763,054, entitled FASTENER CARTRIDGE COMPRISING A CUTTING MEMBER FOR RELEASING A TISSUE THICKNESS COMPENSATOR, now U.S. Pat. No. 9,272,406;

U.S. patent application Ser. No. 13/763,065, entitled FASTENER CARTRIDGE COMPRISING A RELEASABLY ATTACHED TISSUE THICKNESS COMPENSATOR, now U.S. Pat. No. 9,566,061;

U.S. patent application Ser. No. 13/763,021, entitled STAPLE CARTRIDGE COMPRISING A RELEASABLE COVER, now U.S. Pat. No. 9,386,984;

U.S. patent application Ser. No. 13/763,078, entitled ANVIL LAYER ATTACHED TO A PROXIMAL END OF AN END EFFECTOR, now U.S. Pat. No. 9,848,875;

U.S. patent application Ser. No. 13/763,095, entitled LAYER ARRANGEMENTS FOR SURGICAL STAPLE CARTRIDGES, now U.S. Pat. No. 9,770,245;

U.S. patent application Ser. No. 13/763,147, entitled IMPLANTABLE ARRANGEMENTS FOR SURGICAL STAPLE CARTRIDGES, now U.S. Patent Application Publication No. 2013/0153636;

U.S. patent application Ser. No. 13/763,192, entitled MULTIPLE THICKNESS IMPLANTABLE LAYERS FOR SURGICAL STAPLING DEVICES, now U.S. Pat. No. 9,615,826;

U.S. patent application Ser. No. 13/763,161, entitled RELEASABLE LAYER OF MATERIAL AND SURGICAL END EFFECTOR HAVING THE SAME, now U.S. Patent Application Publication No. 2013/0153641;

U.S. patent application Ser. No. 13/763,177, entitled ACTUATOR FOR RELEASING A LAYER OF MATERIAL FROM A SURGICAL END EFFECTOR, now U.S. Pat. No. 9,585,657;

U.S. patent application Ser. No. 13/763,037, entitled STAPLE CARTRIDGE COMPRISING A COMPRESSIBLE PORTION, now U.S. Patent Application Publication No. 2014/0224857;

U.S. patent application Ser. No. 13/433,126, entitled TISSUE THICKNESS COMPENSATOR COMPRISING TISSUE INGROWTH FEATURES, now U.S. Pat. No. 9,320,523;

U.S. patent application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373;

U.S. patent application Ser. No. 13/851,703, entitled FASTENER CARTRIDGE COMPRISING A TISSUE THICKNESS COMPENSATOR INCLUDING OPENINGS THEREIN, now U.S. Pat. No. 9,572,577;

U.S. patent application Ser. No. 13/851,676, entitled TISSUE THICKNESS COMPENSATOR COMPRISING A CUTTING MEMBER PATH, now U.S. Patent Application Publication No. 2014/0291379;

U.S. patent application Ser. No. 13/851,693, entitled FASTENER CARTRIDGE ASSEMBLIES, now U.S. Pat. No. 9,332,984;

U.S. patent application Ser. No. 13/851,684, entitled FASTENER CARTRIDGE COMPRISING A TISSUE THICKNESS COMPENSATOR AND A GAP SETTING ELEMENT, now U.S. Pat. No. 9,795,384;

U.S. patent application Ser. No. 14/187,387, entitled STAPLE CARTRIDGE INCLUDING A BARBED STAPLE, now U.S. Patent Application Publication No. 2014/0166724;

U.S. patent application Ser. No. 14/187,395, entitled STAPLE CARTRIDGE INCLUDING A BARBED STAPLE, now U.S. Patent Application Publication No. 2014/0166725;

U.S. patent application Ser. No. 14/187,400, entitled STAPLE CARTRIDGE INCLUDING A BARBED STAPLE, now U.S. Patent Application Publication No. 2014/0166726;

U.S. patent application Ser. No. 14/187,383, entitled IMPLANTABLE LAYERS AND METHODS FOR ALTERING IMPLANTABLE LAYERS FOR USE WITH SURGICAL FASTENING INSTRUMENTS, now U.S. Pat. No. 9,839,422;

U.S. patent application Ser. No. 14/187,386, entitled IMPLANTABLE LAYERS AND METHODS FOR ALTERING ONE OR MORE PROPERTIES OF IMPLANTABLE LAYERS FOR USE WITH FASTENING INSTRUMENTS, now U.S. Pat. No. 9,884,456;

U.S. patent application Ser. No. 14/187,390, entitled IMPLANTABLE LAYERS AND METHODS FOR MODIFYING THE SHAPE OF THE IMPLANTABLE LAYERS FOR USE WITH A SURGICAL FASTENING INSTRUMENT, now U.S. Pat. No. 9,839,423;

U.S. patent application Ser. No. 14/187,389, entitled IMPLANTABLE LAYER ASSEMBLIES, now U.S. Pat. No. 9,757,124;

U.S. patent application Ser. No. 14/187,385, entitled IMPLANTABLE LAYERS COMPRISING A PRESSED REGION, now U.S. Pat. No. 9,693,777; and U.S. patent application Ser. No. 14/187,384, entitled FASTENING SYSTEM COMPRISING A FIRING MEMBER LOCKOUT, now U.S. Pat. No. 9,775,608.

Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Many of the above-listed patent applications disclose various layers which are used in connection with a staple cartridge. When staples are deployed from the staple cartridge, the staples can capture at least one layer and implant the layer, or layers, against the tissue. Provided below is a brief description of a surgical stapling system. The staple cartridges and the layers disclosed herein can be used with this surgical stapling system and/or any suitable stapling system.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 6:
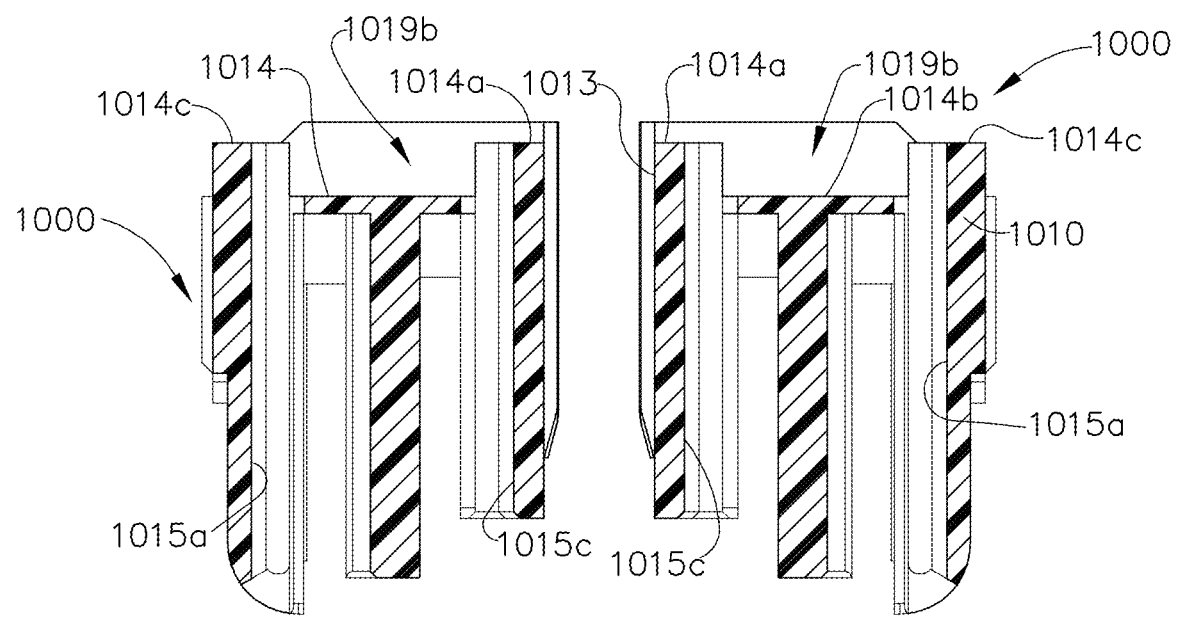
FIG. 6 is a cross-sectional view of the staple cartridge of FIG. 1 taken along line 6-6 in FIG. 3.
Figure 6A:
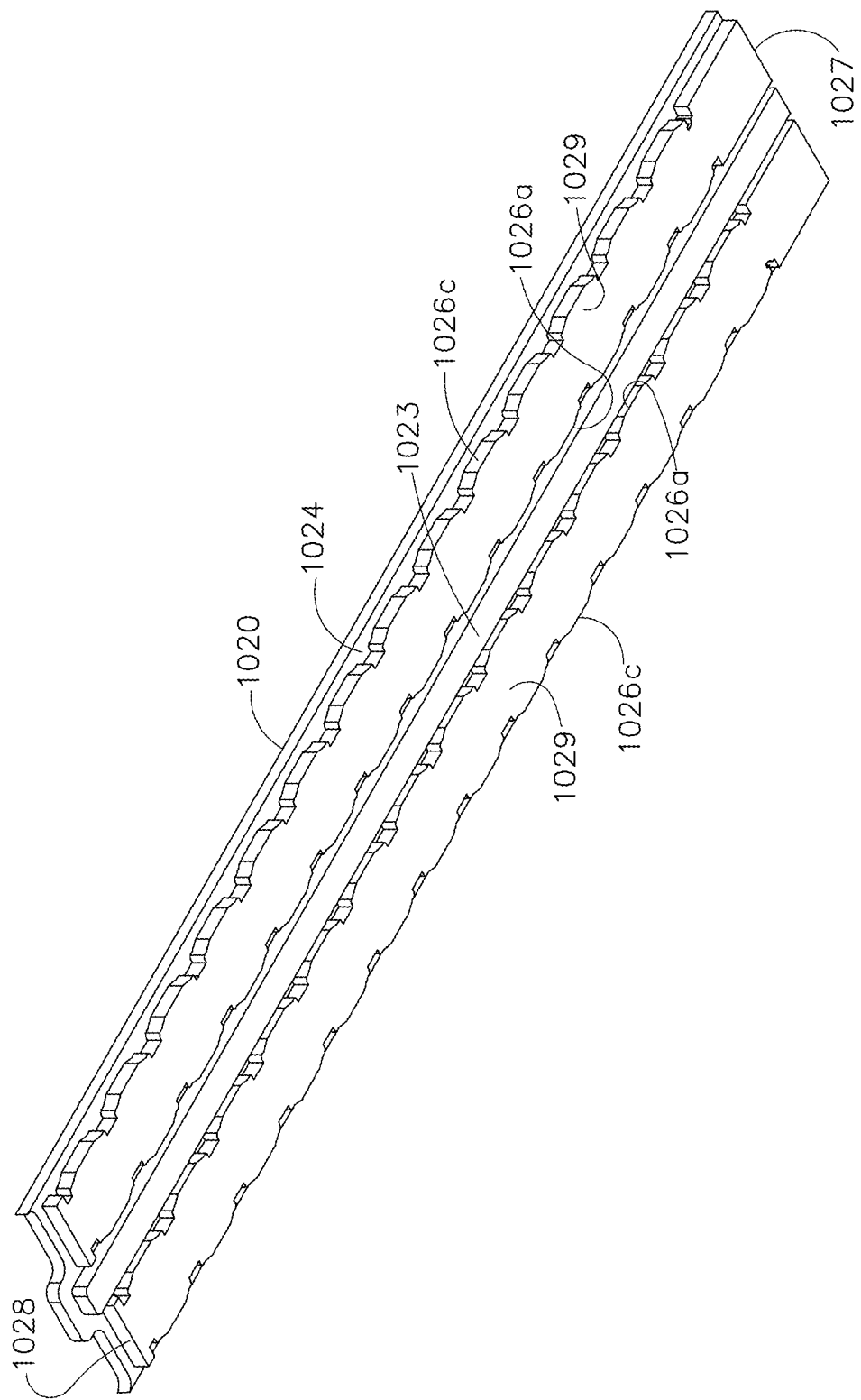
FIG. 6A is a perspective view of a layer usable with the staple cartridge of FIG. 1.

A staple cartridge assembly 1000 is depicted in FIGS. 1-6A. The staple cartridge assembly 1000 comprises a cartridge body 1010 and a layer 1020 (FIG. 6A). The cartridge body 1010 comprises a proximal end 1011 and a distal end 1012. The cartridge body 1010 further comprises a longitudinal slot 1013 defined therein which is configured to receive at least a portion of a firing member therein. The slot 1013 extends from the proximal end 1011 toward the distal end 1012. The cartridge body 1010 further comprises a plurality of staple cavities defined therein. The staple cavities are arranged in three longitudinal rows on a first side of the longitudinal slot 1013 and three longitudinal rows on a second side of the longitudinal slot 1013. On each side of the longitudinal slot 1013, a first longitudinal row of staple cavities 1015*a* extends alongside the longitudinal slot 1013, a second row of staple cavities 1015*b* extends alongside the first row of staple cavities 1015*a*, and a third row of staple cavities 1015*c* extends alongside the second row of staple cavities 1015*c*. The first row of staple cavities 1015*a*, the second row of staple cavities 1015*b*, and the third row of staple cavities 1015*c* are parallel to one another and the longitudinal slot 1013; however, embodiments are envisioned in which the first row of staple cavities 1015*a*, the second row of staple cavities 1015*b*, and/or the third row of staple cavities 1015*c* are not parallel to one another and/or the longitudinal slot 1013. Further to the above, the firing member can be configured to lift staple drivers positioned within the cartridge body 1010 to eject staples removably stored in the staple cavities 1015*a*, 1015*b*, and 1015*c* as the firing member is moved toward the distal end 1012 of the staple cartridge 1000.

The staple cartridge body 1010 further comprises a tissue-supporting deck 1014. The deck 1014 comprises a stepped surface. The deck 1014 comprises a first step 1014*a* adjacent the longitudinal slot 1013, a second step 1014*b* adjacent the first step 1014*a*, and a third step 1014*c* adjacent the second step 1014*b* on each side of the longitudinal slot 1013. The first step 1014*a* comprises a first plateau having a first height, the second step 1014*b* comprises a second plateau having a second height, and the third step 1014*c* comprises a third plateau having a third height. The first plateau and the third plateau have the same height. The first plateau and the third plateau are taller than the second plateau. Other embodiments are envisioned in which the first step, the second step, and the third step have any suitable height.

Further to the above, the second step 1014*b* of the deck 1014 is recessed with respect to the first step 1014*a* and the third step 1014*c*. The second step 1014*b* comprises a longitudinal depression, or well, 1019*b* extending between the first step 1014*a* and the third step 1014*c*. The longitudinal depression 1019*b* extends between the proximal end 1011 and the distal end 1012 of the cartridge body 1010. The second staple cavities 1015*b* are positioned within the longitudinal depression 1019b. The longitudinal depression 1019b is bounded by an inner lateral wall 1016a, an outer lateral wall 1016c, a proximal wall 1017, and a distal wall 1018. The proximal wall 1017 is positioned proximally with respect to the staple cavities 1015a, 1015b, and 1015c. The distal wall 1018 is positioned distally with respect to the staple cavities 1015a, 1015b, and 1015c. The inner wall 1016a transects the first staple cavities 1015a. The inner wall 1016a is at least partially comprised by the sidewalls of the first staple cavities 1015a. The deck 1014 surrounding the first staple cavities 1015a extends along the first step 1014a and the second step 1014b. The outer wall 1016c transects the third staple cavities 1015c. The outer wall 1016c is at least partially comprised by the sidewalls of the third staple cavities 1015c. The deck 1014 surrounding the third staple cavities 1015c extends along the third step 1014c and the second step 1014b.

The staple cartridge 1000 can be utilized with any suitable layer that can be implanted against the tissue being stapled. The layer can comprise an adjunct material which is positioned on the deck 1014 of the cartridge body 1010 before the staple cartridge 1000 is inserted into the patient. Such an adjunct material could comprise buttress material and/or a tissue thickness compensator, for example. In various instances, the layer can move relative to the deck 1014 when the staple cartridge 1000 and the layer are positioned relative to the tissue that is to be stapled.

Turning now to FIG. 6A, a layer 1020 comprises a bottom surface 1024 configured to contact and be supported by the deck 1014 of the cartridge body 1010. The layer 1020 further comprises longitudinal projections 1029 extending therefrom which are configured to be received in the longitudinal wells 1019b. The projections 1029 can limit relative motion between the layer 1020 and the cartridge body 1010. The projections 1029 are closely received between the inner wall 1016a and the outer wall 1016c and, as a result, the projections 1029 can abut the inner wall 1016a and/or the outer wall 1016c to limit lateral and/or longitudinal movement of the layer 1020. In various instances, each projection 1029 comprises a first lateral side wall 1026a configured to engage the inner wall 1016a and a second lateral side wall 1026b configured to engage the outer wall 1016b. The projections 1029 can be sized and configured such that they are compressed, or wedged, between the inner wall 1016a and the outer wall 1016c. Such compression, or wedging, can not only limit the lateral and longitudinal movement of the layer 1020, it can also limit unintentional vertical movement of the layer 1020 away from the deck 1014. As the reader will appreciate, the lateral compression, or wedging, is sufficient to hold the layer 1020 in position yet, at the same, it can be overcome to permit the layer 1020 to be separated from the cartridge body 1010 after the staples have been fired and the layer 1020 has been implanted against the tissue.

In addition to or in lieu of the above, the projections 1029 can limit longitudinal motion between the layer 1020 and the cartridge body 1010. The projections 1029 are closely received between the proximal wall 1017 and the distal wall 1018 and, as a result, the projections 1029 can abut the proximal wall 1017 and/or the distal wall 1018 to limit longitudinal movement of the layer 1020. In various instances, each projection 1029 comprises a proximal end wall 1027 configured to engage the proximal wall 1017 and a distal end wall 1028 configured to engage the distal wall 1018. The projections 1029 can be sized and configured such that they are compressed, or wedged, between the proximal wall 1017 and the distal wall 1018. Such compression, or wedging, can not only limit the longitudinal movement of the layer 1020, it can also limit unintentional vertical movement of the layer 1020 away from the deck 1014. As the reader will appreciate, the longitudinal compression, or wedging, is sufficient to hold the layer 1020 in position yet, at the same, it can be overcome to permit the layer 1020 to be separated from the cartridge body 1010 after the staples have been fired and the layer 1020 has been implanted against the tissue.

The projections 1029 comprise a negative impression of the voids created by the wells 1019b; however, the projections 1029 can comprise any suitable configuration. The projections 1029 are defined by contours which cause the projections 1029 to fit snugly within the wells 1019b. The projections 1029 can be larger than the wells 1019b such that the projections 1029 are compressed when they are positioned in the wells 1019b. Such an arrangement can generate a biasing and/or retention force between the layer 1020 and the cartridge body 1010.

Each staple cavity 1015a, 1015b, and 1015c is configured to removably store a staple therein. In various instances, the staples stored in the staple cavities 1015a, 1015b, and 1015c have the same unformed height. The unformed height of a staple is the overall height of the staple before it is deformed by an anvil. In certain instances, such staples can be deformed to the same formed height. In other instances, such staples can be deformed to different formed heights. For example, the staples ejected from the first staple cavities 1015a can be deformed to a first deformed height, the staples ejected from the second staple cavities 1015b can be deformed to a second deformed height, and the staples ejected from the third staple cavities 1015c can be deformed to a third deformed height. The first deformed height can be shorter than the second deformed height and the second deformed height can be shorter than the third deformed height. Such an arrangement can provide a tissue compression gradient with respect to an incision made in the tissue. In various instances, the staples stored in the staple cavities 1015a, 1015b, and 1015c can have different unformed heights. For example, the staples ejected from the first staple cavities 1015a can have a first unformed height, the staples ejected from the second staple cavities 1015b can have a second unformed height, and the staples ejected from the third staple cavities 1015c can have a third unformed height. The first unformed height can be shorter than the second unformed height and the second unformed height can be shorter than the third unformed height. In various other instances, the second unformed height can be shorter than the first unformed height and the third unformed height. In at least one such instance, the first unformed height and the third unformed height can be the same.

The disclosures of U.S. Pat. No. 7,866,528, entitled STAPLE DRIVE ASSEMBLY, which issued on Jan. 1, 2011; U.S. Pat. No. 7,726,537, entitled SURGICAL STAPLER WITH UNIVERSAL ARTICULATION AND TISSUE PRE-CLAMP, which issued on Jun. 1, 2010; U.S. Pat. No. 7,641,091, entitled STAPLE DRIVE ASSEMBLY, which issued on Jan. 5, 2010; U.S. Pat. No. 7,635,074, entitled STAPLE DRIVE ASSEMBLY, which issued on Dec. 22, 2009; and U.S. Pat. No. 7,997,469, entitled STAPLE DRIVE ASSEMBLY, which issued on Aug. 16, 2011, are hereby incorporated by reference herein in their respective entireties. The disclosure of U.S. Pat. No. 8,317,070, entitled SURGICAL STAPLING DEVICES THAT PRODUCE FORMED STAPLES HAVING DIFFERENT LENGTHS, which issued on Nov. 27, 2012, is incorporated by reference in its entirety.

Referring to FIGS. 1 and 6A, the layer 1020 comprises a longitudinal protrusion 1023 configured to extend into the longitudinal slot 1013 of the cartridge body 1010. The protrusion 1023 can be sized and configured such that it is wedged into and compressed within the slot 1013. The protrusion 1023 can be incised by the cutting portion of the firing member as the firing member is advanced distally. Such an incision can facilitate the release of the layer 1020 from the cartridge body 1010.

Figure 12:
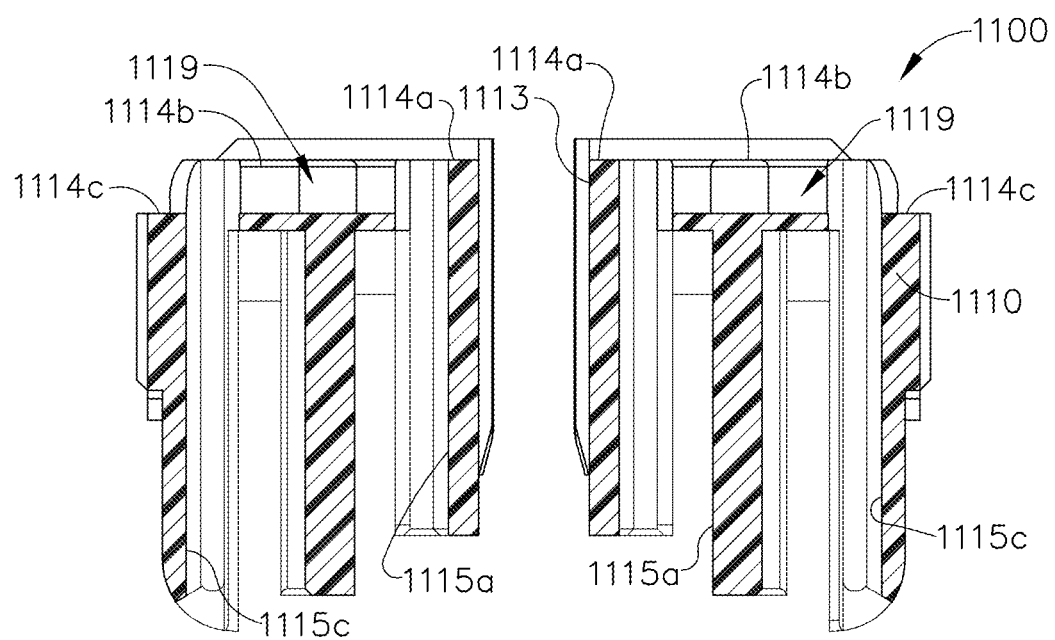
FIG. 12 is a cross-sectional view of the staple cartridge of FIG. 7 taken along line 12-12 in FIG. 9.
Figure 12A:
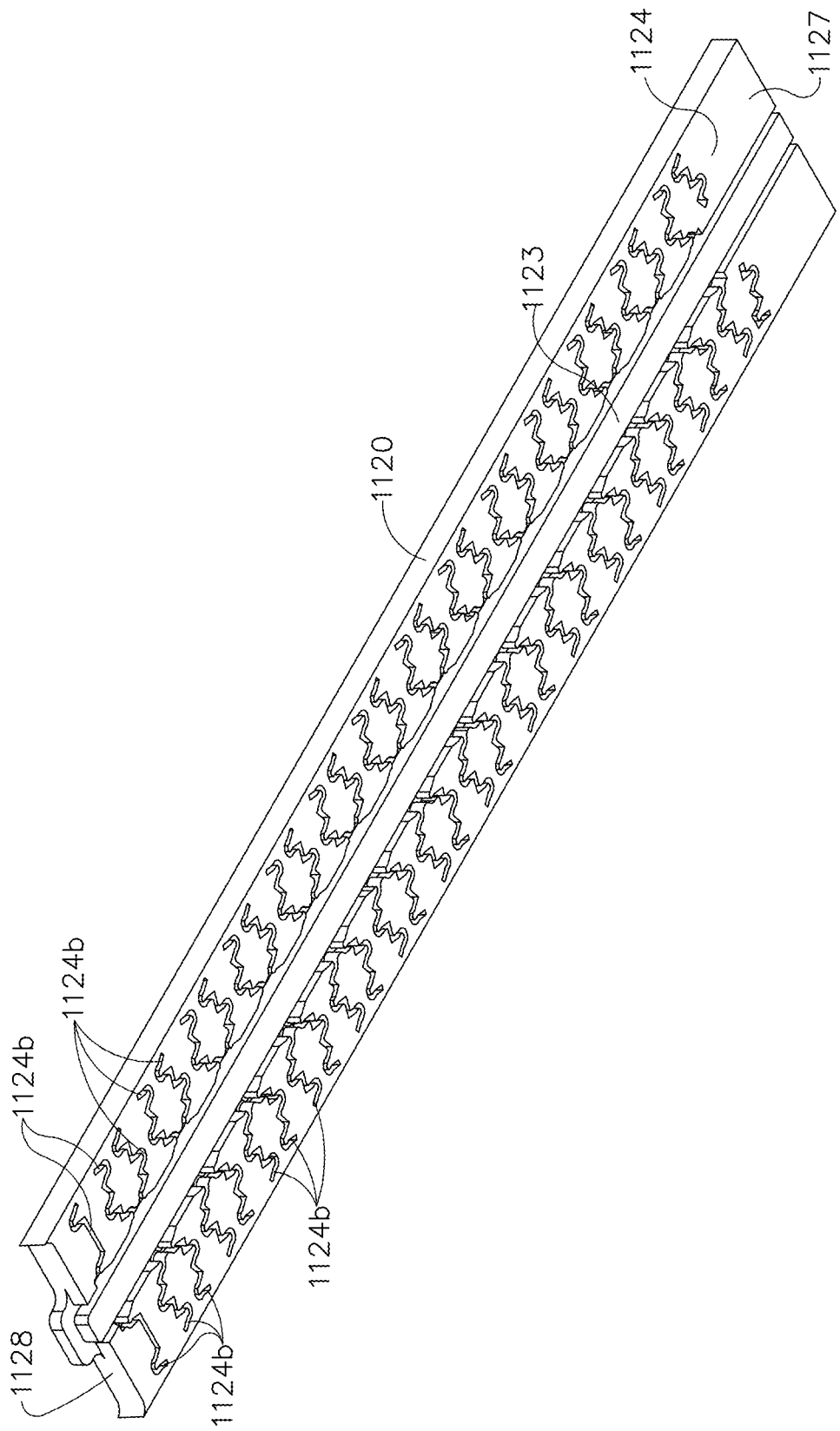
FIG. 12A is a perspective view of a layer usable with the staple cartridge of FIG. 7.
Figure 13:
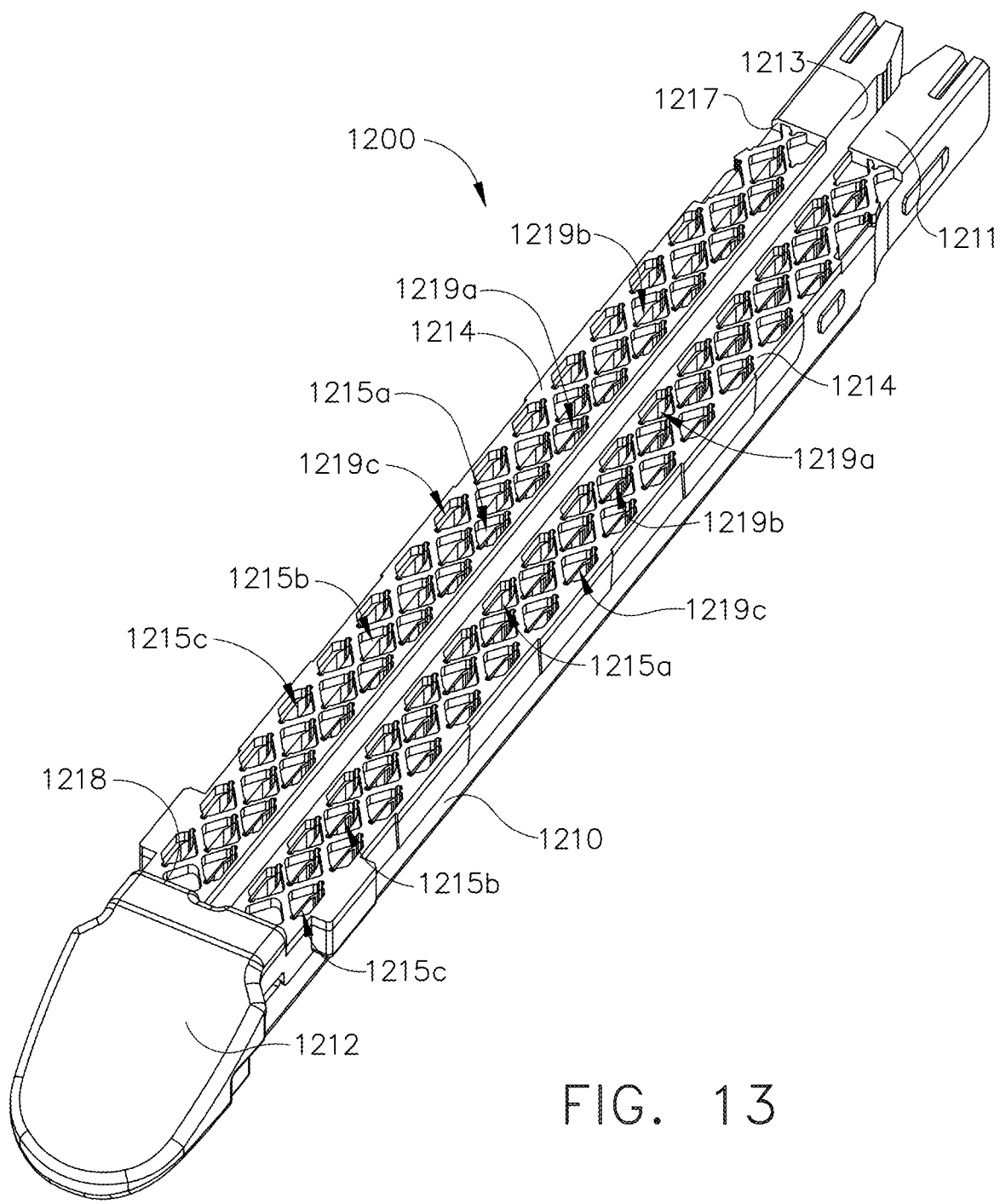
FIG. 13 is a perspective view of a staple cartridge in accordance with at least one embodiment comprising wells defined in a deck surface.
Figure 14:
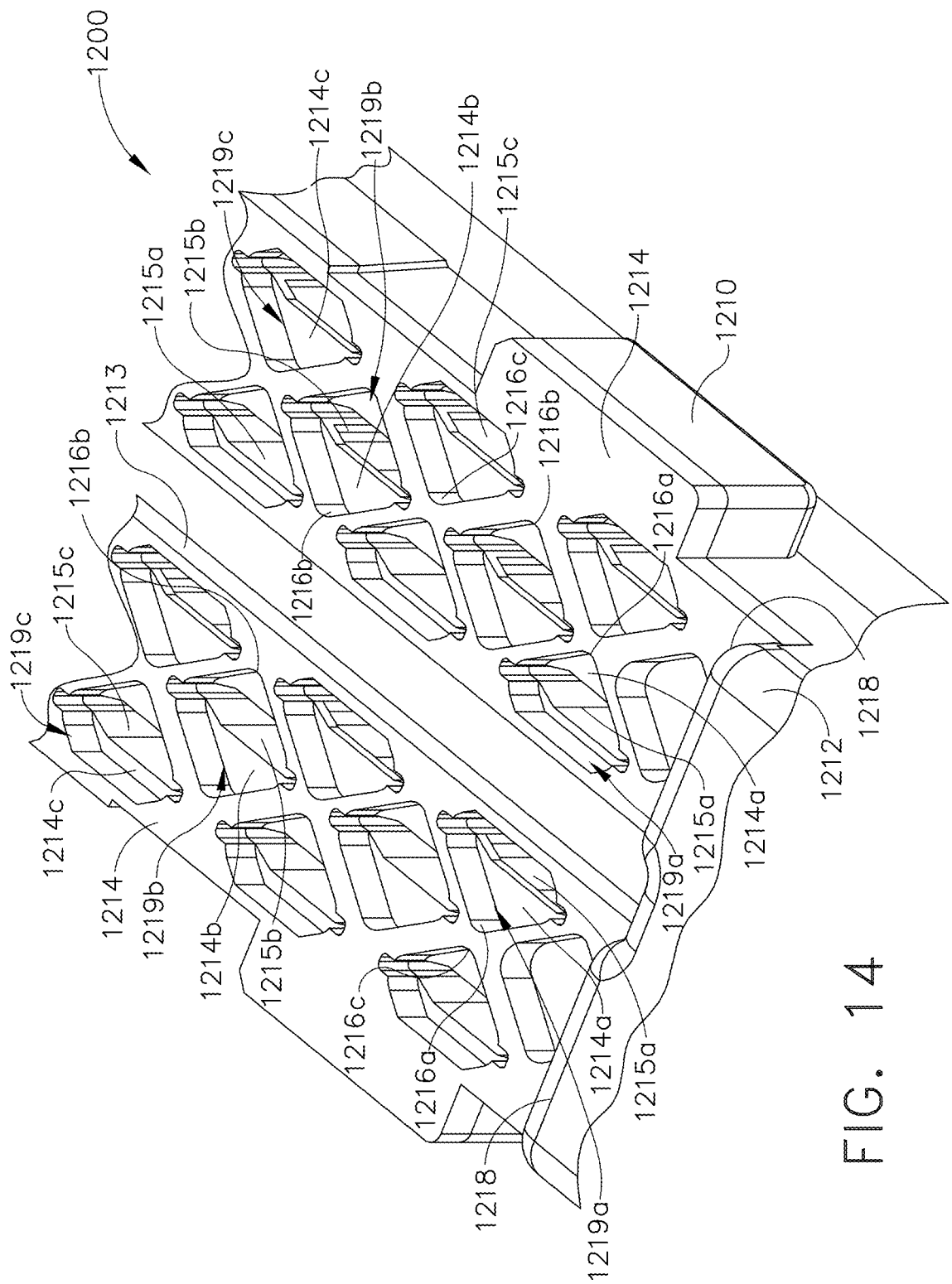
FIG. 14 is a detail view of the deck surface of the staple cartridge of FIG. 13.
Figure 15:
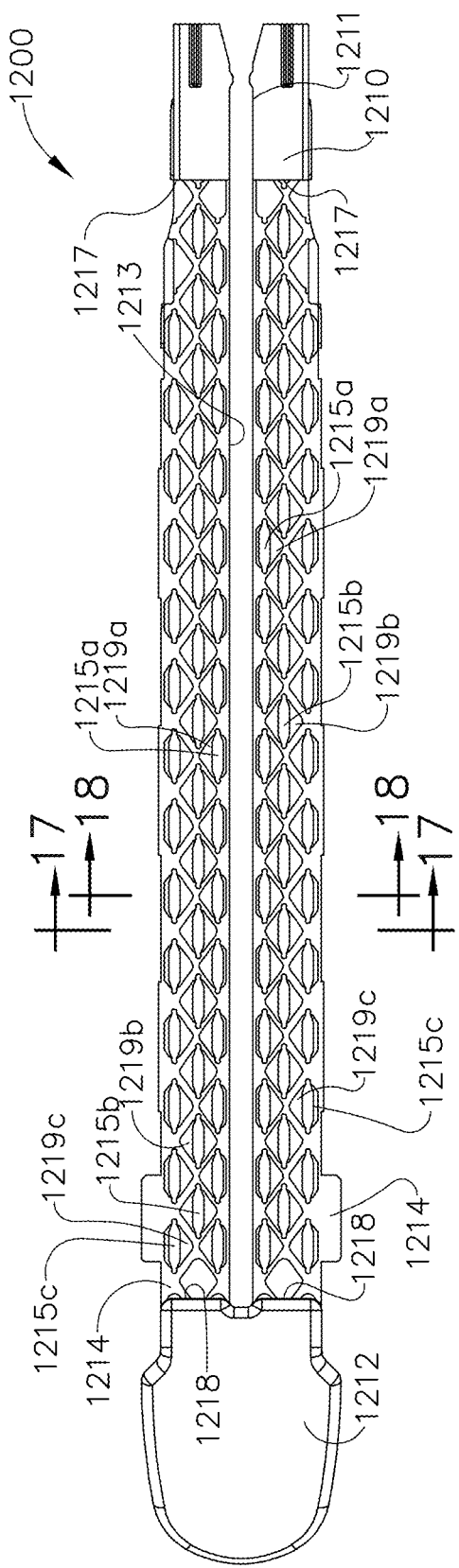
FIG. 15 is a plan view of the staple cartridge of FIG. 13.
Figure 16:
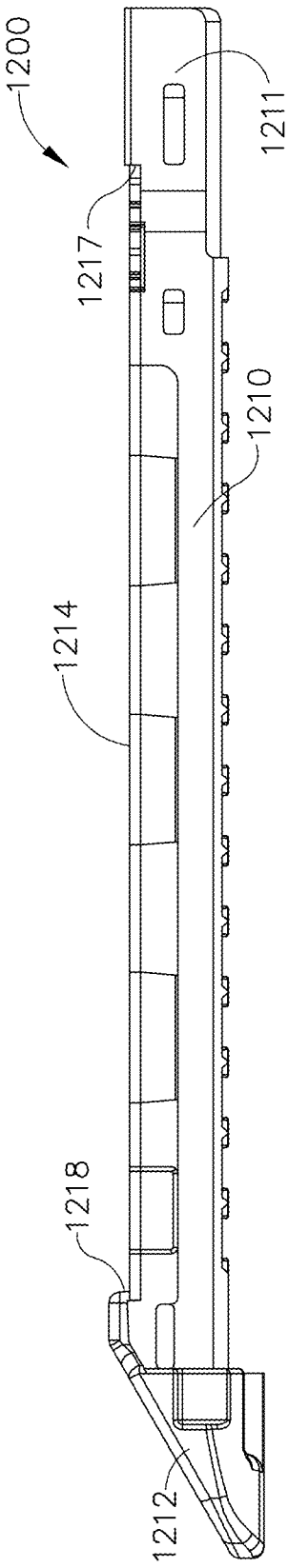
FIG. 16 is an elevational view of the staple cartridge of FIG. 13.
Figure 17:
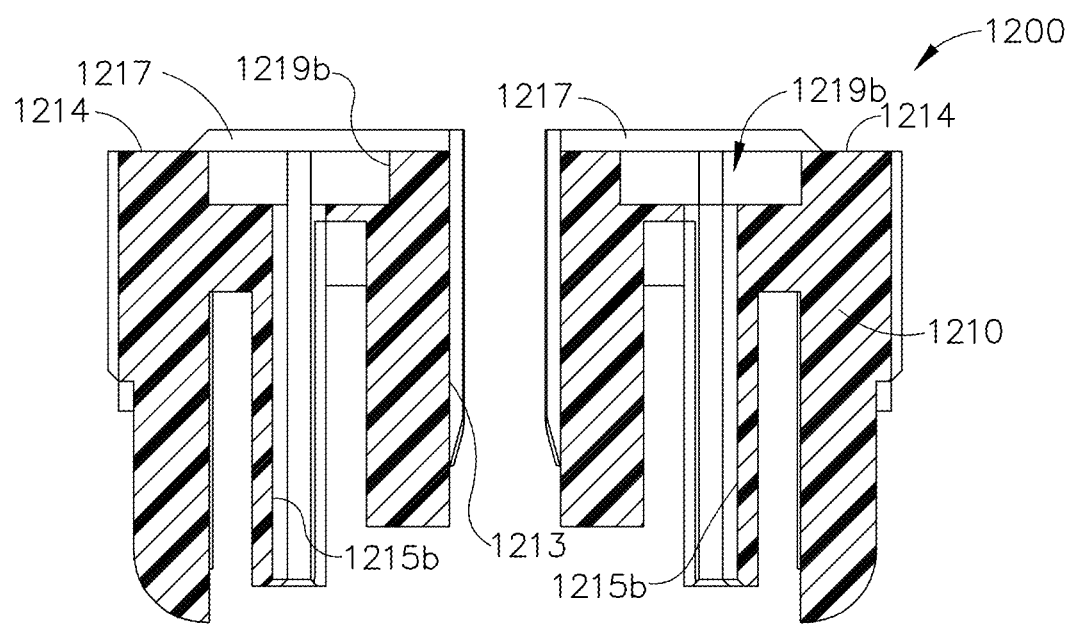
FIG. 17 is a cross-sectional view of the staple cartridge of FIG. 13 taken along line 17-17 in FIG. 15.

A staple cartridge assembly 1100 is depicted in FIGS. 7-12A. The staple cartridge assembly 1100 comprises a cartridge body 1110 and a layer 1120 (FIG. 12A). The cartridge body 1110 comprises a proximal end 1111 and a distal end 1112. The cartridge body 1110 further comprises a longitudinal slot 1113 defined therein which is configured to receive at least a portion of a firing member therein. The slot 1113 extends from the proximal end 1111 toward the distal end 1112. The cartridge body 1110 further comprises a plurality of staple cavities defined therein. The staple cavities are arranged in three longitudinal rows on a first side of the longitudinal slot 1113 and three longitudinal rows on a second side of the longitudinal slot 1113. On each side of the longitudinal slot 1113, a first longitudinal row of staple cavities 1115a extends alongside the longitudinal slot 1113, a second row of staple cavities 1115b extends alongside the first row of staple cavities 1115a, and a third row of staple cavities 1115c extends alongside the second row of staple cavities 1115b. The first row of staple cavities 1115a, the second row of staple cavities 1115b, and the third row of staple cavities 1115c are parallel to one another and the longitudinal slot 1113; however, embodiments are envisioned in which the first row of staple cavities 1115a, the second row of staple cavities 1115b, and/or the third row of staple cavities 1115c are not parallel to one another and/or the longitudinal slot 1113. Further to the above, the firing member can be configured to lift staple drivers positioned within the cartridge body 1110 to eject staples removably stored in the staple cavities 1115a, 1115b, and 1115c as the firing member is moved toward the distal end 1112 of the staple cartridge 1100.

The first staple cavities 1115a are positioned at regular intervals along a first longitudinal axis. Spaces between adjacent first staple cavities 1115a can be referred to as staple gaps in the first longitudinal row as tissue positioned over such spaces will not be stapled by staples ejected from the first staple cavities 1115a. The second staple cavities 1115b are also positioned at regular intervals along a second longitudinal axis. The second staple cavities 1115b are staggered with respect to the first staple cavities 1115a. The second staple cavities 1115b are positioned laterally with respect to the staple gaps in the first row of staple cavities 1115a. Spaces between adjacent second staple cavities 1115b can also be referred to as staple gaps in the second longitudinal row as tissue positioned over such spaces will not be stapled by staples ejected from the second staple cavities 1115b. The third staple cavities 1115c are also positioned at regular intervals along a third longitudinal axis. The third staple cavities 1115c are staggered with respect to the second staple cavities 1115b. The third staple cavities 1115c are positioned laterally with respect to the staple gaps in the second row of staple cavities 1115b.

The staple cartridge body 1110 further comprises a tissue-supporting deck 1114. The deck 1114 comprises a stepped surface. The deck 1114 comprises a first step 1114a adjacent the longitudinal slot 1113, a second step 1114b adjacent the first step 1114a, and a third step 1114c adjacent the second step 1114b. The deck 1114 comprises a first step 1114a, a second step 1114b, and a third step 1114c on each side of the longitudinal slot 1113. The first step 1114a comprises a first plateau having a first height, the second step 1114b comprises a plurality of walls having a second height, and the third step 1114c comprises a third plateau having a third height. The plurality of walls can collectively define a second plateau. The first plateau and the second plateau have the same height. The first plateau and the second plateau are taller than the third plateau. Other embodiments are envisioned in which the first step, the second step, and the third step have any suitable height.

Further to the above, the walls of the second step 1114b extend outwardly, or laterally, from the first step 1114a. The walls of the second step 1114b are connected to the first step 1114a; however, embodiments are envisioned in which the walls are not connected to the first step 1114a. Each wall extends around an end of a first staple cavity 1115a, a second staple cavity 1115b, and/or a third staple cavity 1115c. Owing to the staggered arrangement of the staple cavities 1115a, 1115b, and 1115c, discussed above, each wall weaves through the first row of staple cavities 1115a, the second row of staple cavities 1115b, and/or the third row of staple cavities 1115c. Each wall can comprise straight sections and/or curved sections. In various instances, the curved sections extend around the ends of the staple cavities while the straight sections extend between the rows of staple cavities.

The deck 1114 comprises a plurality of depressions, or wells, 1119. The wells 1119 are defined by the first step 1114a, the walls of the second step 1114b, a proximal wall 1117, and/or a distal wall 1118. The wells 1119 are not completely enclosed. Each well 1119 is bounded on three sides, i.e., a proximal side, a distal side, and an inner side. The outer side is unbounded, or at least substantially unbounded; however, other embodiments are envisioned in which the wells are bounded on less than three sides. Certain other embodiments are envisioned in which the wells are completely bounded. Each well 1119 comprises a bottom 1119b. The bottoms 1119b of the wells 1119 have the same height as the third step 1114c; however, other embodiments are envisioned in which the well bottoms 1119b have a different height than the third step 1114c.

The staple cartridge 1100 can be utilized with any suitable layer that can be implanted against the tissue being stapled. The layer can comprise an adjunct material which is positioned on the deck 1114 of the cartridge body 1110 before the staple cartridge 1100 is inserted into the patient. Such an adjunct material could comprise buttress material and/or a tissue thickness compensator, for example. In various instances, the layer can move relative to the deck 1114 when the staple cartridge 1100 and the layer are positioned relative to the tissue that is to be stapled.

Turning now to FIG. 12A, a layer 1120 comprises a bottom surface 1124 configured to contact and be supported by the deck 1114 of the cartridge body 1110. The layer 1120 further comprises slits 1124b which are configured to receive the walls of the second step 1114b. The interaction between the slits 1124b and the walls can limit relative motion between the layer 1120 and the cartridge body 1110. The walls of the second step 1114b are closely received in the slits 1124b and, as a result, the side walls of the slits 1124b can abut and/or grip the sidewalls of the walls of the second step 1114b to limit lateral movement of the layer 1120. Such an arrangement can generate a biasing and/or retention force between the layer 1120 and the cartridge body 1110. The walls of the second step 1114b can be sized and configured such that they are compressed, or wedged, within the slits 1124b. Such compression, or wedging, can not only limit the lateral and longitudinal movement of the layer 1120, it can also limit unintentional vertical movement of the layer 1120 away from the deck 1114. As the reader will appreciate, the lateral and longitudinal compression, or wedging, is sufficient to hold the layer 1120 in position yet, at the same, it can be overcome to permit the layer 1120 to be separated from the cartridge body 1110 after the staples have been fired and the layer 1120 has been implanted against the tissue.

The layer 1120 is closely received between the proximal wall 1117 and the distal wall 1118 and, as a result, the layer 1120 can abut the proximal wall 1117 and/or the distal wall 1118 to limit longitudinal movement of the layer 1120. The layer 1120 comprises a proximal end wall 1127 configured to engage the proximal wall 1117 and a distal end wall 1128 configured to engage the distal wall 1118. The layer 1120 can be sized and configured such that it is compressed, or wedged, between the proximal wall 1117 and the distal wall 1118. Such compression, or wedging, can not only limit the longitudinal movement of the layer 1120, it can also limit unintentional vertical movement of the layer 1120 away from the deck 1114. As the reader will appreciate, the longitudinal compression, or wedging, is sufficient to hold the layer 1120 in position yet, at the same, it can be overcome to permit the layer 1120 to be separated from the cartridge body 1110 after the staples have been fired and the layer 1120 has been implanted against the tissue.

Each staple cavity 1115a, 1115b, and 1115c is configured to removably store a staple therein. In various instances, the staples stored in the staple cavities 1115a, 1115b, and 1115c have the same unformed height. In certain instances, such staples can be deformed to the same formed height. In other instances, such staples can be deformed to different formed heights. For example, the staples ejected from the first staple cavities 1115a can be deformed to a first deformed height, the staples ejected from the second staple cavities 1115b can be deformed to a second deformed height, and the staples ejected from the third staple cavities 1115c can be deformed to a third deformed height. The first deformed height can be shorter than the second deformed height and the second deformed height can be shorter than the third deformed height. Such an arrangement can provide a tissue compression gradient with respect to an incision made in the tissue. In various instances, the staples stored in the staple cavities 1115a, 1115b, and 1115c can have different unformed heights. For example, the staples ejected from the first staple cavities 1115a can have a first unformed height, the staples ejected from the second staple cavities 1115b can have a second unformed height, and the staples ejected from the third staple cavities 1115c can have a third unformed height. The first unformed height can be shorter than the second unformed height and the second unformed height can be shorter than the third unformed height. In various other instances, the second unformed height can be shorter than the first unformed height. In at least one instance, the second unformed height and the third unformed height can be the same.

In various instances, the walls of the second step 1114a can be configured to guide the staples as the staples are ejected from the staple cavities 1115a, 1115b, and/or 1115c. In certain instances, the walls of the second step 1114a can extend the staple cavities 1115a, 1115b, and/or 1115c to control the staples stored therein as they are being ejected.

Figure 7:
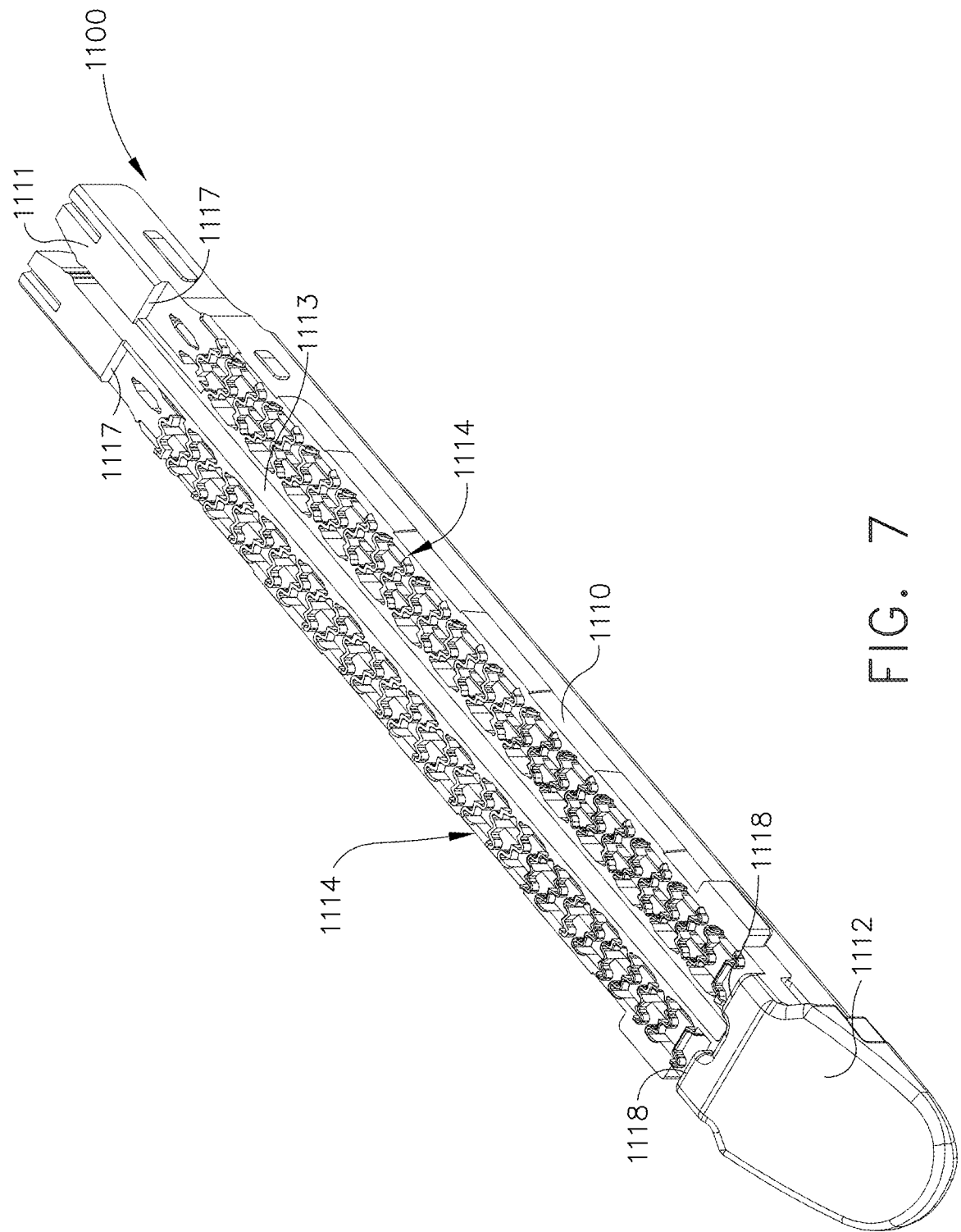
FIG. 7 is a perspective view of a staple cartridge in accordance with at least one embodiment comprising a ridged deck surface.
Figure 8:
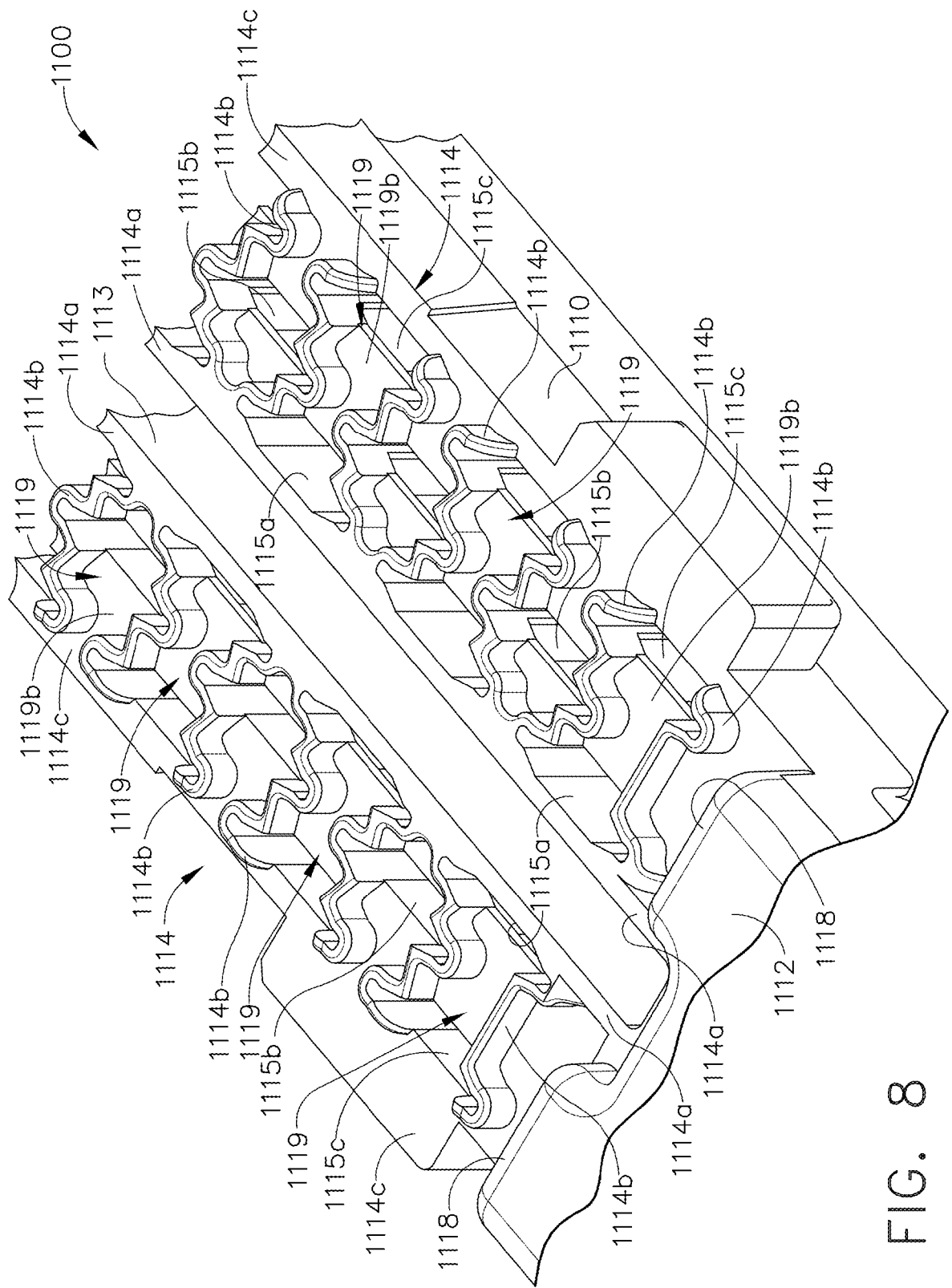
FIG. 8 is a detail view of the deck surface of the staple cartridge of FIG. 7.
Figure 11:
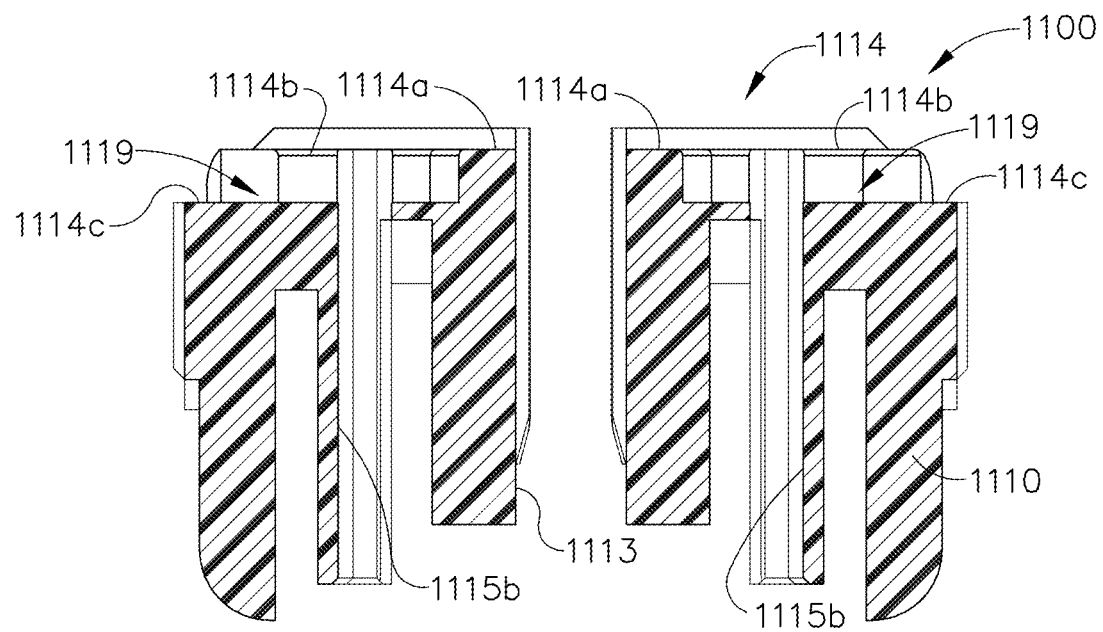
FIG. 11 is a cross-sectional view of the staple cartridge of FIG. 7 taken along line 11-11 in FIG. 9.

Referring to FIGS. 7 and 12A, the layer 1120 comprises a longitudinal protrusion 1123 configured to extend into the longitudinal slot 1113 of the cartridge body 1110. The protrusion 1123 can be sized and configured such that it is wedged into and compressed within the slot 1113. The protrusion 1123 can be incised by the cutting portion of the firing member as the firing member is advanced distally. Such an incision can facilitate the release of the layer 1120 from the cartridge body 1110.

Figure 18:
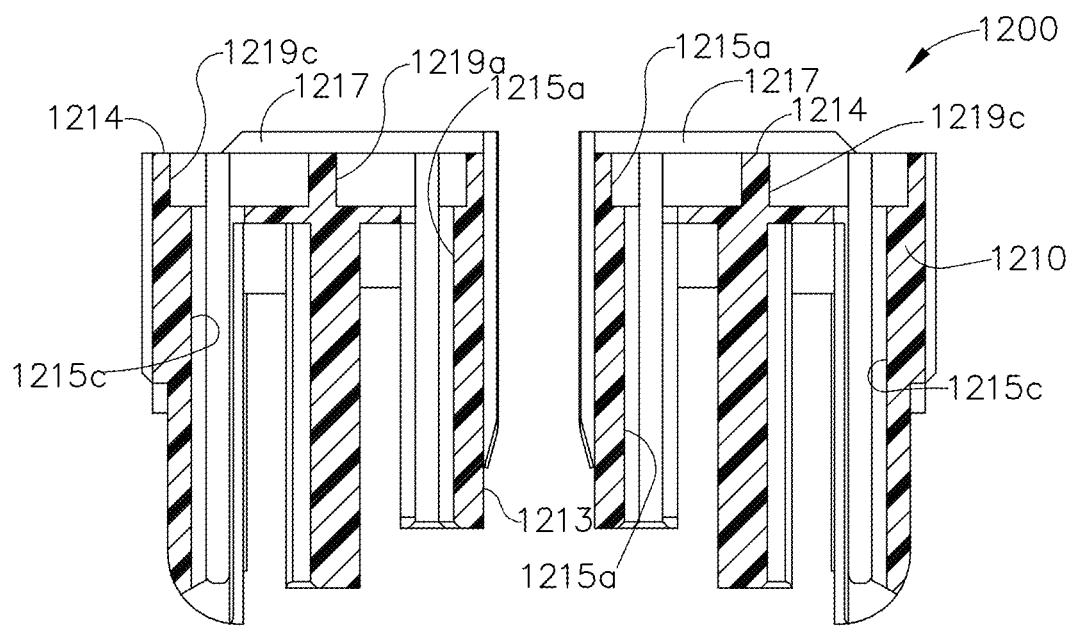
FIG. 18 is a cross-sectional view of the staple cartridge of FIG. 13 taken along line 18-18 in FIG. 15.
Figure 18A:
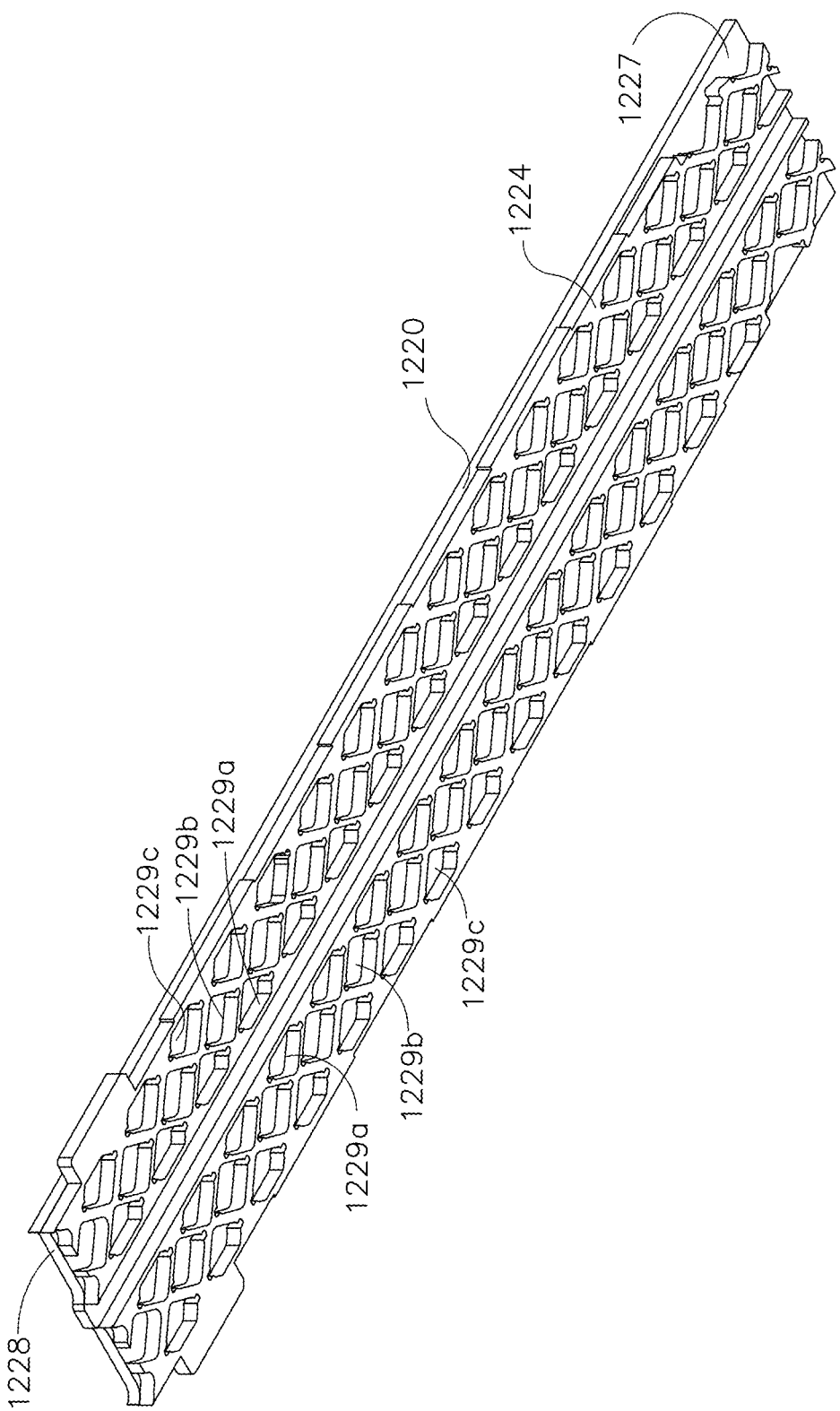
FIG. 18A is a perspective view of a layer usable with the staple cartridge of FIG. 13.
Figure 19:
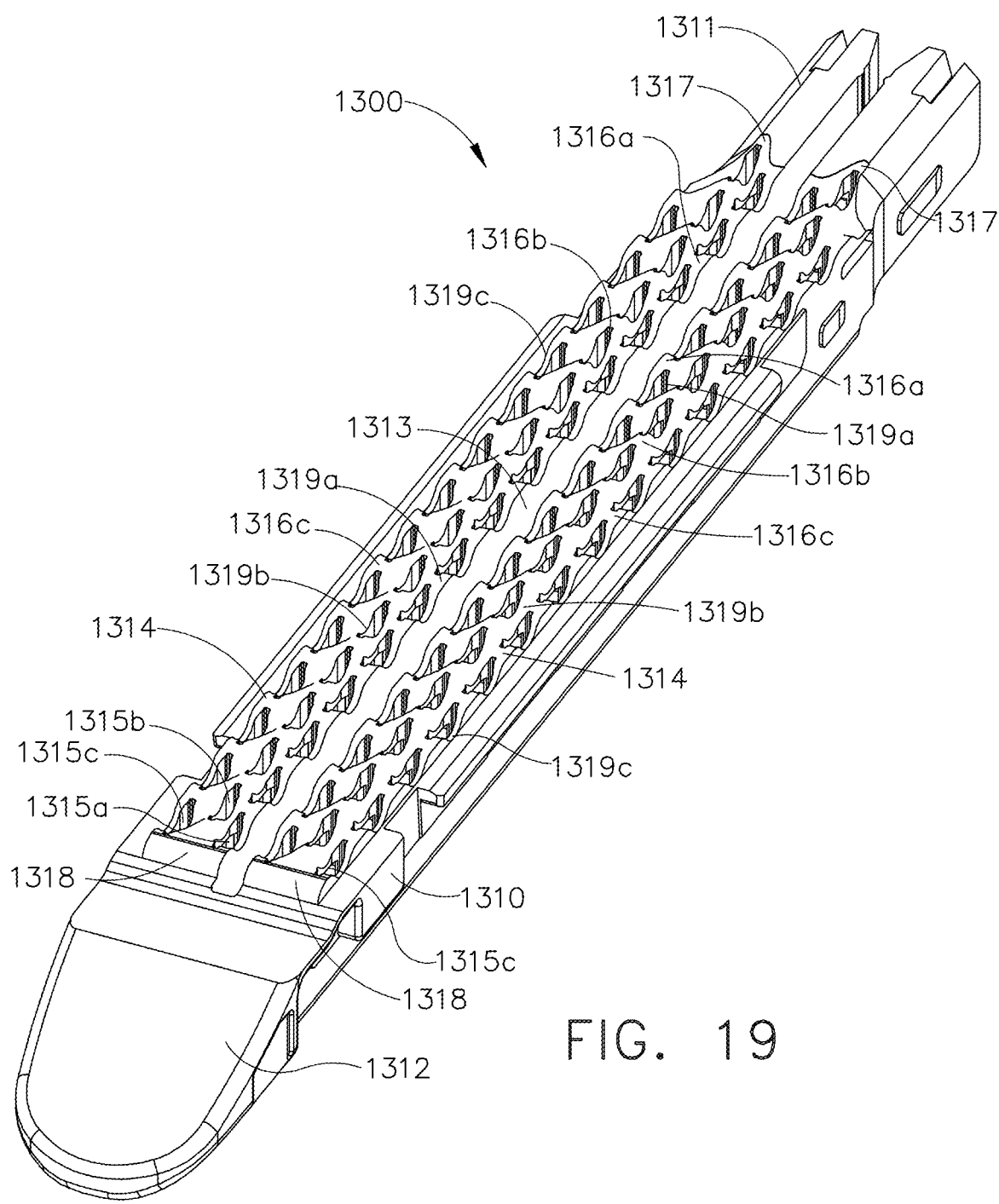
FIG. 19 is a perspective view of a staple cartridge in accordance with at least one embodiment comprising a wavy deck surface.
Figure 20:
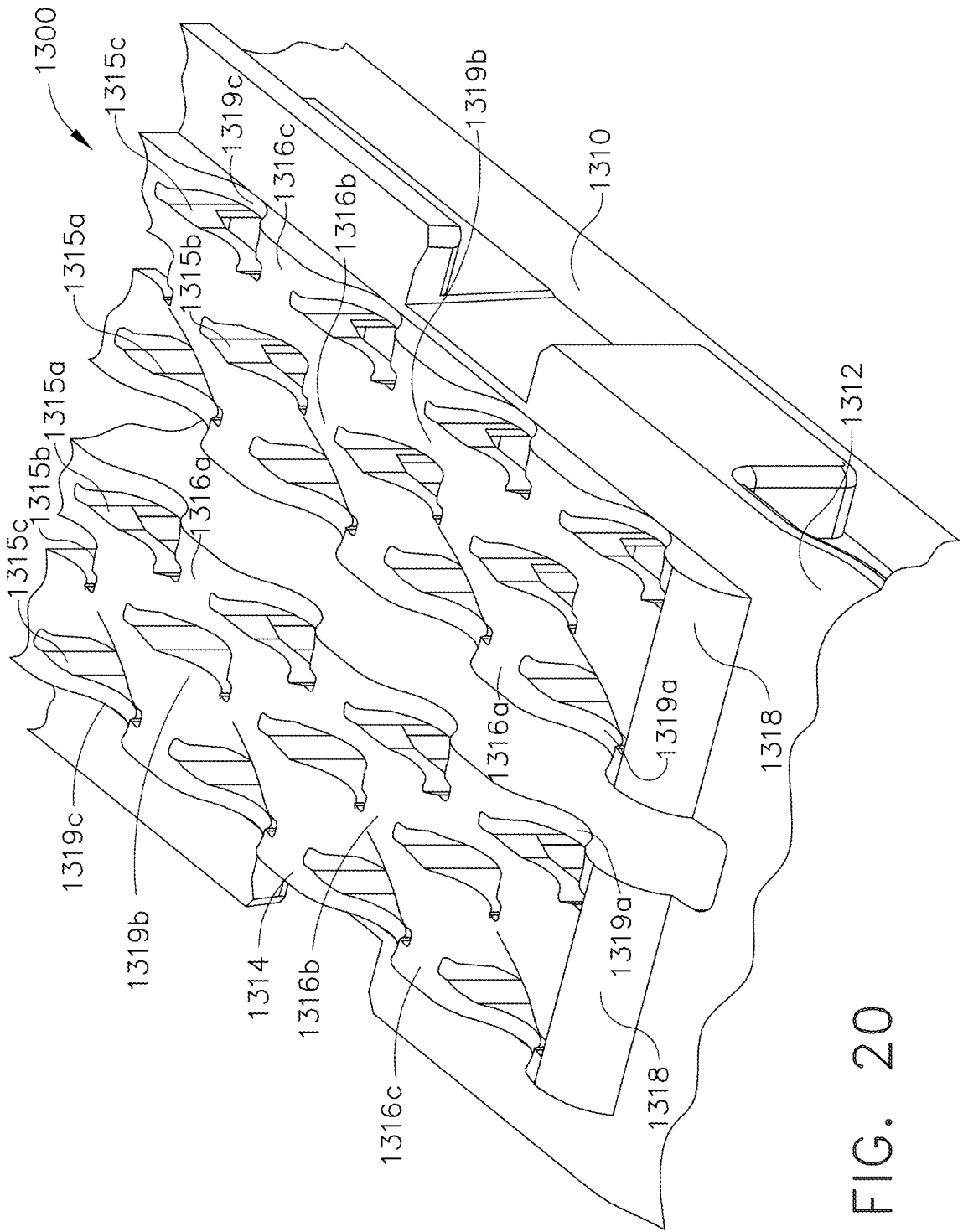
FIG. 20 is a detail view of the deck surface of the staple cartridge of FIG. 19.

A staple cartridge assembly 1200 is depicted in FIGS. 13-18A. The staple cartridge assembly 1200 comprises a cartridge body 1210 and a layer 1220 (FIG. 18A). The cartridge body 1210 comprises a proximal end 1211 and a distal end 1212. The cartridge body 1210 further comprises a longitudinal slot 1213 defined therein which is configured to receive at least a portion of a firing member therein. The slot 1213 extends from the proximal end 1211 toward the distal end 1212. The cartridge body 1210 further comprises a plurality of staple cavities defined therein. The staple cavities are arranged in three longitudinal rows on a first side of the longitudinal slot 1213 and three longitudinal rows on a second side of the longitudinal slot 1213. On each side of the longitudinal slot 1213, a first longitudinal row of staple cavities 1215a extends alongside the longitudinal slot 1213, a second row of staple cavities 1215b extends alongside the first row of staple cavities 1215a, and a third row of staple cavities 1215c extends alongside the second row of staple cavities 1215b. The first row of staple cavities 1215a, the second row of staple cavities 1215b, and the third row of staple cavities 1215c are parallel to one another and the longitudinal slot 1213; however, embodiments are envisioned in which the first row of staple cavities 1215a, the second row of staple cavities 1215b, and/or the third row of staple cavities 1215c are not parallel to one another and/or the longitudinal slot 1213. Further to the above, the firing member can be configured to lift staple drivers positioned within the cartridge body 1210 to eject staples removably stored in the staple cavities 1215a, 1215b, and 1215c as the firing member is moved toward the distal end 1212 of the staple cartridge 1200.

The first staple cavities 1215a are positioned at regular intervals along a first longitudinal axis. Spaces between adjacent first staple cavities 1215a can be referred to as staple gaps in the first longitudinal row as tissue positioned over such spaces will not be stapled by staples ejected from the first staple cavities 1215a. The second staple cavities 1215b are also positioned at regular intervals along a second longitudinal axis. The second staple cavities 1215b are staggered with respect to the first staple cavities 1215a. The second staple cavities 1215b are positioned laterally with respect to the staple gaps in the first row of staple cavities 1215a. Spaces between adjacent second staple cavities 1215b can also be referred to as staple gaps in the second longitudinal row as tissue positioned over such spaces will not be stapled by staples ejected from the second staple cavities 1215b. The third staple cavities 1215c are also positioned at regular intervals along a third longitudinal axis. The third staple cavities 1215c are staggered with respect to the second staple cavities 1215b. The third staple cavities 1215c are positioned laterally with respect to the staple gaps in the second row of staple cavities 1215b.

The staple cartridge body 1210 further comprises a tissue-supporting deck 1214. The deck 1214 comprises a plurality of depressions, or wells, defined therein. A first well 1219a surrounds each first staple cavity 1215a. Each first well 1219a is defined by a substantially triangular wall 1216a comprising a vertex pointing proximally, a vertex pointing distally, and a vertex pointing laterally outwardly. Each first well 1219a comprises a first floor 1214a which is a first depth from the deck 1214. A second well 1219b surrounds each second staple cavity 1215b. Each second well 1219b is defined by a wall 1216b which is substantially diamond-shaped comprising a vertex pointing proximally, a vertex pointing distally, a vertex pointing laterally inwardly, and a vertex pointing laterally outwardly. Each second well 1219b comprises a second floor 1214b which is a second depth from the deck 1214. A third well 1219c surrounds each third staple cavity 1215c. Each third well 1219c is defined by a substantially triangular wall 1216c comprising a vertex pointing proximally, a vertex pointing distally, and a vertex pointing laterally inwardly. Each third well 1219c comprises a third floor 1214c which is a third depth from the deck 1214.

The first wells 1219a are positioned at regular intervals along a first longitudinal axis. Gaps are present between adjacent first wells 1219a. The second wells 1219b are also positioned at regular intervals along a second longitudinal axis. The second wells 1219b are staggered with respect to the first wells 1219b. The second wells 1219b are positioned laterally with respect to the gaps in the first row of wells 1219a. Gaps are present between adjacent second wells 1219b. The third wells 1219c are also positioned at regular intervals along a third longitudinal axis. The third wells 1219c are staggered with respect to the second wells 1219b. The third wells 1219c are positioned laterally with respect to the gaps in the second row of wells 1219b.

Further to the above, the first depth of the first wells 1219a, the second depth of the second wells 1219b, and the third depth of the third wells 1219c can have the same depth. In other instances, the first depth, the second depth, and/or the third depth can be different.

The staple cartridge 1200 can be utilized with any suitable layer that can be implanted against the tissue being stapled. The layer can comprise an adjunct material which is positioned on the deck 1214 of the cartridge body 1210 before the staple cartridge 1200 is inserted into the patient. Such an adjunct material could comprise buttress material and/or a tissue thickness compensator, for example. In various instances, the layer can move relative to the deck 1214 when the staple cartridge 1200 and the layer are positioned relative to the tissue that is to be stapled.

Turning now to FIG. 18A, a layer 1220 comprises a bottom surface 1224 configured to contact and be supported by the deck 1214 of the cartridge body 1210. The layer 1220 further comprises projections 1229a, 1229b, and 1229c extending therefrom which are configured to be received in the wells 1219a, 1219b, and 1219c, respectively. The projections 1229a, 1229b, and 1229c can limit relative motion between the layer 1220 and the cartridge body 1210. The projections 1229a, 1229b, and 1229c are closely received in the wells 1219a, 1219b, and 1219c, respectively, and, as a result, the projections 1229a, 1229b, and 1229c can abut the sidewalls of the wells 1219a, 1219b, and 1219c to limit lateral and longitudinal movement of the layer 1220. The projections 1229a, 1229b, and 1229c can be sized and configured such that they are compressed, or wedged, within the wells 1219a, 1219b, and 1219c, respectively. Such compression, or wedging, can not only limit the lateral and longitudinal movement of the layer 1220, it can also limit unintentional vertical movement of the layer 1220 away from the deck 1214. As the reader will appreciate, the lateral and longitudinal compression, or wedging, is sufficient to hold the layer 1220 in position yet, at the same, it can be overcome to permit the layer 1220 to be separated from the cartridge body 1210 after the staples have been fired and the layer 1220 has been implanted against the tissue.

The layer 1220 is closely received between a proximal wall 1217 and a distal wall 1218 and, as a result, the layer 1220 can abut the proximal wall 1217 and/or the distal wall 1218 to limit longitudinal movement of the layer 1220. The layer 1220 comprises a proximal end wall 1227 configured to engage the proximal wall 1217 and a distal end wall 1228 configured to engage the distal wall 1218. The layer 1220 can be sized and configured such that it is compressed, or wedged, between the proximal wall 1217 and the distal wall 1218. Such compression, or wedging, can not only limit the longitudinal movement of the layer 1220, it can also limit unintentional vertical movement of the layer 1220 away from the deck 1214. As the reader will appreciate, the longitudinal compression, or wedging, is sufficient to hold the layer 1220 in position yet, at the same, it can be overcome to permit the layer 1220 to be separated from the cartridge body 1210 after the staples have been fired and the layer 1220 has been implanted against the tissue.

The projections 1229a, 1229b, and 1229c comprise a negative impression of the voids created by the wells 1219a, 1219b, and 1219c, respectively; however, the projections 1229a, 1229b, and 1229c can comprise any suitable configuration. The projections 1229a, 1229b, and 1229c are defined by contours which cause the projections 1229a, 1229b, and 1229c to fit snugly within the wells 1219a, 1219b, and 1219c, respectively. The projections 1229a, 1229b, and 1229c can be larger than the wells 1219a, 1219b, and 1219c, respectively, such that the projections 1229a, 1229b, and 1229c are compressed when they are positioned in the wells 1219a, 1219b, and 1219c. Such an arrangement can generate a biasing and/or retention force between the layer 1220 and the cartridge body 1210.

Each staple cavity 1215a, 1215b, and 1215c is configured to removably store a staple therein. In various instances, the staples stored in the staple cavities 1215a, 1215b, and 1215c have the same unformed height. In certain instances, such staples can be deformed to the same formed height. In other instances, such staples can be deformed to different formed heights. For example, the staples ejected from the first staple cavities 1215a can be deformed to a first deformed height, the staples ejected from the second staple cavities 1215b can be deformed to a second deformed height, and the staples ejected from the third staple cavities 1215c can be deformed to a third deformed height. The first deformed height can be shorter than the second deformed height and the second deformed height can be shorter than the third deformed height. Such an arrangement can provide a tissue compression gradient with respect to an incision made in the tissue. In various instances, the staples stored in the staple cavities 1215a, 1215b, and 1215c can have different unformed heights. For example, the staples ejected from the first staple cavities 1215a can have a first unformed height, the staples ejected from the second staple cavities 1215b can have a second unformed height, and the staples ejected from the third staple cavities 1215c can have a third unformed height. The first unformed height can be shorter than the second unformed height and the second unformed height can be shorter than the third unformed height.

Figure 26A:
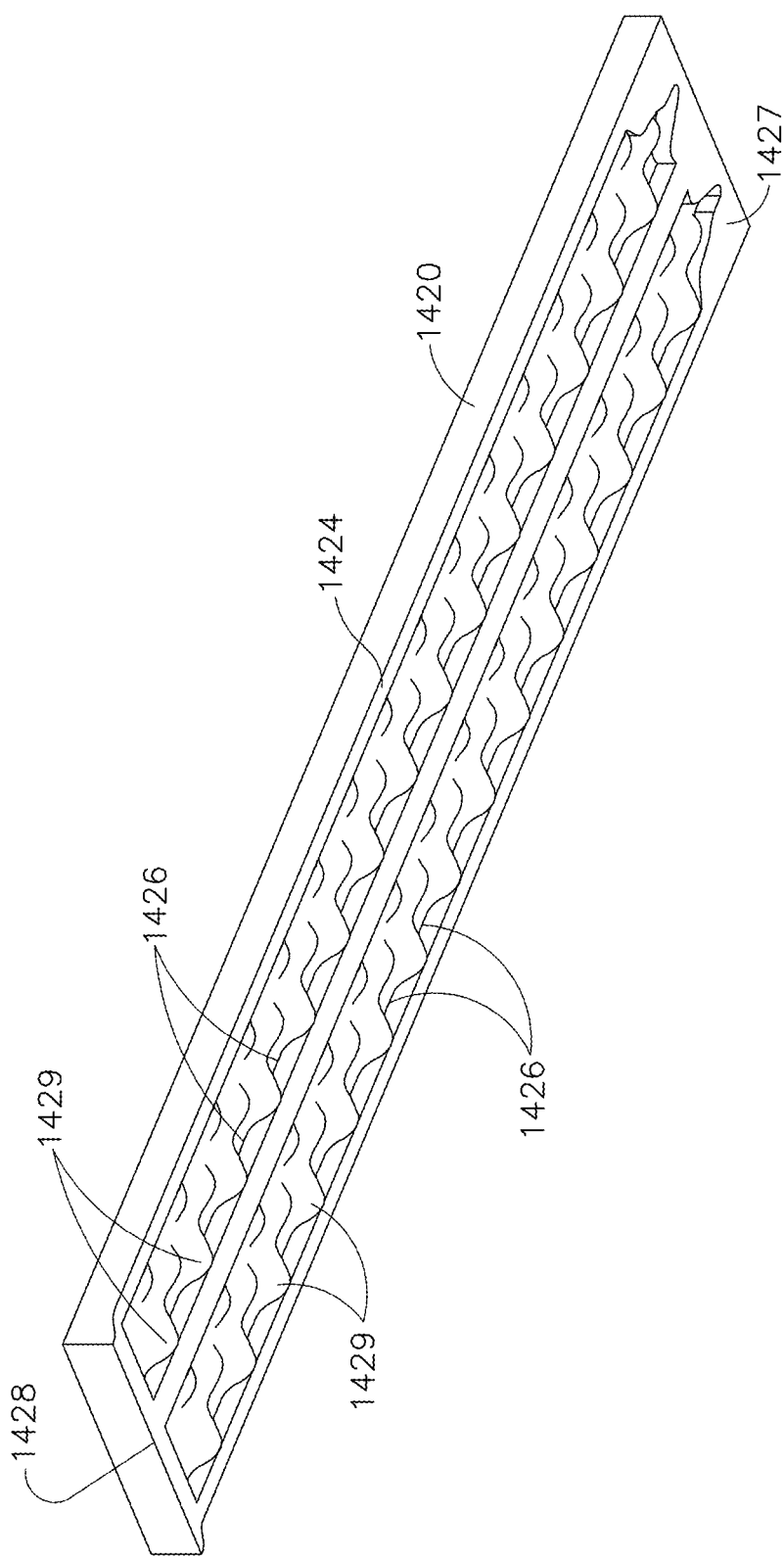
FIG. 26A is a perspective view of a layer usable with the staple cartridge of FIG. 23.
Figure 27:
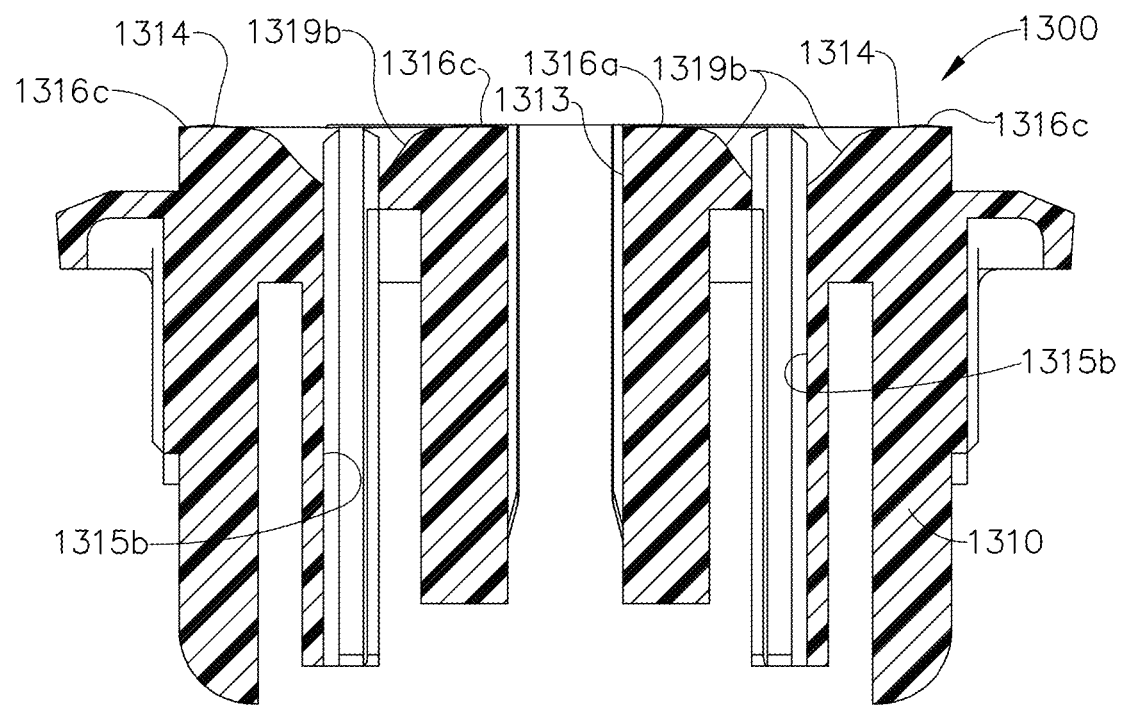
FIG. 27 is a cross-sectional view of the staple cartridge of FIG. 19 taken along line 27-27 in FIG. 21.
Figure 28:
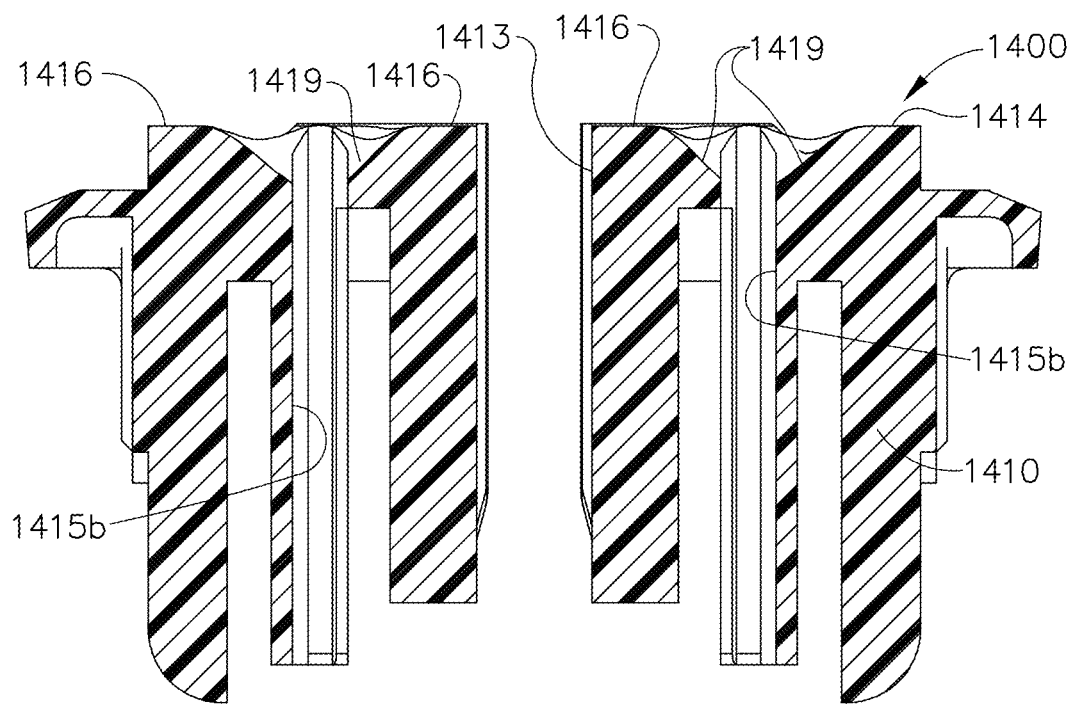
FIG. 28 is a cross-sectional view of the staple cartridge of FIG. 23 taken along line 28-28 in FIG. 25.
Figure 29:
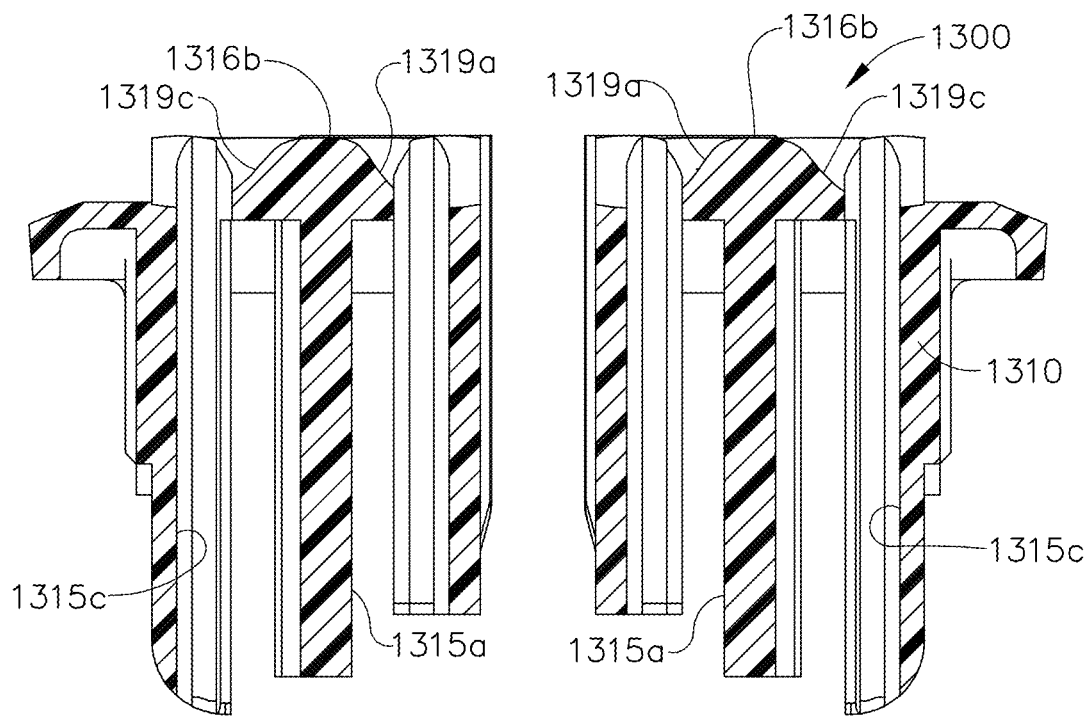
FIG. 29 is a cross-sectional view of the staple cartridge of FIG. 19 taken along line 29-29 in FIG. 21.
Figure 30:
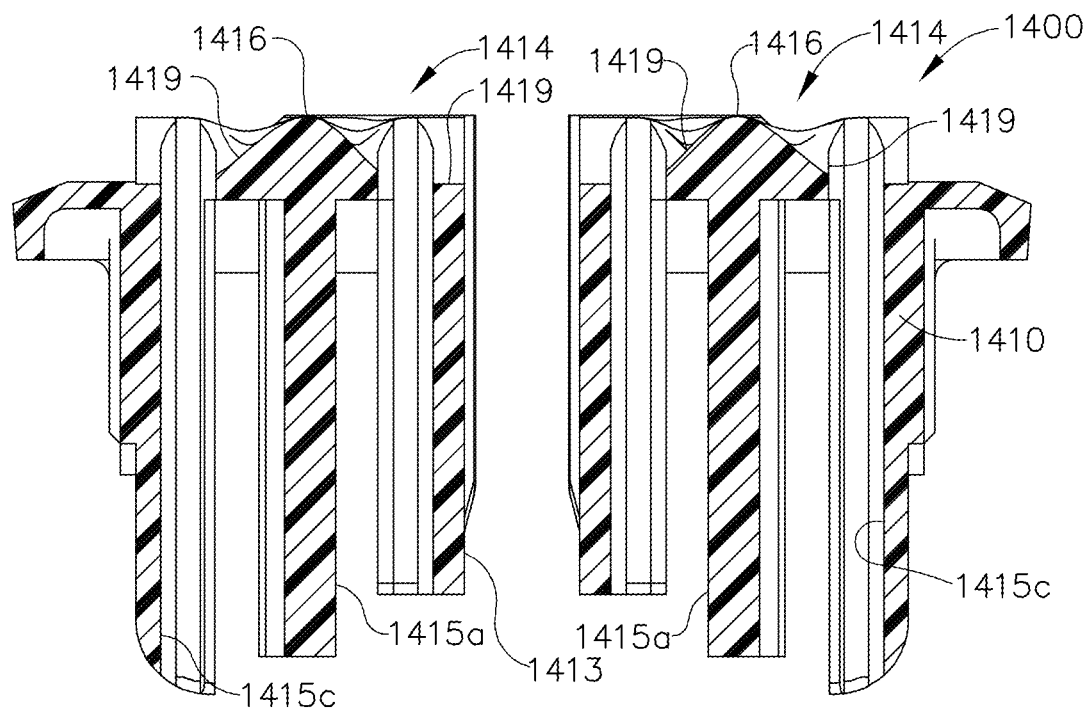
FIG. 30 is a cross-sectional view of the staple cartridge of FIG. 23 taken along line 30-30 in FIG. 25.
Figure 31:
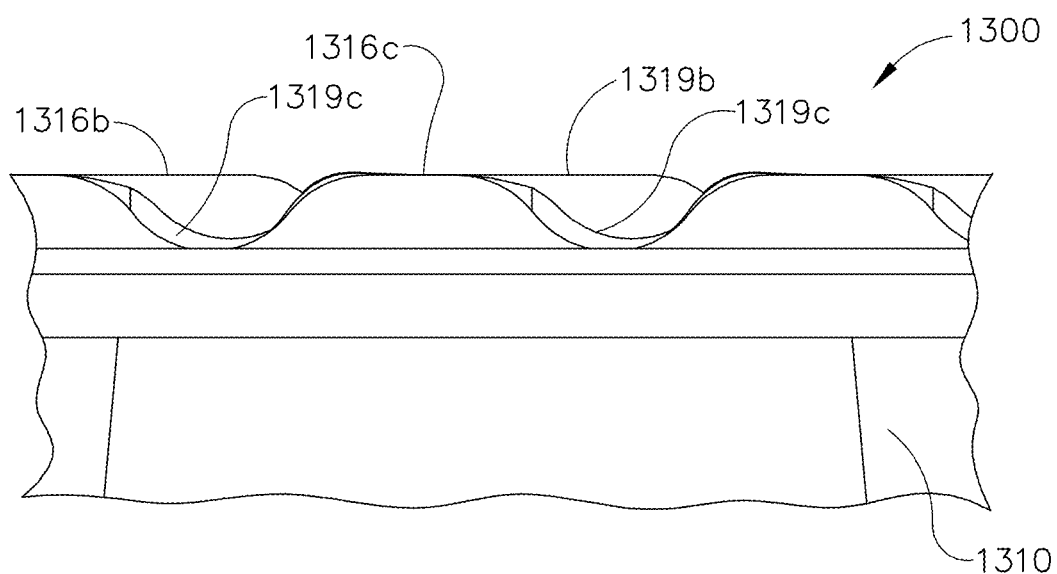
FIG. 31 is a detail view of the wavy deck surface of the cartridge of FIG. 19.
Figure 32:
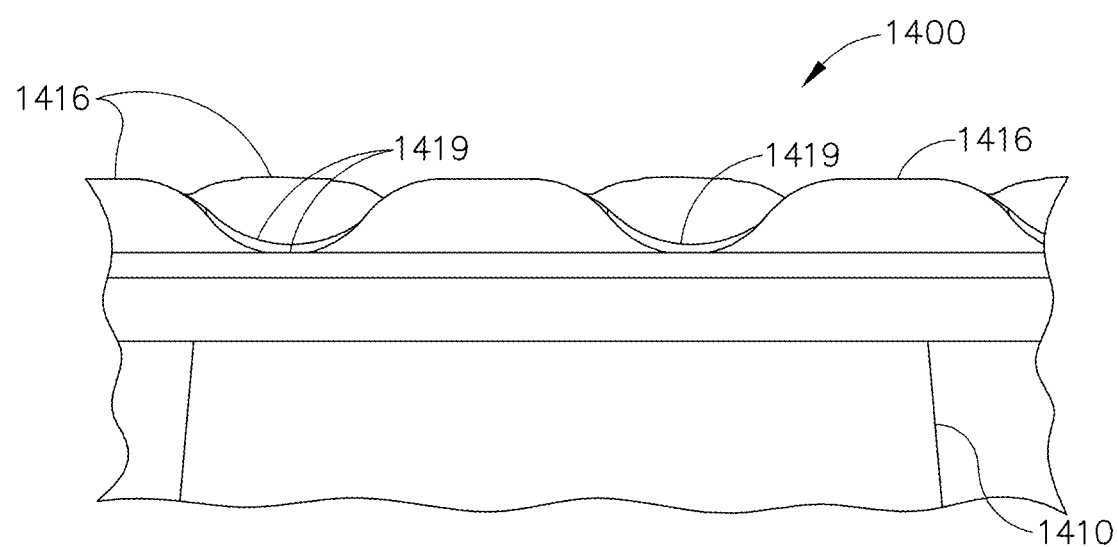
FIG. 32 is a detail view of the wavy deck surface of the cartridge of FIG. 23.

A staple cartridge assembly 1400 is depicted in FIGS. 23-26A, 28, 30, and 32. The staple cartridge assembly 1400 comprises a cartridge body 1410 and a layer 1420 (FIG. 26A). The cartridge body 1410 comprises a proximal end 1411 and a distal end 1412. The cartridge body 1410 further comprises a longitudinal slot 1413 defined therein which is configured to receive at least a portion of a firing member therein. The slot 1413 extends from the proximal end 1411 toward the distal end 1412. The cartridge body 1410 further comprises a plurality of staple cavities defined therein. The staple cavities are arranged in three longitudinal rows on a first side of the longitudinal slot 1413 and three longitudinal rows on a second side of the longitudinal slot 1413. On each side of the longitudinal slot 1413, a first longitudinal row of staple cavities 1415a extends alongside the longitudinal slot 1413, a second row of staple cavities 1415b extends alongside the first row of staple cavities 1415a, and a third row of staple cavities 1415c extends alongside the second row of staple cavities 1415b. The first row of staple cavities 1415a, the second row of staple cavities 1415b, and the third row of staple cavities 1415c are parallel to one another and the longitudinal slot 1413; however, embodiments are envisioned in which the first row of staple cavities 1415a, the second row of staple cavities 1415b, and/or the third row of staple cavities 1415c are not parallel to one another and/or the longitudinal slot 1413. Further to the above, the firing member can be configured to lift staple drivers positioned within the cartridge body 1410 to eject staples removably stored in the staple cavities 1415a, 1415b, and 1415c as the firing member is moved toward the distal end 1412 of the staple cartridge 1400.

The first staple cavities 1415a are positioned at regular intervals along a first longitudinal axis. Spaces between adjacent first staple cavities 1415a can be referred to as staple gaps in the first longitudinal row as tissue positioned over such spaces will not be stapled by staples ejected from the first staple cavities 1415a. The second staple cavities 1415b are also positioned at regular intervals along a second longitudinal axis. The second staple cavities 1415b are staggered with respect to the first staple cavities 1415a. The second staple cavities 1415b are positioned laterally with respect to the staple gaps in the first row of staple cavities 1415a. Spaces between adjacent second staple cavities 1415b can also be referred to as staple gaps in the second longitudinal row as tissue positioned over such spaces will not be stapled by staples ejected from the second staple cavities 1415b. The third staple cavities 1415c are also positioned at regular intervals along a third longitudinal axis. The third staple cavities 1415c are staggered with respect to the second staple cavities 1415b. The third staple cavities 1415c are positioned laterally with respect to the staple gaps in the second row of staple cavities 1415b.

The staple cartridge body 1410 further comprises a tissue-supporting deck 1414. The deck 1414 comprises a plurality of peaks 1416 and valleys 1419 defined therein. The valleys 1419 are aligned with the first staple cavities 1415a, the second staple cavities 1415b, and the third staple cavities 1415c. The peaks 1416 are aligned with the gaps between the first staple cavities 1415a. The peaks 1416 are also aligned with the gaps between the second staple cavities 1415b. Similarly, the peaks 1416 are aligned with the gaps between the third staple cavities 1415c. The peaks 1416 in the first row of staple cavities 1415a can be connected to the peaks 1416 in the second row of staple cavities 1415b. Similarly, the peaks 1416 in the second row of staple cavities 1415b can be connected to the peaks 1416 in the third row of staple cavities 1415c. The wells 1419 each have the same depth; however, other embodiments are envisioned in which the wells have different depths. For instance, the wells aligned with the first staple cavities 1415a can have a first depth, the wells aligned with the second staple cavities 1415b can have a second depth, and the wells aligned with the third staple cavities 1415c can have a third depth, wherein the first depth, the second depth, and/or the third depth can be different. The peaks 1416 each have the same height; however, other embodiments are envisioned in which the peaks have different heights. For instance, the peaks positioned between the first staple cavities 1415a can have a first height, the peaks positioned between the second staple cavities 1415b can have a second height, and the peaks positioned between the third staple cavities 1415c can have a third height, wherein the first height, the second height, and/or the third height can be different.

The staple cartridge 1400 can be utilized with any suitable layer that can be implanted against the tissue being stapled. The layer can comprise an adjunct material which is positioned on the deck 1414 of the cartridge body 1410 before the staple cartridge 1400 is inserted into the patient. Such an adjunct material could comprise buttress material and/or a tissue thickness compensator, for example. In various instances, the layer can move relative to the deck 1414 when the staple cartridge 1400 and the layer are positioned relative to the tissue that is to be stapled.

Turning now to FIG. 26A, a layer 1420 comprises a bottom surface 1424 configured to contact and be supported by the deck 1414 of the cartridge body 1410. The bottom surface 1424 comprises peaks 1429 extending therefrom which are configured to be received in the valleys 1419 defined in the deck 1414. The peaks 1429 can limit relative motion between the layer 1420 and the cartridge body 1410. The peaks 1429 are closely received within the valleys 1419 and, as a result, the peaks 1429 can abut the walls of the valleys 1419 to limit lateral and/or longitudinal movement of the layer 1420. The bottom surface 1424 further comprises valleys 1426 defined therein which are configured to receive peaks 1416 extending from the cartridge body 1410. The valleys 1426 can limit relative motion between the layer 1420 and the cartridge body 1410. The peaks 1416 are closely received within the valleys 1426 and, as a result, the peaks 1416 can abut the walls of the valleys 1426 to limit lateral and/or longitudinal movement of the layer 1420.

In addition to or in lieu of the above, the layer 1420 is closely received between a proximal wall 1417 and a distal wall 1418 of the cartridge body 1410 and, as a result, the layer 1420 can abut the proximal wall 1417 and/or the distal wall 1418 to limit longitudinal movement of the layer 1420. The layer 1420 comprises a proximal end wall 1427 configured to engage the proximal wall 1417 and a distal end wall 1428 configured to engage the distal wall 1418. The layer 1420 can be sized and configured such that it is compressed, or wedged, between the proximal wall 1417 and the distal wall 1418. Such compression, or wedging, can not only limit the longitudinal movement of the layer 1420, it can also limit unintentional vertical movement of the layer 1420 away from the deck 1414. The longitudinal compression, or wedging, is sufficient to hold the layer 1420 in position yet, at the same, it can be overcome to permit the layer 1420 to be separated from the cartridge body 1410 after the staples have been fired and the layer 1420 has been implanted against the tissue.

The valleys 1426 and the peaks 1429 comprise a negative impression of the peaks 1416 and the valleys 1419, respectively; however, the layer 1420 can comprise any suitable configuration. The valleys 1426 and the peaks 1429 are defined by contours which cause the valleys 1426 and the peaks 1429 to fit snugly within the peaks 1416 and the valleys 1419, respectively.

Each staple cavity 1415a, 1415b, and 1415c is configured to removably store a staple therein. In various instances, the staples stored in the staple cavities 1415a, 1415b, and 1415c have the same unformed height. In certain instances, such staples can be deformed to the same formed height. In other instances, such staples can be deformed to different formed heights. For example, the staples ejected from the first staple cavities 1415a can be deformed to a first deformed height, the staples ejected from the second staple cavities 1415b can be deformed to a second deformed height, and the staples ejected from the third staple cavities 1415c can be deformed to a third deformed height. The first deformed height can be shorter than the second deformed height and the second deformed height can be shorter than the third deformed height. Such an arrangement can provide a tissue compression gradient with respect to an incision made in the tissue. In various instances, the staples stored in the staple cavities 1415a, 1415b, and 1415c can have different unformed heights. For example, the staples ejected from the first staple cavities 1415a can have a first unformed height, the staples ejected from the second staple cavities 1415b can have a second unformed height, and the staples ejected from the third staple cavities 1415c can have a third unformed height. The first unformed height can be shorter than the second unformed height and the second unformed height can be shorter than the third unformed height.

Figure 22A:
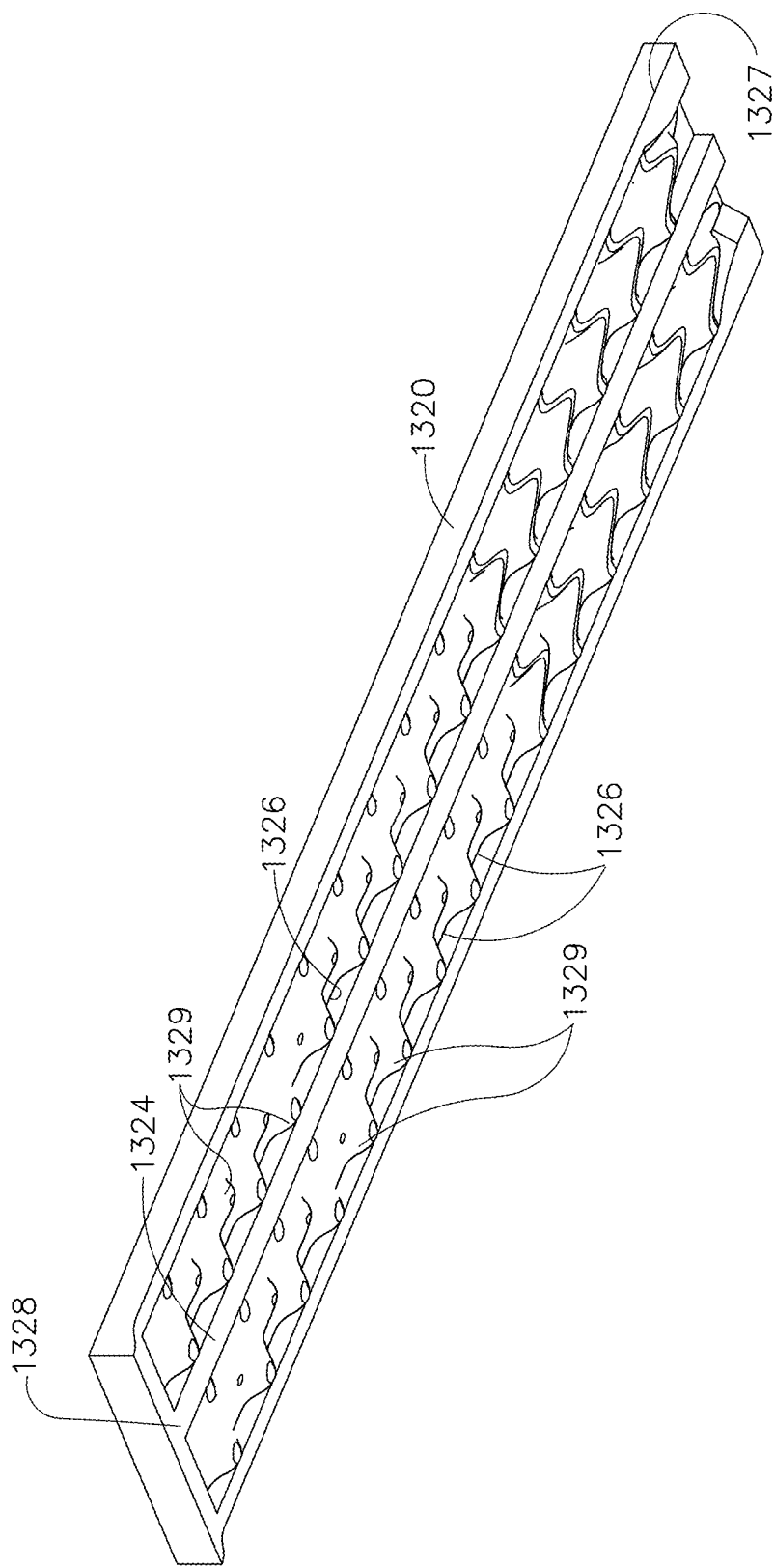
FIG. 22A is a perspective view of a layer usable with the staple cartridge of FIG. 19.
Figure 23:
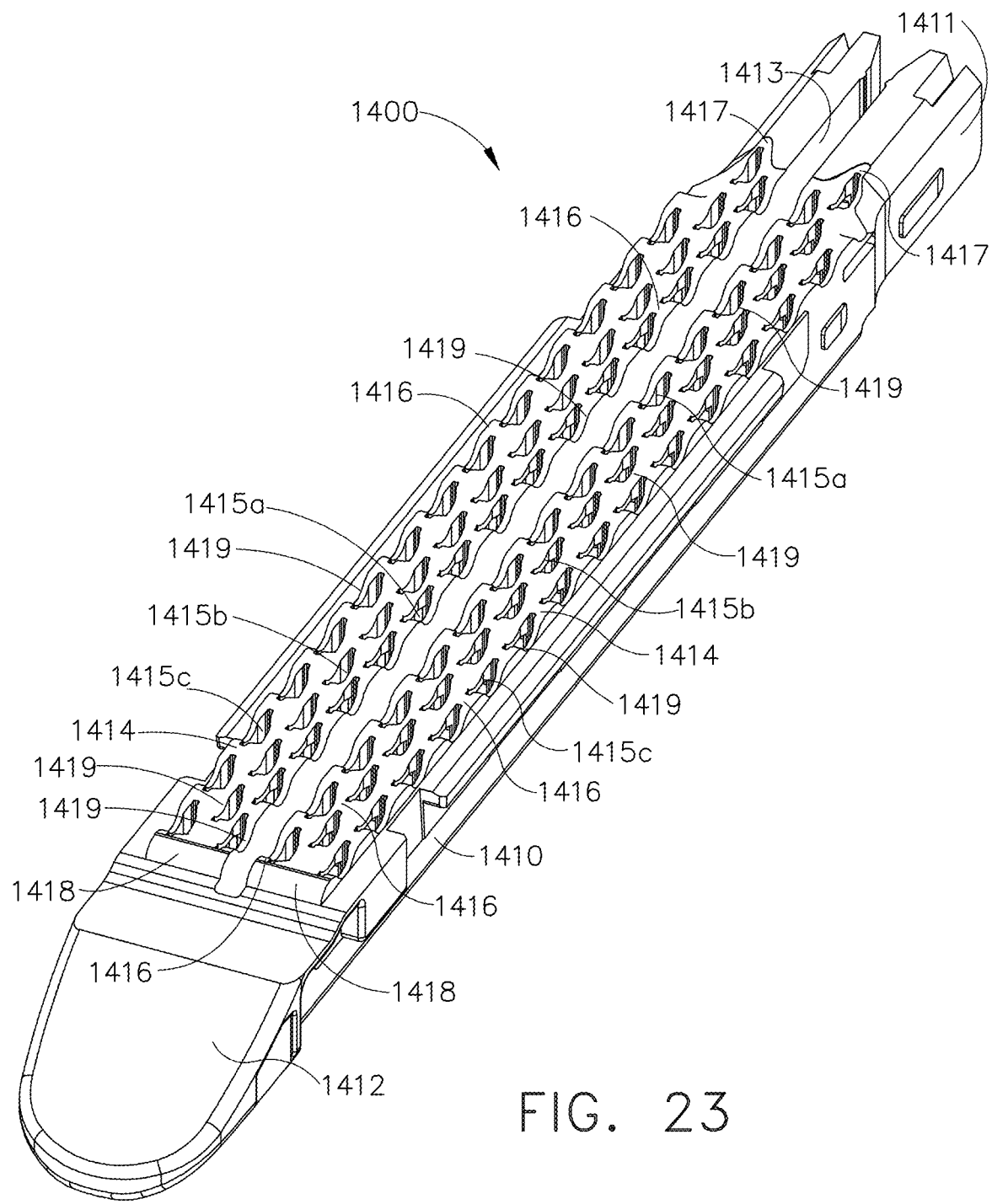
FIG. 23 is a perspective view of a staple cartridge in accordance with at least one embodiment comprising a wavy deck surface.
Figure 24:
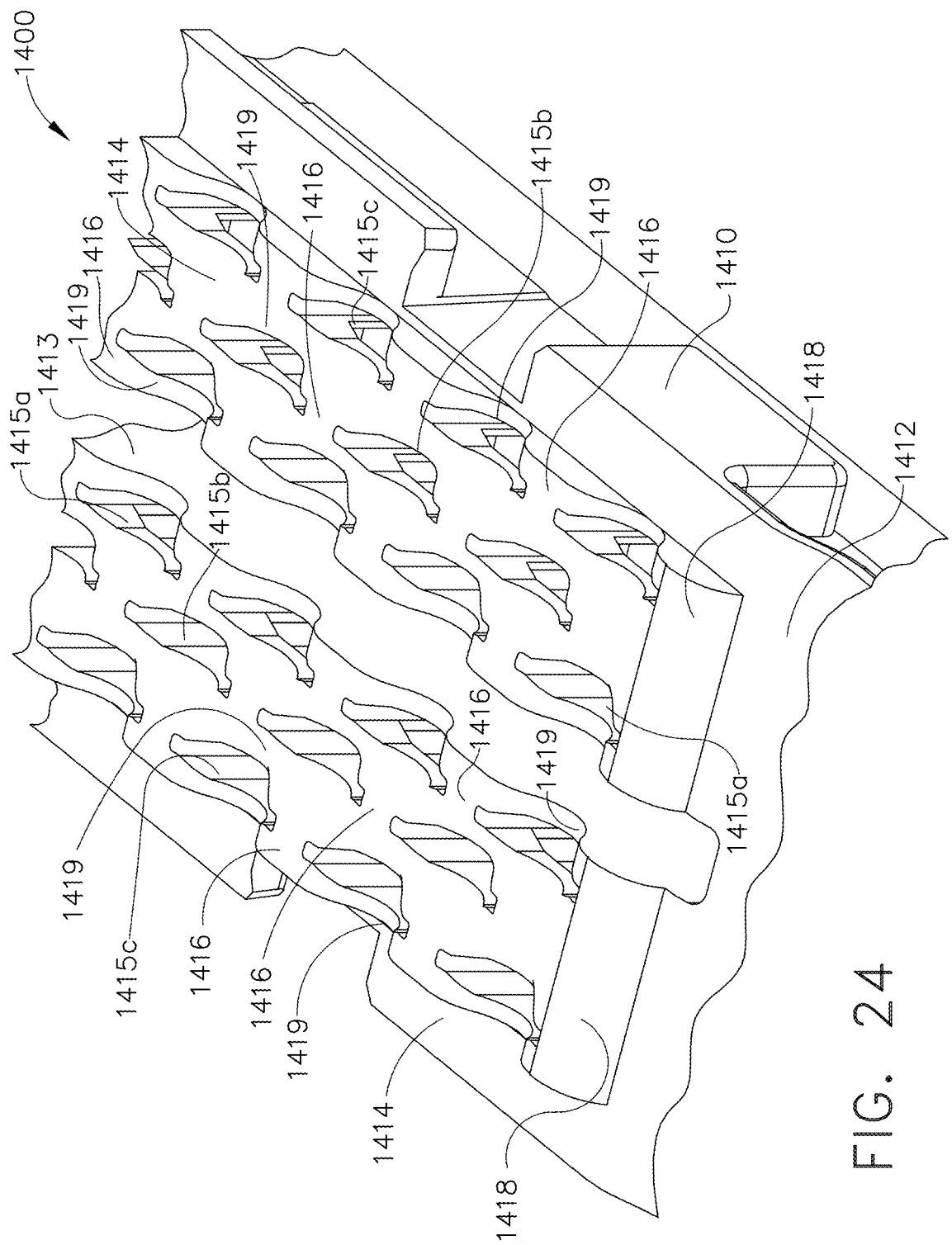
FIG. 24 is a detail view of the deck surface of the staple cartridge of FIG. 23.

A staple cartridge assembly 1300 is depicted in FIGS. 19-22A, 27, 29, and 31. The staple cartridge assembly 1300 comprises a cartridge body 1310 and a layer 1320 (FIG. 22A). The cartridge body 1310 comprises a proximal end 1311 and a distal end 1312. The cartridge body 1310 further comprises a longitudinal slot 1313 defined therein which is configured to receive at least a portion of a firing member therein. The slot 1313 extends from the proximal end 1311 toward the distal end 1312. The cartridge body 1310 further comprises a plurality of staple cavities defined therein. The staple cavities are arranged in three longitudinal rows on a first side of the longitudinal slot 1313 and three longitudinal rows on a second side of the longitudinal slot 1313. On each side of the longitudinal slot 1313, a first longitudinal row of staple cavities 1315a extends alongside the longitudinal slot 1313, a second row of staple cavities 1315b extends alongside the first row of staple cavities 1315a, and a third row of staple cavities 1315c extends alongside the second row of staple cavities 1315b. The first row of staple cavities 1315a, the second row of staple cavities 1315b, and the third row of staple cavities 1315c are parallel to one another and the longitudinal slot 1313; however, embodiments are envisioned in which the first row of staple cavities 1315a, the second row of staple cavities 1315b, and/or the third row of staple cavities 1315c are not parallel to one another and/or the longitudinal slot 1313. Further to the above, the firing member can be configured to lift staple drivers positioned within the cartridge body 1310 to eject staples removably stored in the staple cavities 1315a, 1315b, and 1315c as the firing member is moved toward the distal end 1312 of the staple cartridge 1300.

The first staple cavities 1315a are positioned at regular intervals along a first longitudinal axis. Spaces between adjacent first staple cavities 1315a can be referred to as staple gaps in the first longitudinal row as tissue positioned over such spaces will not be stapled by staples ejected from the first staple cavities 1315a. The second staple cavities 1315b are also positioned at regular intervals along a second longitudinal axis. The second staple cavities 1315b are staggered with respect to the first staple cavities 1315a. The second staple cavities 1315b are positioned laterally with respect to the staple gaps in the first row of staple cavities 1315a. Spaces between adjacent second staple cavities 1315b can also be referred to as staple gaps in the second longitudinal row as tissue positioned over such spaces will not be stapled by staples ejected from the second staple cavities 1315b. The third staple cavities 1315c are also positioned at regular intervals along a third longitudinal axis. The third staple cavities 1315c are staggered with respect to the second staple cavities 1315b. The third staple cavities 1315c are positioned laterally with respect to the staple gaps in the second row of staple cavities 1315b.

The staple cartridge body 1310 further comprises a tissue-supporting deck 1314. The deck 1314 comprises a plurality of peaks and valleys defined therein. Valleys 1319a are aligned with the first staple cavities 1315a, valleys 1319b are aligned with the second staple cavities 1315b, and valleys 1319c are aligned with the third staple cavities 1315c. Peaks 1316a are aligned with the gaps between the first staple cavities 1315a. Peaks 1316b are aligned with the gaps between the second staple cavities 1315b. Similarly, peaks 1316c are aligned with the gaps between the third staple cavities 1315c. The peaks 1316a in the first row of staple cavities 1315a can be connected to the peaks 1316b in the second row of staple cavities 1315b. Similarly, the peaks 1316b in the second row of staple cavities 1315b can be connected to the peaks 1316c in the third row of staple cavities 1315c. The wells 1319a, 1319b, and 1319c can each have the same depth; however, other embodiments are envisioned in which the wells 1319a, 1319b, and 1319c have different depths. For instance, the wells 1319a aligned with the first staple cavities 1315a can have a first depth, the wells 1319b aligned with the second staple cavities 1315b can have a second depth, and the wells 1319c aligned with the third staple cavities 1315c can have a third depth, wherein the first depth, the second depth, and/or the third depth can be different. The peaks 1316a positioned between the first staple cavities 1315a have a first height, the peaks 1316b positioned between the second staple cavities 1315b have a second height, and the peaks 1316c positioned between the third staple cavities 1315c have a third height, wherein the first height, the second height, and/or the third height can be different. The first height of the peaks 1316a is taller than the second height of the peaks 1316b and the third height of the peaks 1316c, for example. The second height of the peaks 1316b can be taller than the third height of the peaks 1316c, for example. Such an arrangement can apply a first pressure to the tissue positioned over the staple cavities 1315a, a second pressure to the tissue positioned over the staple cavities 1315b, and a third pressure to the tissue positioned over the staple cavities 1315c. The first pressure is greater than the second pressure and the second pressure is greater than the third pressure. Such a pressure gradient can push fluids away from the incision created by the knife passing through the longitudinal slot 1313.

The staple cartridge 1300 can be utilized with any suitable layer that can be implanted against the tissue being stapled. The layer can comprise an adjunct material which is positioned on the deck 1314 of the cartridge body 1310 before the staple cartridge 1300 is inserted into the patient. Such an adjunct material could comprise buttress material and/or a tissue thickness compensator, for example. In various instances, the layer can move relative to the deck 1314 when the staple cartridge 1300 and the layer are positioned relative to the tissue that is to be stapled.

Turning now to FIG. 22A, a layer 1320 comprises a bottom surface 1324 configured to contact and be supported by the deck 1314 of the cartridge body 1310. The bottom surface 1324 comprises peaks 1329 extending therefrom which are configured to be received in the valleys 1319a-1319c defined in the deck 1314. The peaks 1329 can limit relative motion between the layer 1320 and the cartridge body 1310. The peaks 1329 are closely received within the valleys 1319a-1319c and, as a result, the peaks 1329 can abut the walls of the valleys 1319a-1319c to limit lateral and/or longitudinal movement of the layer 1320. The bottom surface 1324 further comprises valleys 1326 defined therein which are configured to receive peaks 1316a-1316c extending from the cartridge body 1310. The valleys 1326 can limit relative motion between the layer 1320 and the cartridge body 1310. The peaks 1316a-1316c are closely received within the valleys 1326 and, as a result, the peaks 1316a-1316c can abut the walls of the valleys 1326 to limit lateral and/or longitudinal movement of the layer 1320.

In addition to or in lieu of the above, the layer 1320 is closely received between a proximal wall 1317 and a distal wall 1318 of the cartridge body 1310 and, as a result, the layer 1320 can abut the proximal wall 1317 and/or the distal wall 1318 to limit longitudinal movement of the layer 1320. The layer 1320 comprises a proximal end wall 1327 configured to engage the proximal wall 1317 and a distal end wall 1328 configured to engage the distal wall 1318. The layer 1320 can be sized and configured such that it is compressed, or wedged, between the proximal wall 1317 and the distal wall 1318. Such compression, or wedging, can not only limit the longitudinal movement of the layer 1320, it can also limit unintentional vertical movement of the layer 1320 away from the deck 1314. The longitudinal compression, or wedging, is sufficient to hold the layer 1320 in position yet, at the same, it can be overcome to permit the layer 1320 to be separated from the cartridge body 1310 after the staples have been fired and the layer 1320 has been implanted against the tissue.

The valleys 1326 and the peaks 1329 comprise a negative impression of the peaks 1316a-1316c and the valleys 1319a-1319c, respectively; however, the layer 1320 can comprise any suitable configuration. The valleys 1326 and the peaks 1329 are defined by contours which cause the valleys 1326 and the peaks 1329 to fit snugly within the peaks 1316a-1316c and the valleys 1319a-1319c, respectively.

Each staple cavity 1315a, 1315b, and 1315c is configured to removably store a staple therein. In various instances, the staples stored in the staple cavities 1315a, 1315b, and 1315c have the same unformed height. In certain instances, such staples can be deformed to the same formed height. In other instances, such staples can be deformed to different formed heights. For example, the staples ejected from the first staple cavities 1315a can be deformed to a first deformed height, the staples ejected from the second staple cavities 1315b can be deformed to a second deformed height, and the staples ejected from the third staple cavities 1315c can be deformed to a third deformed height. The first deformed height can be shorter than the second deformed height and the second deformed height can be shorter than the third deformed height. Such an arrangement can provide a tissue compression gradient with respect to an incision made in the tissue. In various instances, the staples stored in the staple cavities 1315a, 1315b, and 1315c can have different unformed heights. For example, the staples ejected from the first staple cavities 1315a can have a first unformed height, the staples ejected from the second staple cavities 1315b can have a second unformed height, and the staples ejected from the third staple cavities 1315c can have a third unformed height. The first unformed height can be shorter than the second unformed height and the second unformed height can be shorter than the third unformed height.

Figure 33:
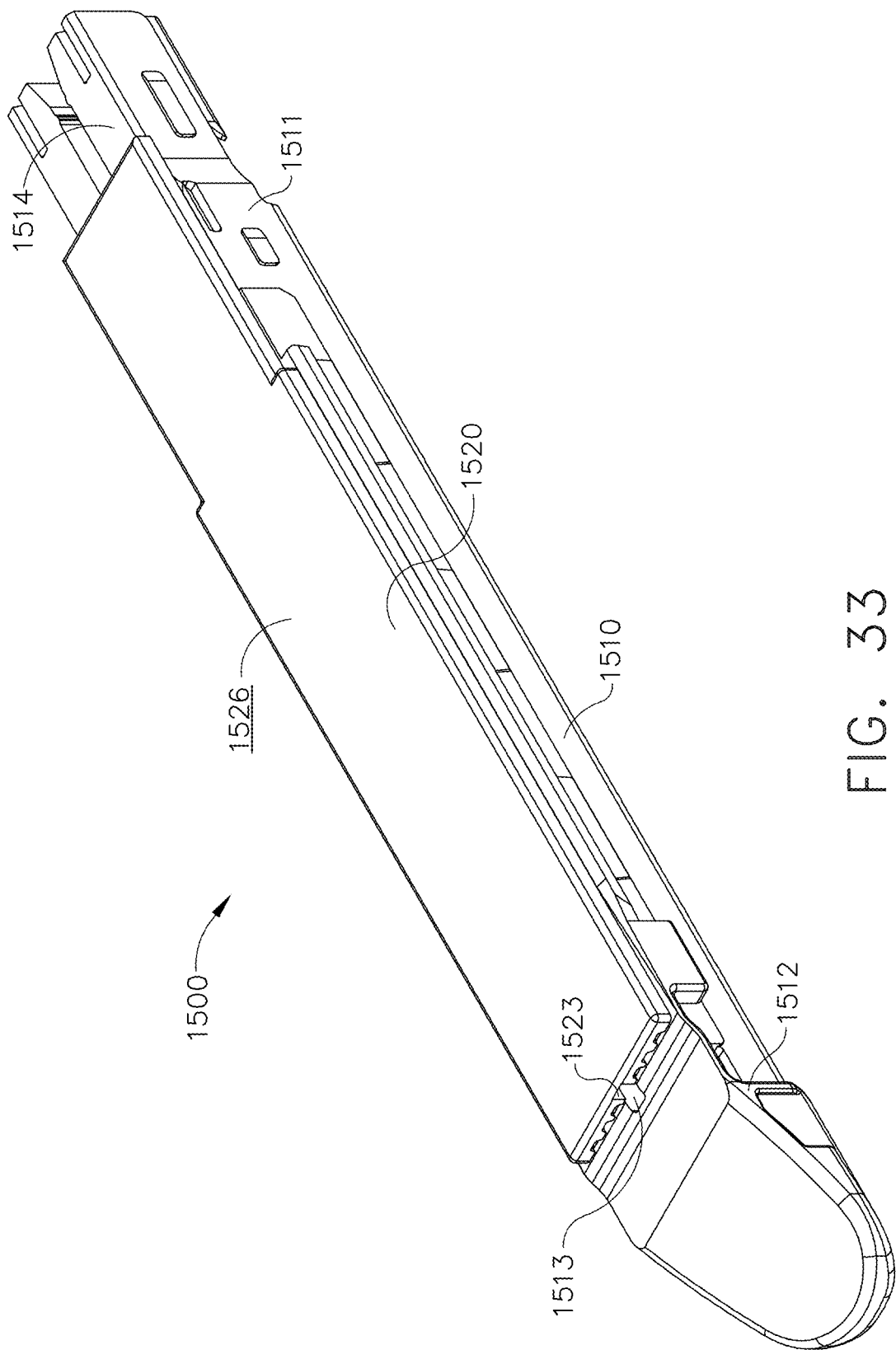
FIG. 33 is a perspective view of a staple cartridge in accordance with at least one embodiment comprising a cartridge body and a layer.
Figure 34:
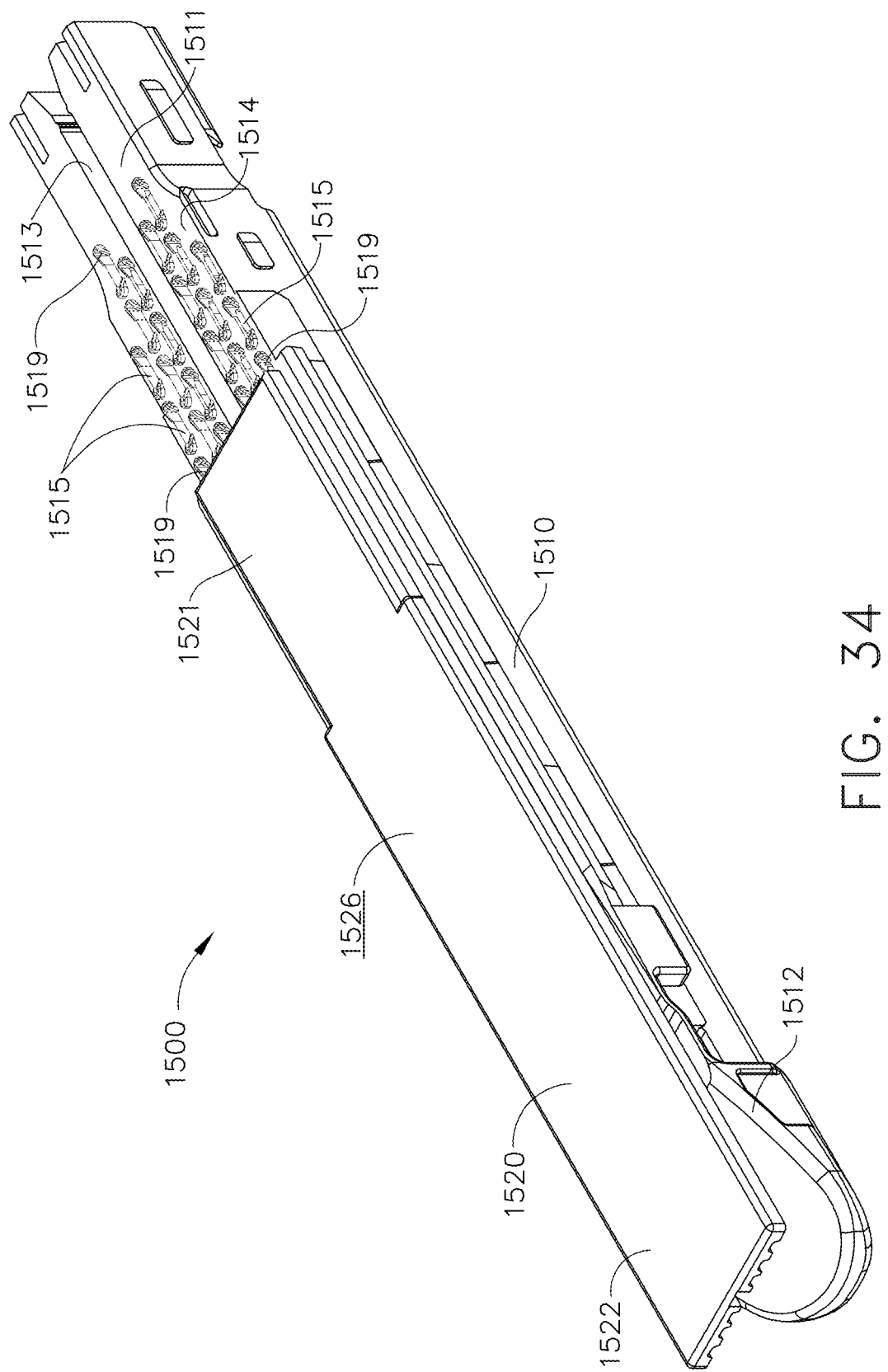
FIG. 34 is a perspective view of the staple cartridge of FIG. 33 illustrating the layer slid relative to the cartridge body.
Figure 35:
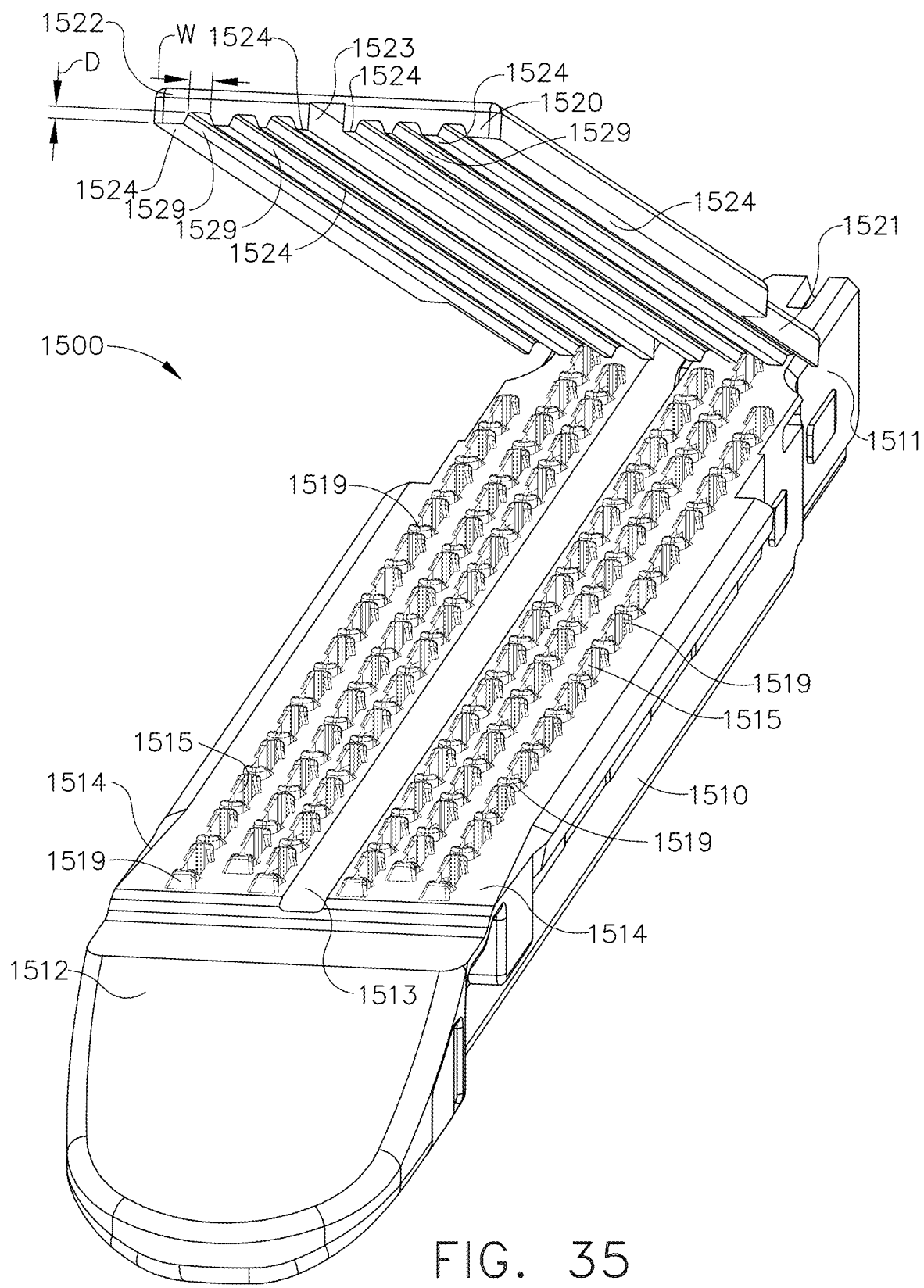
FIG. 35 is a perspective view of the staple cartridge of FIG. 33 illustrating the layer lifted away from the cartridge body.

A staple cartridge assembly 1500 is depicted in FIGS. 33-35. The staple cartridge assembly 1500 comprises a cartridge body 1510 and a layer 1520. The cartridge body 1510 comprises a proximal end 1511 and a distal end 1512. The cartridge body 1510 further comprises a longitudinal slot 1513 defined therein which is configured to receive at least a portion of a firing member therein. The slot 1513 extends from the proximal end 1511 toward the distal end 1512. The cartridge body 1510 further comprises a plurality of staple cavities 1515 defined in a deck 1514 of the cartridge body 1510. The staple cavities 1515 are arranged in three longitudinal rows on a first side of the longitudinal slot 1513 and three longitudinal rows on a second side of the longitudinal slot 1513. Further to the above, the firing member can be configured to lift staple drivers positioned within the cartridge body 1510 to eject staples removably stored in the staple cavities 1515 as the firing member is moved toward the distal end 1512 of the staple cartridge 1500.

The cartridge body 1510 further comprises projections 1519 which extend upwardly from the deck 1514. The projections 1519 extend the staple cavities 1515 above the deck 1514. The projections 1519 can support the staples stored in the staple cavities 1515 before, during, and/or after they are lifted toward the anvil by the staple drivers. The projections 1519 can guide the staples as the staples are lifted toward the anvil. A projection 1519 can be positioned at a proximal end of a staple cavity 1515, at a distal end of a staple cavity 1515, and/or at both ends of a staple cavity 1515. All of the staple cavities 1515 depicted in FIGS. 33-35 are surrounded at both ends by a projection 1519; however, other embodiments are envisioned in which some of the staple cavities 1515 are surrounded by two projections, one projection, and/or no projections.

The projections 1519 are arranged in longitudinal rows corresponding with the longitudinal rows of staple cavities 1515. Various embodiments are envisioned in which the cartridge body 1510 comprises an equal number of rows of projections 1519 and rows of staple cavities 1515. For example, six rows of projections 1519 are aligned with six rows of staple cavities 1515. Other embodiments are envisioned in which the cartridge body 1510 comprises more rows of staple cavities 1515 than rows of projections 1519. For example, a row of projections 1519 may be aligned with each of the innermost rows of staple cavities 1515 while the outermost rows of staple cavities 1515 may not have rows of projections aligned therewith. Certain embodiments are envisioned in which a projection, or a row of projections, is laterally offset with respect to a staple cavity, or a row of staple cavities.

Referring again to FIGS. 33-35, the layer 1520 comprises a proximal end 1521 positioned adjacent the proximal end 1511 of the cartridge body 1510 and, in addition, a distal end 1522 positioned adjacent the distal end 1511 of the cartridge body 1510. The layer 1520 further comprises a bottom surface 1524 configured to contact and be supported by the deck 1514 of the cartridge body 1510 and, in addition, a tissue-contacting surface 1526 positioned on the opposite side thereof. The tissue-contacting surface 1526 comprises a flat surface; however, other embodiments are envisioned in which the tissue-contacting surface comprises a textured and/or gripping surface configured to reduce undesired relative sliding motion between the tissue and the layer 1520. The layer 1520 further comprises a longitudinal slot 1523 aligned, or alignable, with the slot 1513 defined in the cartridge body 1510. The slot 1523 defines a portion of the layer 1520 which comprises a reduced cross-sectional thickness of the layer 1520 that is incised by a cutting member of the firing member than passes through the slot 1513 of the cartridge body 1510. The reduction in cross-section provided by the slot 1523 facilitates the transection of the layer 1520.

The layer 1520 comprises a plurality of longitudinal slots 1529 defined therein. The slots 1529 are defined in the bottom surface 1524 and are aligned with the rows of projections 1519. The slots 1529 are also aligned with the staple cavities 1515. The layer 1520 comprises six slots 1529 aligned with the six rows of projections 1519 and the six rows of staple cavities 1515, for example. When staples are ejected from the staple cavities 1515, the staples can enter the slots 1529 and pierce the layer 1520. When the staples are deformed by an anvil, the staples can capture the portions of the layer 1520 that include the longitudinal slots 1529 therein. Each slot 1529 can extend between the proximal end 1521 and the distal end 1522 of the layer 1520; however, other embodiments are envisioned in which the slots 1529 extend less than the entire length of the layer 1520. For instance, the proximal ends and/or the distal ends of the slots 1529 may be closed off, or blocked. The configuration of the slots 1529 can be selected so as to provide an appropriate tissue thickness compensation when the layer 1520 comprises a tissue thickness compensator.

Each slot 1529 is defined by a slot width W and a slot depth D. In various embodiments, the slot width W can be sized and configured such that the side walls of the slots 1529 can engage the projections 1519. In at least one such embodiment, the projections 1519 can be press-fit within the slots 1529 wherein the layer 1520 can be releasably held to the cartridge body 1510 by the interaction between the projections 1519 and the slots 1529. In other embodiments, the slot width W can be sized and configured such there is a clearance-fit between the side walls of the slots 1529 and the projections 1519.

In various embodiments, further to the above, the slot depth D can be sized and configured such that the bottom walls of the slots 1529 contact the top surfaces of the projections 1519. In at least one instance, the bottom walls of the slots 1529 can contact the top surfaces of the projections 1519 when the bottom surface 1524 of the layer 1520 is in contact with the deck 1514. In certain other instances, the bottom surface 1524 of the layer 1520 may not be in contact with the deck 1514 when the bottom surfaces of the slots 1529 are positioned against the top surfaces of the projections 1519. In such instances, the layer 1520 can be held in an elevated position above the deck 1514. In use, the compressive pressure applied to the layer 1520 when tissue is clamped between the staple cartridge 1500 and an anvil can push the layer 1520 toward the deck 1514. In certain instances, the bottom walls of the slots 1529 may not be in contact with the projections 1519 when the bottom surface 1524 of the layer 1520 is positioned against the deck 1514. Similar to the above, the compressive pressure applied to the layer 1520 when tissue is clamped between the staple cartridge 1500 and an anvil can push the bottom surfaces of the slots 1529 against the projections 1519.

Figure 36:
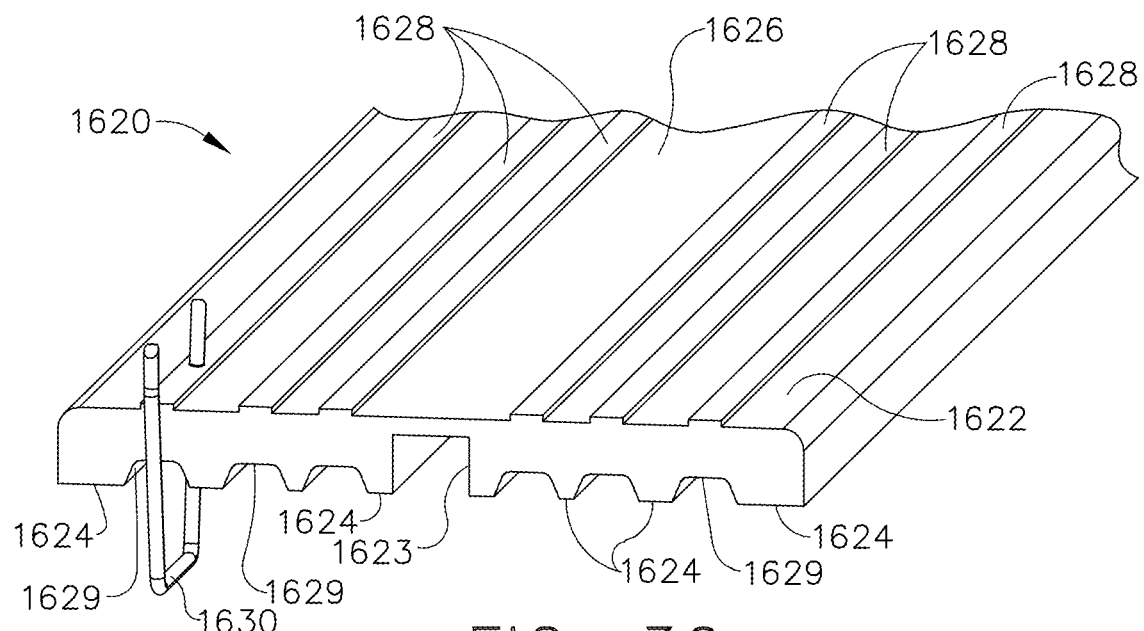
FIG. 36 is a partial perspective view of a layer in accordance with at least one alternative embodiment.

Referring again to FIG. 35, the longitudinal slots 1529 defined in the layer 1520 define portions of the layer 1520 having a cross-section which is thinner than the cross-sections of the other portions of the layer 1520. Turning now to FIG. 36, a layer 1620 comprises a distal end 1622, a bottom surface 1624, a top surface 1626, and a longitudinal slot 1623 defined therein which is aligned, or alignable, with the longitudinal slot 1513 defined in the cartridge body 1510, for example. Similar to the above, the layer 1620 comprises longitudinal slots 1629 which are aligned, or alignable, with the longitudinal rows of projections 1519 extending from the cartridge body 1510. The layer 1620 further comprises ridges 1628 extending from the top surface 1626. The ridges 1628 are aligned, or at least substantially aligned, with the slots 1629. The ridges 1628 increase the cross-section of the portions of the layer 1620 including the longitudinal slots 1629. The ridges 1628 are also aligned with the staple cavities 1515. When staples, such as staples 1630, for example, are ejected from the staple cavities 1515, the staples 1630 can capture the portions of the layer 1620 including the slots 1629 and the ridges 1628.

As illustrated in FIG. 36, the slots 1629 decrease the cross-sectional thickness of the layer 1620 more than the ridges 1628 increase the cross-sectional thickness of the layer 1620, for example. In other embodiments, the slots 1629 can decrease the cross-sectional thickness of the layer 1620 less than the ridges 1628 increase the cross-sectional thickness of the layer 1620, for example. In certain embodiments, the slots 1629 can decrease the cross-sectional thickness of the layer 1620 the same amount that the ridges 1628 increase the cross-sectional thickness of the layer 1620, for example. The configuration of the ridges 1628 and the slots 1629 can be selected so as to provide the appropriate tissue thickness compensation when the layer 1620 comprises a tissue thickness compensator.

Figure 37:
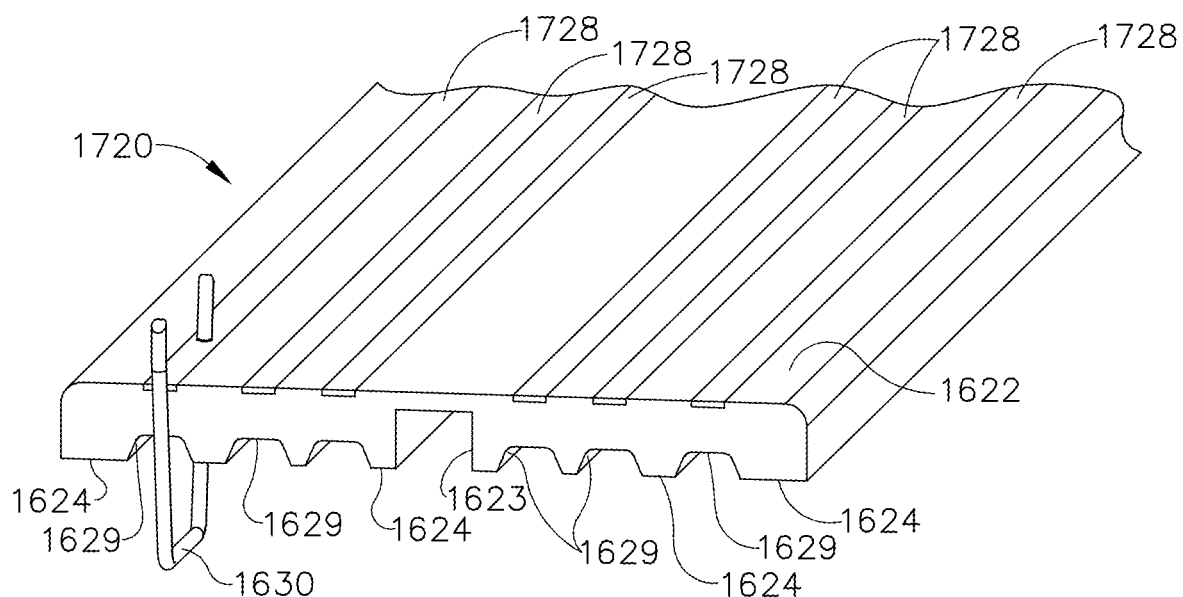
FIG. 37 is a partial perspective view of a layer in accordance with at least one alternative embodiment.

Referring again to FIG. 35, the layer 1520 is comprised of a single piece of material; however, other embodiments are envisioned in which a layer is comprised of two or more pieces of material that have been assembled together. Turning now to FIG. 37, a layer 1720 comprises inserts 1728 which are aligned with the longitudinal slots 1629 of the layer 1720 and the staple cavities 1515 of the cartridge body 1510, for example. The inserts 1728 are embedded in the layer 1720. In at least one instance, the layer 1720 can be molded around the inserts 1728. In certain instances, the layer 1720 can include grooves defined therein wherein the inserts 1728 can be positioned in the grooves. In at least one such instance, at least one adhesive could be utilized to hold the inserts 1728 in the grooves. The inserts 1728 are comprised of a different material than the other portions of the layer 1720; however, other embodiments are envisioned in which they are comprised of the same material. The inserts 1728 are comprised of a denser material than the other portions of the layer 1720; however, other embodiments are envisioned in which the inserts 1728 comprise any suitable density. Similar to the above, the staples 1630, for example, can be configured to capture the inserts 1728 therein when the staples 1630 are deformed. The configuration of the inserts 1728 can be selected so as to provide the appropriate tissue thickness compensation when the layer 1720 comprises a tissue thickness compensator.

In various instances, a layer of material can comprise buttress material and/or a tissue thickness compensator, for example. The layer of material can be comprised of Gore SeamGuard material, Synovis Peri-Strips material, and/or polyurethane, for example. The entire disclosure of U.S. patent application Ser. No. 13/763,095, entitled LAYER ARRANGEMENTS FOR SURGICAL STAPLE CARTRIDGES, filed on Feb. 28, 2013, now U.S. Pat. No. 9,770,245, is incorporated by reference herein. The entire disclosures of U.S. patent application Ser. No. 13/531,619, entitled TISSUE STAPLER HAVING A THICKNESS COMPENSATOR COMPRISING INCORPORATING A HEMOSTATIC AGENT, filed on Jun. 25, 2012, now U.S. Pat. No. 9,345,477, U.S. patent application Ser. No. 13/531,623, entitled TISSUE STAPLER HAVING A THICKNESS COMPENSATOR INCORPORATING AN OXYGEN GENERATING AGENT, filed on Jun. 25, 2012, now U.S. Pat. No. 9,320,518, U.S. patent application Ser. No. 13/531,627, entitled TISSUE STAPLER HAVING A THICKNESS COMPENSATOR INCORPORATING AN ANTI-MICRO- BIAL AGENT, filed on Jun. 25, 2012, now U.S. Pat. No. 9,307,965, and U.S. patent application Ser. No. 13/531,630, entitled TISSUE STAPLER HAVING A THICKNESS COMPENSATOR INCORPORATING AN ANTI-INFLAMMATORY AGENT, filed on Jun. 25, 2012, now U.S. Pat. No. 9,314,246, are incorporated by reference herein. A layer can be comprised of a bioabsorbable material and/or a non-bioabsorbable material. In some instances, a layer of material can be attached to the deck. In at least one instance, at least one adhesive can be utilized to releasably adhere the layer to the deck. In some instances, the layer of material can be releasably attached to the deck utilizing one or more sutures or straps, for example. In certain instances, the layer can comprise a solid piece of material. In some instances, the layer can include apertures defined therein.

Further to the above, the staples being deployed from a staple cartridge can puncture the layer before entering into the tissue. The staples may also re-puncture the layer as they are being deformed by the anvil. In various instances, thicker or more puncture-resistant strips of polymer could be integrated into the layer, for example. For instance, such strips could be integrated into the tissue-contacting surface of the layer. In at least one instance, each strip could be 0.003" thick and comprised of 90/10 PLA/PCL, for example. In certain instances, each strip could be 0.006" thick 25/75 PGA/PCL, for example. The strips could be welded into the foam as part of a felting process, for example. The disclosure of U.S. patent application Ser. No. 14/187,383, entitled IMPLANTABLE LAYERS AND METHODS FOR ALTERING IMPLANTABLE LAYERS FOR USE WITH SURGICAL FASTENING INSTRUMENTS, now U.S. Pat. No. 9,839,422, is incorporated by reference in its entirety. The felting process could serve another purpose which is to create a closed cell foam and/or a continuous tissue contacting surface. In some instances, separate thin film strips could be welded into the tissue-contacting side of the foam. The various methods disclosed herein can create a composite absorbable material with features or zones aligned with the staples that have differing properties for initial staple puncturing, forming, and re-piercing.

A layer, such as buttress material, for example, may be made from any biocompatible material. Buttress material may be formed from a natural material and/or a synthetic material. Buttress material may be bioabsorbable and/or non-bioabsorbable. It should be understood that any combination of natural, synthetic, bioabsorbable and non-bioabsorbable materials may be used to form buttress material. Some non-limiting examples of materials from which the buttress material may be made include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and/or combinations thereof, for example.

Natural biological polymers can be used in forming the buttress material. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and/or combinations thereof, for example. Natural biological polymers may be combined with any of the other polymeric materials described herein to produce the buttress material. Collagen of human and/or animal origin, e.g., type I porcine or bovine collagen, type I human collagen or type III human collagen may be used to form the buttress material. The buttress material may be made from denatured collagen or collagen which has at least partially lost its helical structure through heating or any other method, consisting mainly of non-hydrated chains, of molecular weight close to 100 kDa, for example. The term "denatured collagen" means collagen which has lost its helical structure. The collagen used for the porous layer as described herein may be native collagen or atellocollagen, notably as obtained through pepsin digestion and/or after moderate heating as defined previously, for example. The collagen may have been previously chemically modified by oxidation, methylation, succinylation, ethylation and/or any other known process.

Where the buttress material is fibrous, the fibers may be filaments or threads suitable for knitting or weaving or may be staple fibers, such as those frequently used for preparing non-woven materials. The fibers may be made from any biocompatible material. The fibers may be formed from a natural material or a synthetic material. The material from which the fibers are formed may be bioabsorbable or non-bioabsorbable. It should be understood that any combination of natural, synthetic, bioabsorbable and non-bioabsorbable materials may be used to form the fibers. Some non-limiting examples of materials from which the fibers may be made include, but are not limited to, poly(lactic acid), poly(glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and/or combinations thereof. Where the buttress material is fibrous, the buttress material may be formed using any method suitable to forming fibrous structures including, but not limited to, knitting, weaving, non-woven techniques and the like, for example. Where the buttress material is a foam, the porous layer may be formed using any method suitable to forming a foam or sponge including, but not limited to the lyophilization or freeze-drying of a composition, for example.

The buttress material may possesses haemostatic properties. Illustrative examples of materials which may be used in providing the buttress material with the capacity to assist in stopping bleeding or hemorrhage include, but are not limited to, poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, epsilon amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and/or combinations thereof, for example. The use of natural biological polymers, and in particular proteins, may be useful in forming buttress material having haemostatic properties. Suitable natural biological polymers include, but are not limited to, collagen, gelatin, fibrin, fibrinogen, elastin, keratin, albumin and/or combinations thereof, for example. Natural biological polymers may be combined with any other haemostatic agent to produce the porous layer of the buttress. The entire disclosure of U.S. Pat. No. 8,496,683, entitled BUTTRESS AND SURGICAL STAPLING APPARATUS, which issued on Jul. 30, 2013, is incorporated by reference herein.

In various circumstances, the tissue thickness compensator assembly may comprise a polymeric composition. The polymeric composition may comprise one or more synthetic polymer and/or one or more non-synthetic polymer. The synthetic polymer may comprise a synthetic absorbable polymer and/or a synthetic non-absorbable polymer. In various circumstances, the polymeric composition may comprise a biocompatible foam, for example. The biocompatible foam may comprise a porous, open cell foam and/or a porous, closed cell foam, for example. The biocompatible foam can have a uniform pore morphology or may have a gradient pore morphology (i.e. small pores gradually increasing in size to large pores across the thickness of the foam in one direction). In various circumstances, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator assembly may comprise a foam reinforced by a filamentous matrix or may comprise a foam having an additional hydrogel layer that expands in the presence of bodily fluids to further provide the compression on the tissue. In various circumstances, a tissue thickness compensator assembly could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In certain circumstances, a tissue thickness compensator assembly could be reinforced with fibrous non-woven materials or fibrous mesh type elements, for example, that can provide additional flexibility, stiffness, and/or strength. In various circumstances, a tissue thickness compensator assembly that has a porous morphology which exhibits a gradient structure such as, for example, small pores on one surface and larger pores on the other surface. Such morphology could be more optimal for tissue in-growth or hemostatic behavior. Further, the gradient could be also compositional with a varying bio-absorption profile. A short term absorption profile may be preferred to address hemostasis while a long term absorption profile may address better tissue healing without leakages.

Examples of non-synthetic polymers include, but are not limited to, lyophilized polysaccharide, glycoprotein, elastin, proteoglycan, gelatin, collagen, and oxidized regenerated cellulose (ORC). Examples of synthetic absorbable polymers include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and ε-caprolactone (PGCL), a copolymer of glycolide and trimethylene carbonate, poly(glycerol sebacate) (PGS), polydioxanone, poly(orthoesters), polyanhydrides, polysaccharides, poly(ester-amides), tyrosine-based polyarylates, tyrosine-based polyiminocarbonates, tyrosine-based polycarbonates, poly (D,L-lactide-urethane), poly(B-hydroxybutyrate), poly(E-caprolactone), polyethyleneglycol (PEG), poly[bis(carboxylatophenoxy)phosphazene], poly(amino acids), pseudo-poly (amino acids), absorbable polyurethanes, and combinations thereof. In various circumstances, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various circumstances, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various circumstances, the polymeric composition may comprise from approximately 90% to approximately 95% by weight of the polymeric composition of PGA and approximately 5% to approximately 10% by weight of the polymeric composition of PLA, for example.

In various circumstances, the synthetic absorbable polymer may comprise a bioabsorbable, biocompatible elastomeric copolymer. Suitable bioabsorbable, biocompatible elastomeric copolymers include but are not limited to copolymers of epsilon-caprolactone and glycolide (preferably having a mole ratio of epsilon-caprolactone to glycolide of from about 30:70 to about 70:30, preferably 35:65 to about 65:35, and more preferably 45:55 to 35:65); elastomeric copolymers of epsilon-caprolactone and lactide, including L-lactide, D-lactide blends thereof or lactic acid copolymers (preferably having a mole ratio of epsilon-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of epsilon-caprolactone and p-dioxanone (preferably having a mole ratio of epsilon-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and epsilon-caprolactone. In another embodiment, the elastomeric copolymer is a copolymer of lactide and epsilon-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various circumstances, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-E-caprolactone-poliglecaprolactone 25) copolymer, commercially available from Ethicon under the trade designation MONOCRYL, for example.

Examples of synthetic non-absorbable polymers include, but are not limited to, foamed polyurethane, polypropylene (PP), polyethylene (PE), polycarbonate, polyamides, such as nylon, polyvinylchloride (PVC), polymethylmetacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, and combinations thereof. The synthetic non-absorbable polymers may include, but are not limited to, foamed elastomers and porous elastomers, such as, for example, silicone, polyisoprene, and rubber. In various circumstances, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

The polymeric composition of a tissue thickness compensator assembly may be characterized by percent porosity, pore size, and/or hardness, for example. In various circumstances, the polymeric composition may have a percent porosity from approximately 30% by volume to approximately 99% by volume, for example. In certain circumstances, the polymeric composition may have a percent porosity from approximately 60% by volume to approximately 98% by volume, for example. In various circumstances, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various circumstances, the polymeric composition may comprise a greater than 85% porosity by volume. The polymeric composition may have a pore size from approximately 5 micrometers to approximately 2000 micrometers, for example. In various circumstances, the polymeric composition may have a pore size between approximately 10 micrometers to approximately 100 micrometers, for example. In at least one such embodiment, the polymeric composition can comprise a copolymer of PGA and PCL, for example. In certain circumstances, the polymeric composition may have a pore size between approximately 100 micrometers to approximately 1000 micrometers, for example. In at least one such embodiment, the polymeric composition can comprise a copolymer of PLLA and PCL, for example. According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, "Standard Test Method for Rubber Property-Durometer Hardness", the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various circumstances, the durometer may be determined in accordance with any suitable scale, such as Type A and/or Type OO scales, for example, in accordance with ASTM D2240-00. In various circumstances, the polymeric composition of a tissue thickness compensator assembly may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various circumstances, the polymeric composition of a tissue thickness compensator assembly may have a Shore A Hardness value of less than 15 A. In various circumstances, the polymeric composition of a tissue thickness compensator assembly may have a Shore A Hardness value of less than 10 A. In various circumstances, the polymeric composition of a tissue thickness compensator assembly may have a Shore A Hardness value of less than 5 A. In certain circumstances, the polymeric material may have a Shore OO composition value from approximately 35 OO to approximately 75 OO, for example.

In various circumstances, the polymeric composition may have at least two of the above-identified properties. In various circumstances, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various circumstances, the polymeric composition may comprise a pharmaceutically active agent. The polymeric composition may release a therapeutically effective amount of the pharmaceutically active agent. In various circumstances, the pharmaceutically active agent may be released as the polymeric composition is desorbed/absorbed. In various circumstances, the pharmaceutically active agent may be released into fluid, such as, for example, blood, passing over or through the polymeric composition. Examples of pharmaceutically active agents may include, but are not limited to, hemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

Various methods are disclosed herein for manufacturing a tissue thickness compensator. Such methods could be used to manufacture any suitable layer for use with a fastener cartridge and/or a surgical fastening instrument, for example. Such a layer can comprise a less than one hundred percent dense composition which can be created utilizing any suitable process. For instance, such processes can include, for example, extruding, injection molding, weaving, lyophilization, gas-foaming, and/or melt-blowing processes. Some processes may produce a foam while other processes may not produce a foam; however, in any event, all such embodiments are contemplated for use with all of the embodiments disclosed herein.

The entire disclosures of:
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;
U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;
U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;
U.S. Pat. No. 7,670,334, entitled SURGICAL INSTRUMENT HAVING AN ARTICULATING END EFFECTOR, which issued on Mar. 2, 2010;
U.S. Pat. No. 7,753,245, entitled SURGICAL STAPLING INSTRUMENTS, which issued on Jul. 13, 2010;
U.S. Pat. No. 8,393,514, entitled SELECTIVELY ORIENTABLE IMPLANTABLE FASTENER CARTRIDGE, which issued on Mar. 12, 2013;
U.S. patent application Ser. No. 11/343,803, entitled SURGICAL INSTRUMENT HAVING RECORDING CAPABILITIES, now U.S. Pat. No. 7,845,537;
U.S. patent application Ser. No. 12/031,573, entitled SURGICAL CUTTING AND FASTENING INSTRUMENT HAVING RF ELECTRODES, filed Feb. 14, 2008;
U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;
U.S. patent application Ser. No. 12/235,782, entitled MOTOR-DRIVEN SURGICAL CUTTING INSTRUMENT, now U.S. Pat. No. 8,210,411;
U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;
U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;
U.S. patent application Ser. No. 12/893,461, entitled STAPLE CARTRIDGE, filed Sep. 29, 2012, now U.S. Pat. No. 8,733,613;
U.S. patent application Ser. No. 13/036,647, entitled SURGICAL STAPLING INSTRUMENT, filed Feb. 28, 2011, now U.S. Pat. No. 8,561,870;
U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;
U.S. patent application Ser. No. 13/524,049, entitled ARTICULATABLE SURGICAL INSTRUMENT COMPRISING A FIRING DRIVE, filed on Jun. 15, 2012; now U.S. Pat. No. 9,101,358;
U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;
U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;
U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and
U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although the various embodiments of the devices have been described herein in connection with certain disclosed embodiments, many modifications and variations to those embodiments may be implemented. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A staple cartridge assembly, comprising:
    a cartridge body, comprising:
        a deck;
        a plurality of staple cavities, wherein each staple cavity extends into the cartridge body forming an opening in the deck;
        a cartridge slot defined in the cartridge body; and
        a first row of projections comprising a first plurality of projections;
        a second row of projections comprising a second plurality of projections;
    a plurality of staples removably positioned in the staple cavities; and
    an implantable layer releasably secured to the cartridge body, wherein the implantable layer comprises:
        a tissue-facing surface; and
        a deck-facing surface opposite the tissue-facing surface, wherein the deck-facing surface comprises:
            a first longitudinal recess aligned with the first row of projections; and
            a second longitudinal recess aligned with the second row of projections.

2. The staple cartridge assembly of claim 1, wherein the first plurality of projections are dimensioned to be press-fittingly received in the first longitudinal recess of the implantable layer, and wherein the second plurality of projections are dimensioned to be press-fittingly received in the second longitudinal recess of the implantable layer.

3. The staple cartridge assembly of claim 1, wherein at least one projection of the first plurality of projections is press fit in the first longitudinal recess of the implantable layer, and wherein at least one projection of the second plurality of projections is press fit in the second longitudinal recess of the implantable layer.

4. The staple cartridge assembly of claim 1, wherein the deck-facing surface further comprises a plurality of non-recessed portions flanking the first longitudinal recess and the second longitudinal recess.

5. The staple cartridge assembly of claim 4, wherein the first longitudinal recess defines a first thickness between the tissue-facing surface and the deck-facing surface, wherein the second longitudinal recess defines a second thickness between the tissue-facing surface and the deck-facing surface, wherein the plurality of non-recessed portions define a third thickness between the tissue-facing surface and the deck-facing surface, and wherein the third thickness is greater than the first thickness and the second thickness.

6. The staple cartridge assembly of claim 1, wherein the cartridge body further comprises a plurality of rows of projections, wherein the implantable layer further comprises a plurality of recessed portions, and wherein each recessed portion is aligned with a row of projections.

7. The staple cartridge assembly of claim 1, wherein the implantable layer further comprises:
    a longitudinal slot aligned with the cartridge slot;
    a first plurality of longitudinal recesses positioned on a first side of the longitudinal slot, wherein the first plurality of longitudinal recesses comprises the first longitudinal recess; and
    a second plurality of longitudinal recesses positioned on a second side of the longitudinal slot, wherein the second plurality of longitudinal recesses comprises the second longitudinal recess.

8. The staple cartridge assembly of claim 1, wherein each projection at least partially surrounds a staple cavity of the plurality of staple cavities.

9. The staple cartridge assembly of claim 8, wherein each staple cavity is bordered by at least two projections.

10. The staple cartridge assembly of claim 1, wherein each projection is positioned at a distal end of the staple cavity or a proximal end of the staple cavity.

11. A staple cartridge assembly, comprising:
    a cartridge body, comprising:
        a deck;
        a plurality of staple cavities, wherein each staple cavity extends into the cartridge body forming an opening in the deck; and
        a plurality of longitudinally staggered projections, wherein each longitudinally staggered projection extends away from the deck;
    a plurality of staples removably positioned in the staple cavities; and
    a tissue thickness compensator releasably secured to the cartridge body, wherein the tissue thickness compensator comprises:
        a tissue-facing surface; and
        a deck-facing surface opposite the tissue-facing surface,
    wherein the plurality of longitudinally staggered projections are dimensioned to be press-fittingly received in the deck-facing surface of the tissue thickness compensator.

12. The staple cartridge assembly of claim 11, wherein each projection of the longitudinally staggered projections at least partially surrounds a staple cavity of the plurality of staple cavities.

13. The staple cartridge assembly of claim 11, wherein each projection of the longitudinally staggered projections is positioned at a distal end of the staple cavity or a proximal end of the staple cavity.

14. The staple cartridge assembly of claim 11, wherein each staple cavity is bordered by at least two of the longitudinally staggered projections.

15. The staple cartridge assembly of claim 11, wherein the deck-facing surface comprises:
   a longitudinal recessed portion; and
   a plurality of flanking portions adjacent to the recessed portion, wherein the plurality of flanking portions comprises:
      a first longitudinal flanking portion laterally flanking a first side of the longitudinal recessed portion; and
      a second longitudinal flanking portion laterally flanking a second side of the longitudinal recessed portion.

16. The staple cartridge assembly of claim 15, wherein the longitudinal recessed portion defines a first thickness between the tissue-facing surface and the deck-facing surface, wherein the plurality of flanking portions comprises a second thickness between the tissue-facing surface and the deck-facing surface, and wherein the second thickness is greater than the first thickness.

17. A staple cartridge assembly, comprising:
   a cartridge body, comprising:
      a deck;
      a plurality of staple cavities, wherein each staple cavity extends into the cartridge body forming an opening in the deck; and
      a row of projections comprising a plurality of projections, wherein each projection extends away from the deck;
   a layer releasably secured to the cartridge body, wherein the layer comprises:
      a tissue-facing surface; and
      a deck-facing surface opposite the tissue-facing surface, wherein the deck-facing surface comprises a recess aligned with the row of projections;
   wherein at least one of the plurality of projections is press-fit in the recess of the layer.

18. The staple cartridge assembly of claim 17, wherein each projection at least partially surrounds a staple cavity of the plurality of staple cavities.

19. The staple cartridge assembly of claim 17, wherein the recess comprises a longitudinal recessed portion, wherein the layer further comprises a plurality of flanking portions positioned adjacent to the recess, the plurality of flanking portions comprising:
   a first longitudinal flanking portion laterally flanking a first side of the longitudinal recessed portion; and
   a second longitudinal flanking portion laterally flanking a second side of the longitudinal recessed portion.

20. The staple cartridge assembly of claim 19 wherein the recess defines a first thickness between the tissue-facing surface and the deck-facing surface, wherein the plurality of flanking portions comprises a second thickness between the tissue-facing surface and the deck-facing surface, and wherein the second thickness is greater than the first thickness.

\* \* \* \* \*